(12) United States Patent
Lisowski et al.

(10) Patent No.: US 9,169,299 B2
(45) Date of Patent: Oct. 27, 2015

(54) AAV CAPSID PROTEINS FOR NUCLEIC ACID TRANSFER

(75) Inventors: Leszek Lisowski, San Mateo, CA (US); Mark A. Kay, Los Altos, CA (US)

(73) Assignee: THE BOARD OF TRUSTEES OF THE LELEAND STANFORD JUNIOR UNIVERSITY, Palo Alto, CA (US)

(*) Notice: Subject to any disclaimer, the term of this patent is extended or adjusted under 35 U.S.C. 154(b) by 332 days.

(21) Appl. No.: 13/594,773

(22) Filed: Aug. 24, 2012

(65) Prior Publication Data
US 2013/0059732 A1   Mar. 7, 2013

Related U.S. Application Data

(60) Provisional application No. 61/526,688, filed on Aug. 24, 2011, provisional application No. 61/545,488, filed on Oct. 10, 2011.

(51) Int. Cl.
*C07K 14/005* (2006.01)

(52) U.S. Cl.
CPC ..... *C07K 14/005* (2013.01); *C12N 2750/14122* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 7,749,492 B2 * | 7/2010 | Bartlett et al. | 424/93.2 |
| 2010/0047174 A1 | 2/2010 | Kay et al. | |

FOREIGN PATENT DOCUMENTS

| | | |
|---|---|---|
| WO | WO 2006/119432 A2 | 11/2006 |
| WO | WO 2009/137006 A2 | 11/2009 |

OTHER PUBLICATIONS

Rutledge et al. Infections clones and vectors derived from adeno-associated virus (AAV) serotypes other than AAV type 2. Journal of Virology, vol. 72, No. 1, pp. 309-319, Jan. 1998.*

Azuma et al., "Robust expansion of human hepatocytes in Fah-/-/Rag2-/-/Il2rg-/- mice", Nature Biotechnol., vol. 25, No. 8, pp. 903-910 (Epub 2007).
Crameri et al., "DNA shuffling of a family of genes from diverse species accelerates directed evolution", Nature, vol. 391, pp. 288-291 (1998).
Gao et al., "Clades of Adeno-associated viruses are widely disseminated in human tissues", J. Virol., vol. 78, No. 12, pp. 6381-6388 (2004).
Grimm et al., "Preclinical in vivo evaluation of pseudotyped adeno-associated virus vectors for liver gene therapy", Blood, vol. 102, No. 7, pp. 2412-2419 (2003).
International Search Report from related PCT Patent Application No. PCT/US2012/052400, search report mailed on Jan. 18, 2013.
Kern et al., "Identification of a heparin-binding motif on adeno-associated virus type 2 capsids", J. Virol., vol. 77, No. 20, pp. 11072-11081 (2003).
Logan and Shenk, "Adenovirus tripartite leader sequence enhances translation of mRNAs late after infection", Proc. Natl. Acad. Sci. USA, vol. 81, No. 12, pp. 3655-3659 (1984).
Mackett et al., "*Vaccinia virus*: a selectable eukaryotic cloning and expression vector", Proc Natl. Acad. Sci. USA, vol. 79, No. 23, pp. 7415-7419 (1982).
Mackett et al., "General method for production and selection of infectious *Vaccinia virus* recombinants expressing foreign genes", J. Virol., vol. 49, No. 3, pp. 857-864 (1984).
Manno et al., "Successful transduction of liver in hemophilia by AAV-Factor IX and limitations imposed by the host immune response", Nature Medicine, vol. 12, No. 3, pp. 342-347 (2006).
Panicali et al., "Construction of poxviruses as cloning vectors: insertion of the thymidine kinase gene from herpes simplex virus into the DNA of infectious *Vaccinia virus*", Proc. Natl. Acad. Sci. USA, vol. 79, No. 16, pp. 4927-4931 (1982).
Summerford et al., "Membrane-associated heparan sulfate proteoglycan is a receptor for adeno-associated virus type 2 virions", J. Virol., vol. 72, No. 2, pp. 1438-1445 (1998).

* cited by examiner

*Primary Examiner* — Jennifer Dunston
(74) *Attorney, Agent, or Firm* — Judy M. Mohr; Susan L. Harlocker; McDermott Will & Emery LLP

(57) ABSTRACT

Recombinant adeno-associated viral (AAV) capsid proteins are provided. Methods for generating the recombinant adeno-associated viral capsid proteins and a library from which the capsids are selected are also provided.

11 Claims, 50 Drawing Sheets

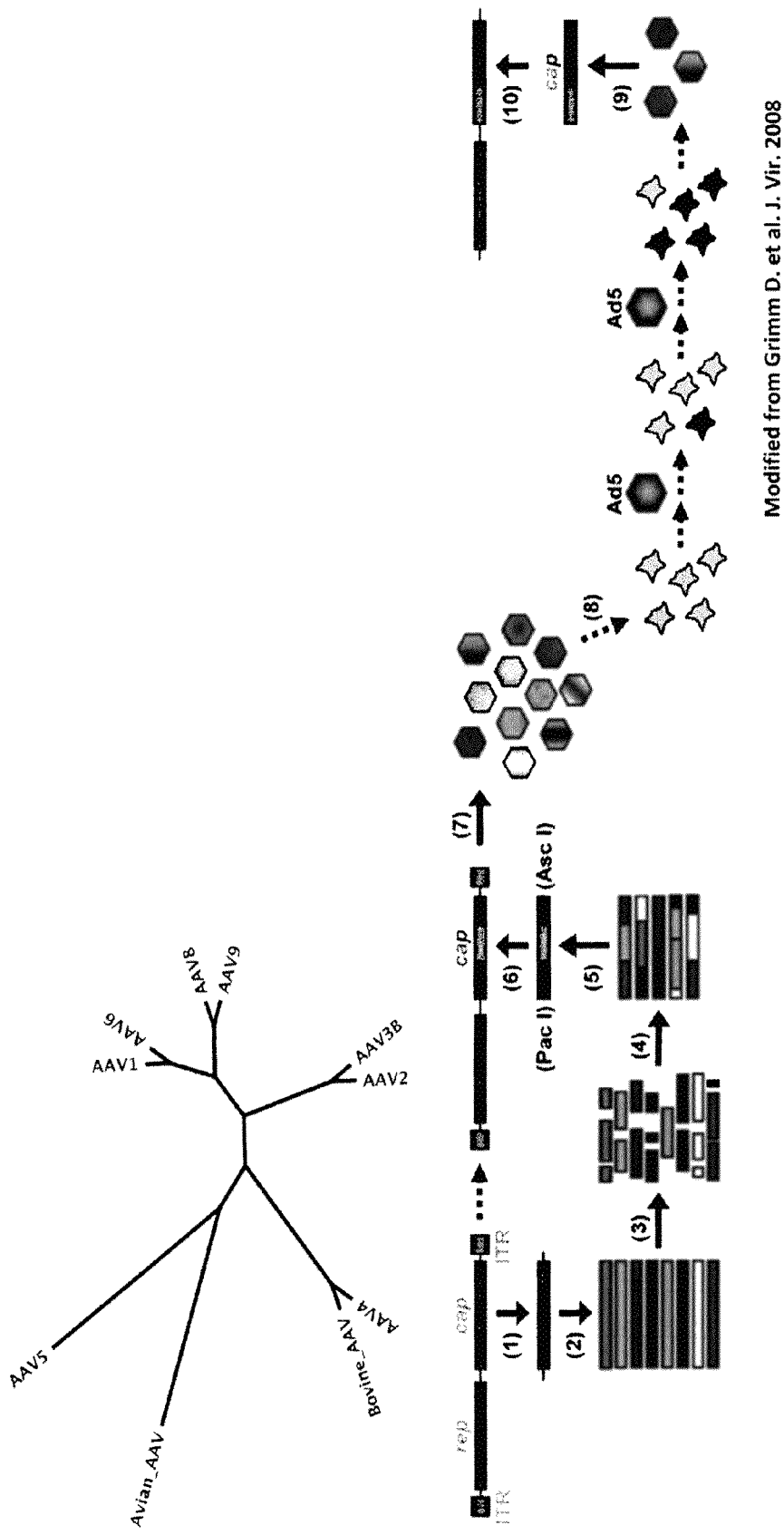

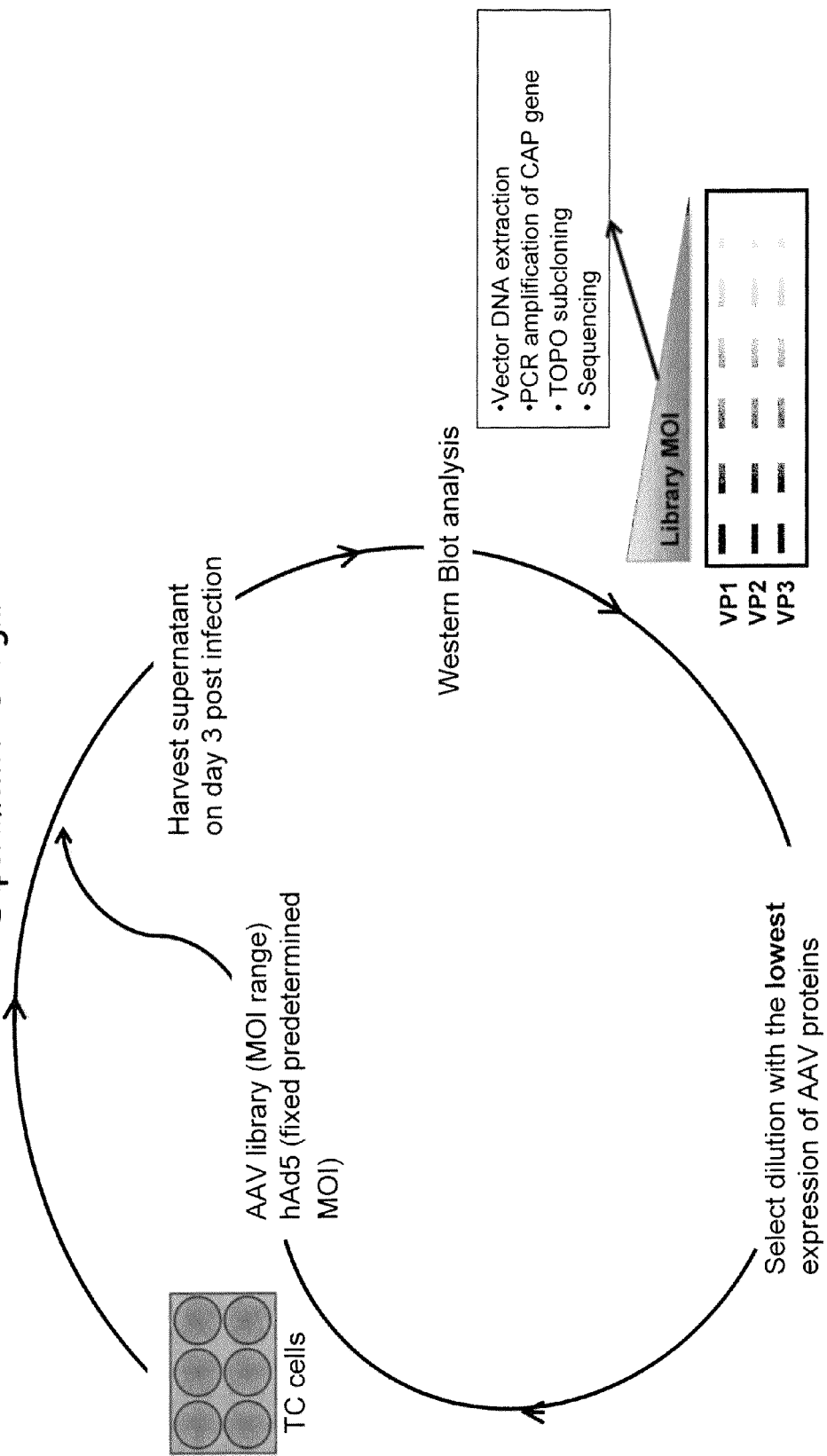
Figure 2. AAV shuffle library selection on TC cell. Experimental Design.

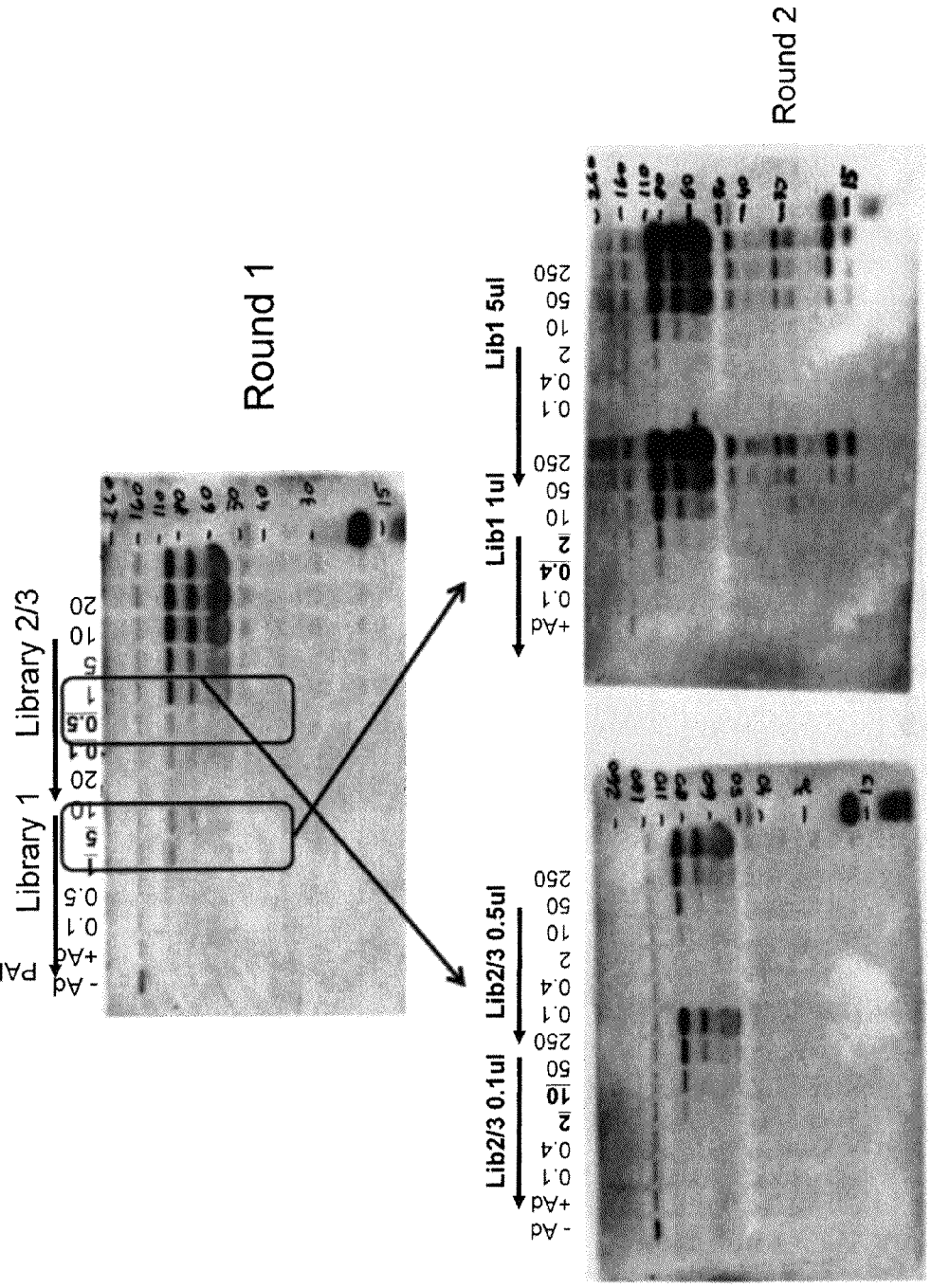
Figure 3. AAV shuffle library selection. hPAEC cells.

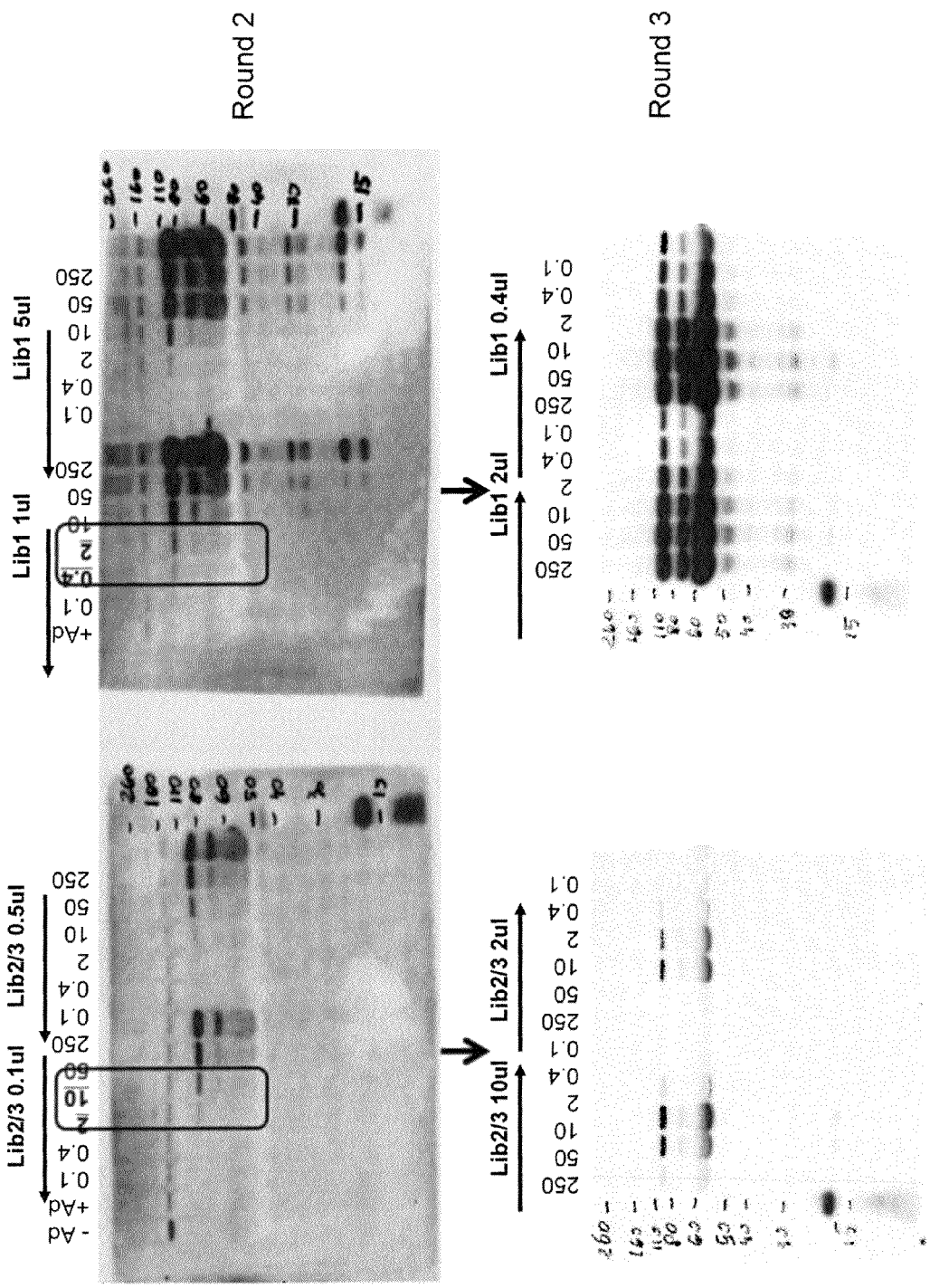

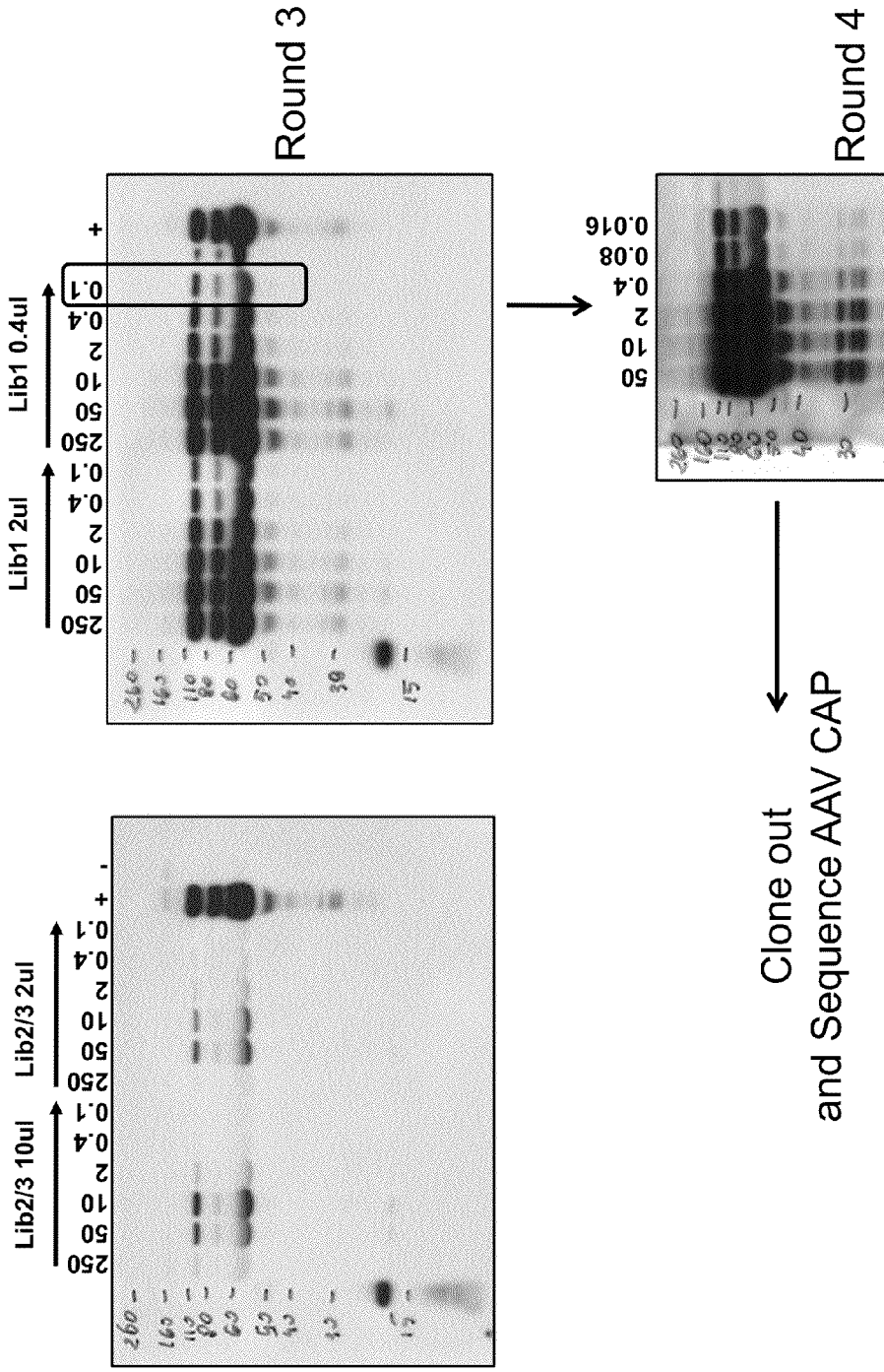

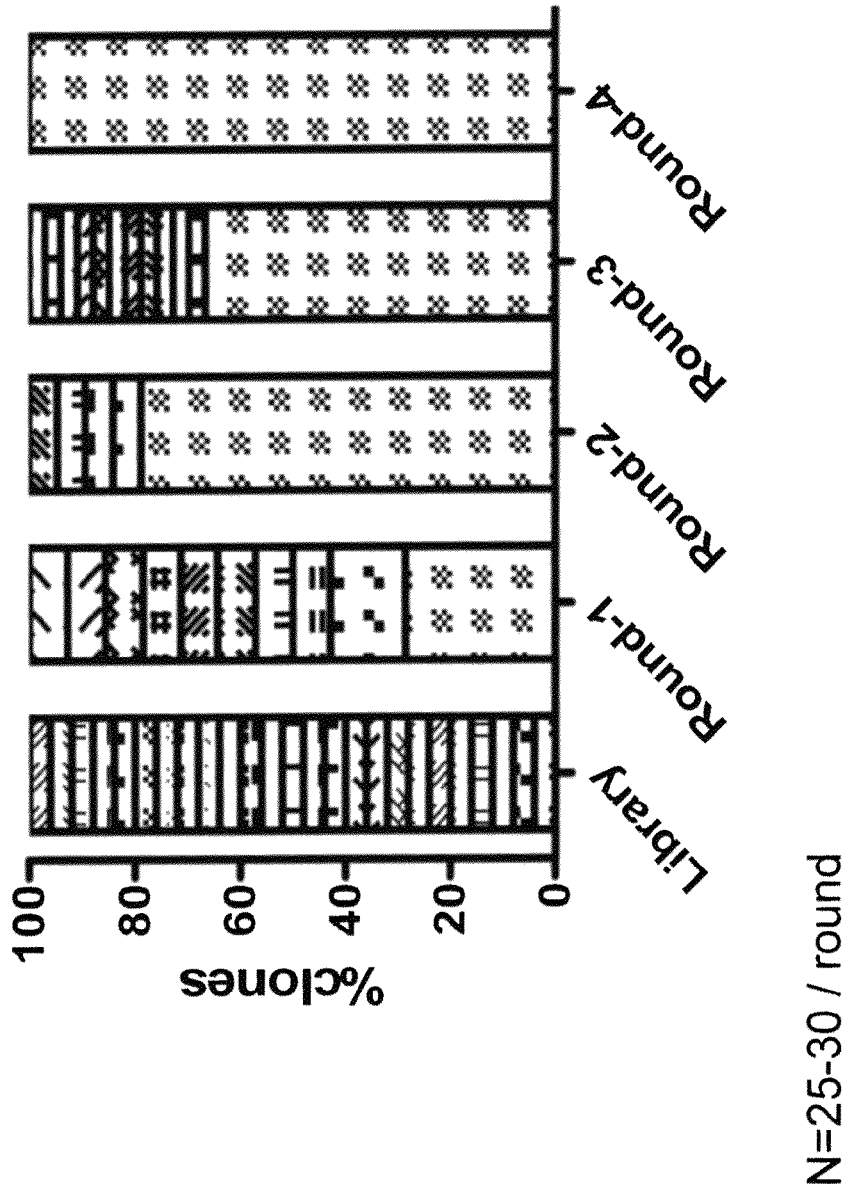
Figure 6. AAV shuffle library selection. hPAEC cells.
N=25-30 / round

Fig. 7: AAV shuffle library selection. AAV-PAEC.
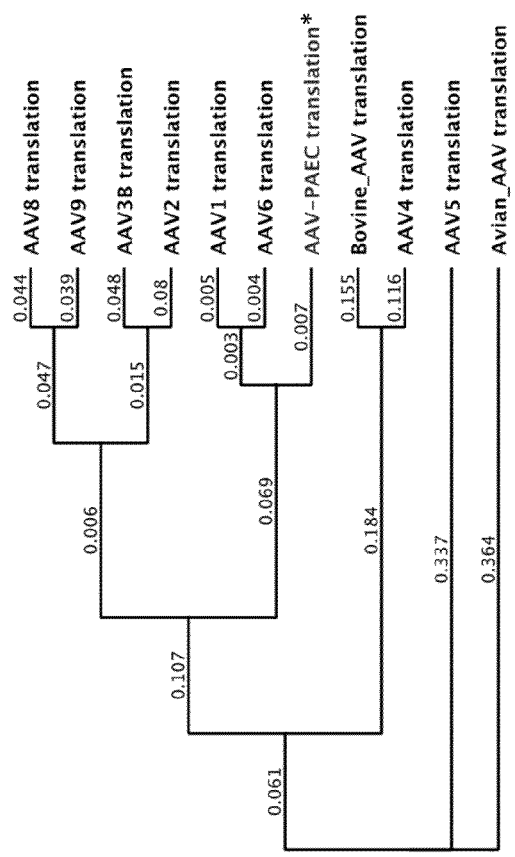
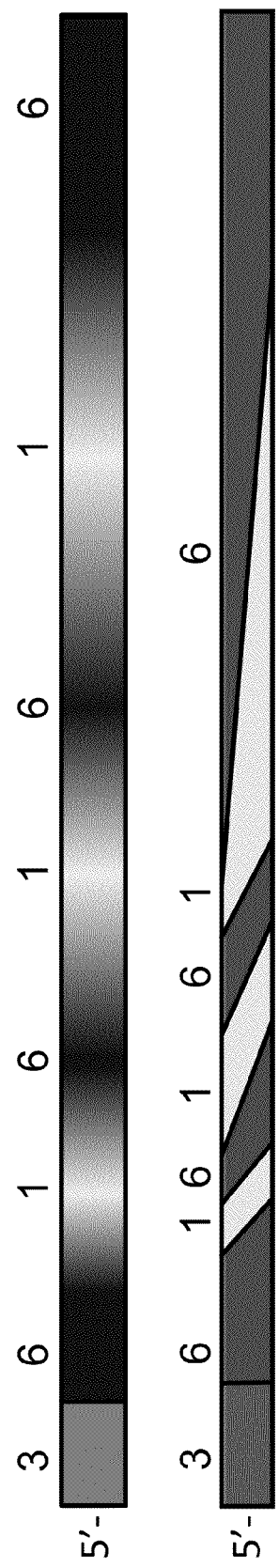

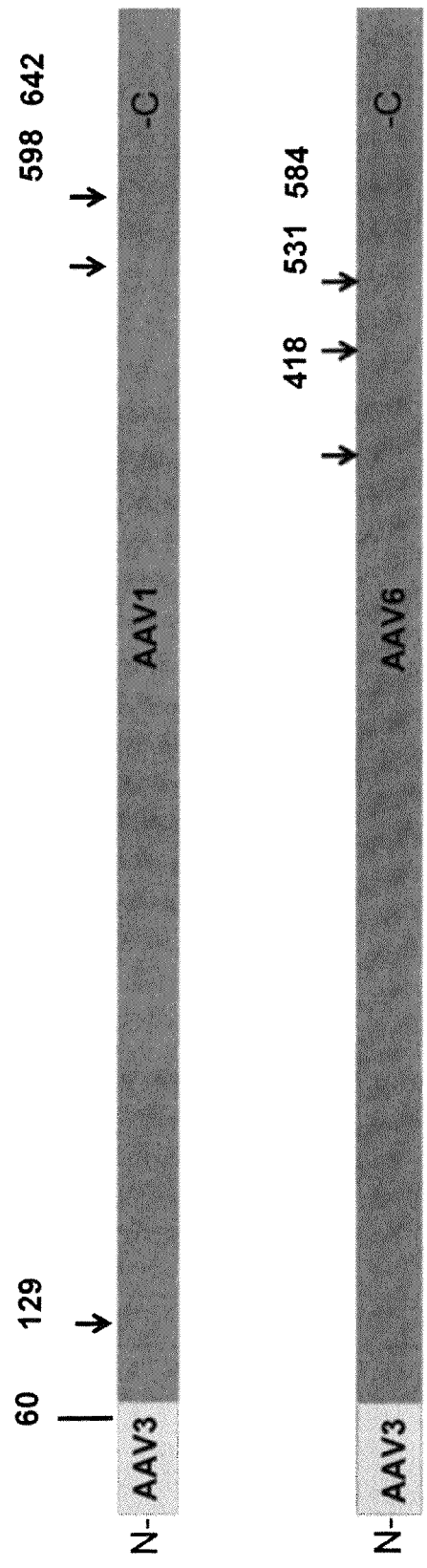
Figure 8. AAV shuffle library selection. AAV-PAEC.
On the amino acid (aa) level...because AAV1 and AAV6 are very similar, if we select AAV1 as the major contributor, then there are 3 aa that come from AAV6. same, if we select AAV6 as the major contributor, then there are 3 aa that come from AAV1.

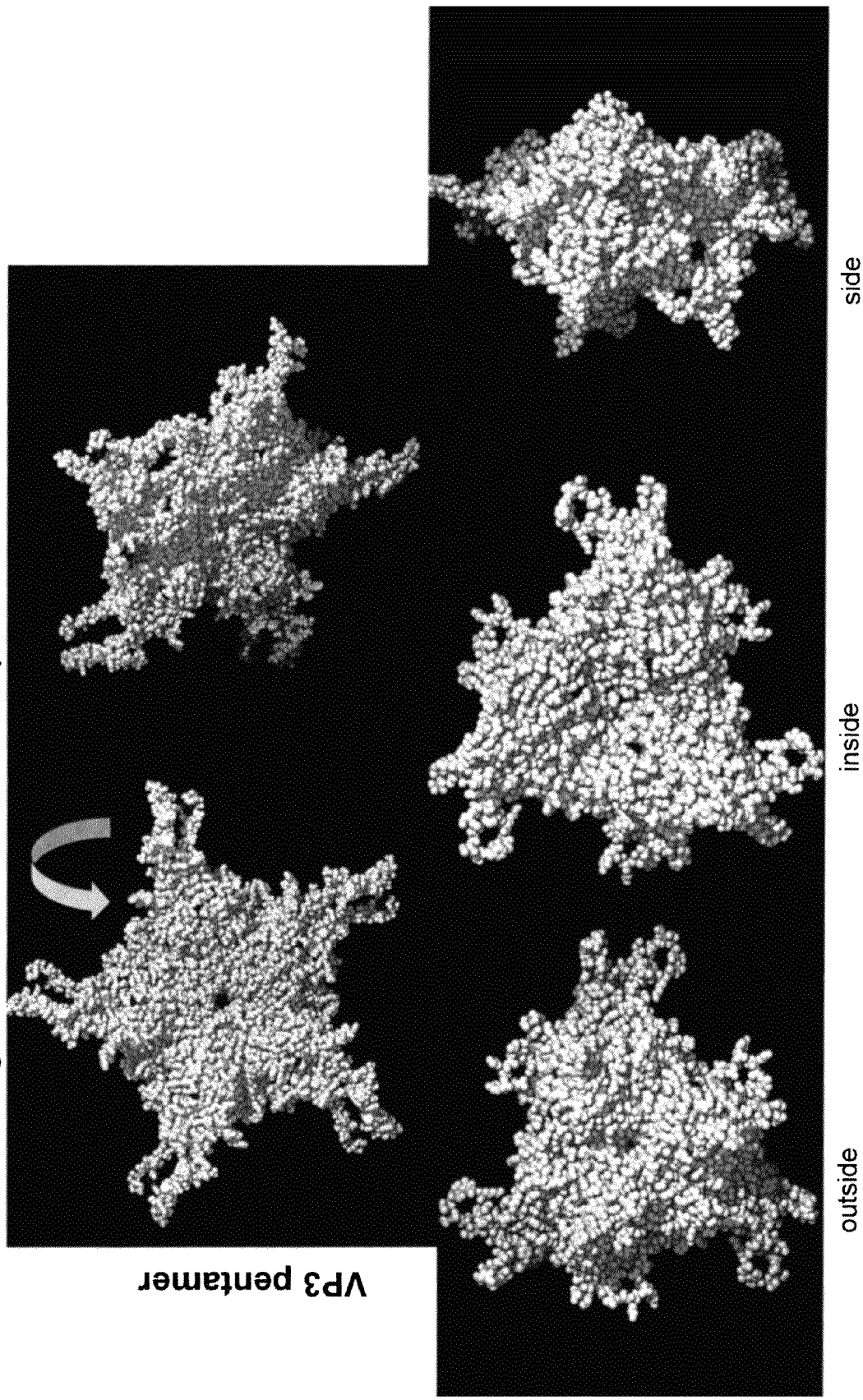
Figure 9. AAV shuffle library selection. AAV-PAEC.

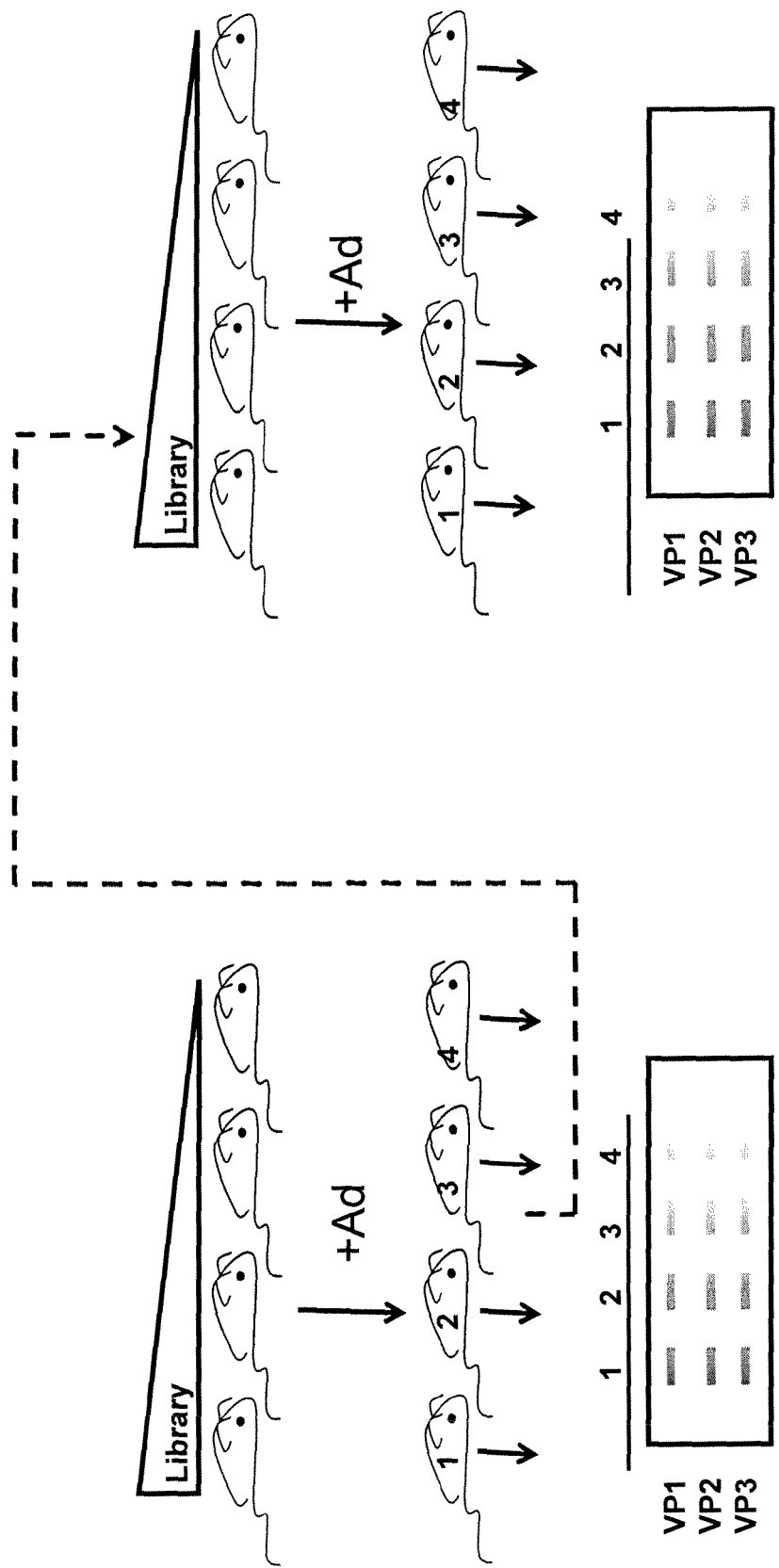
Figure 10. AAV shuffle library screening in FRG mice. Experimental design.

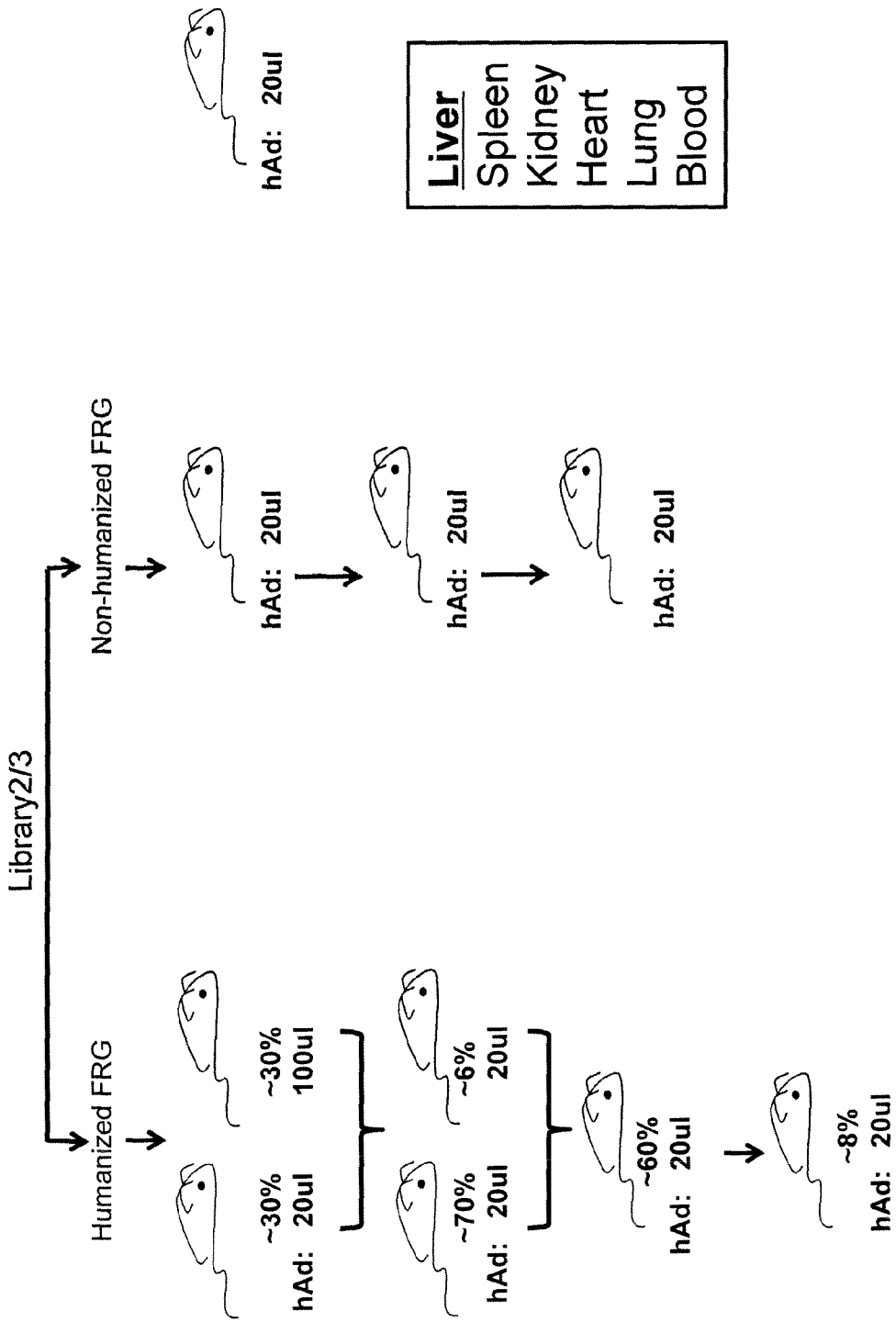
Figure 11. AAV shuffle library screening in FRG mice. Actual experiment.

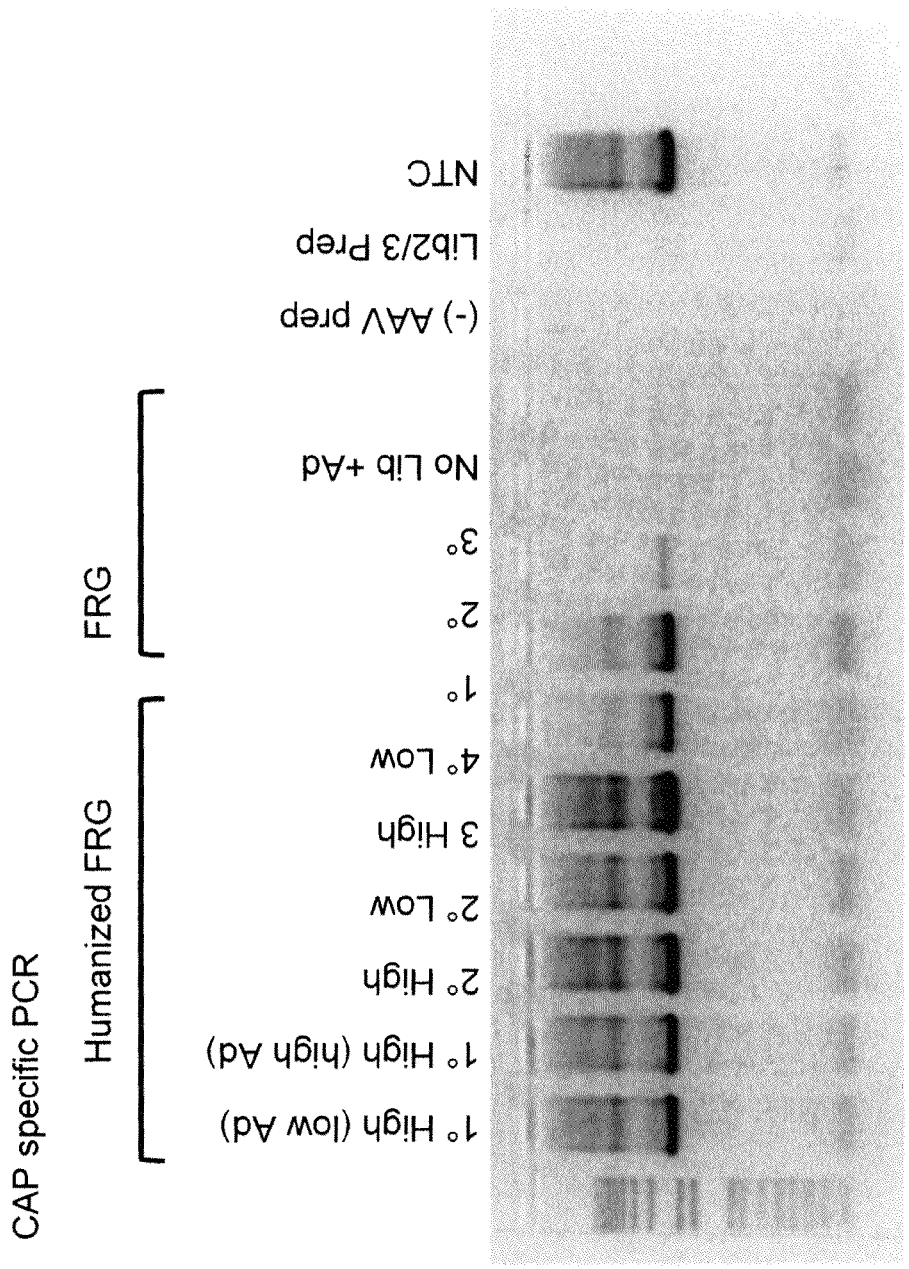
Figure 12. AAV shuffle library screening in FRG mice.

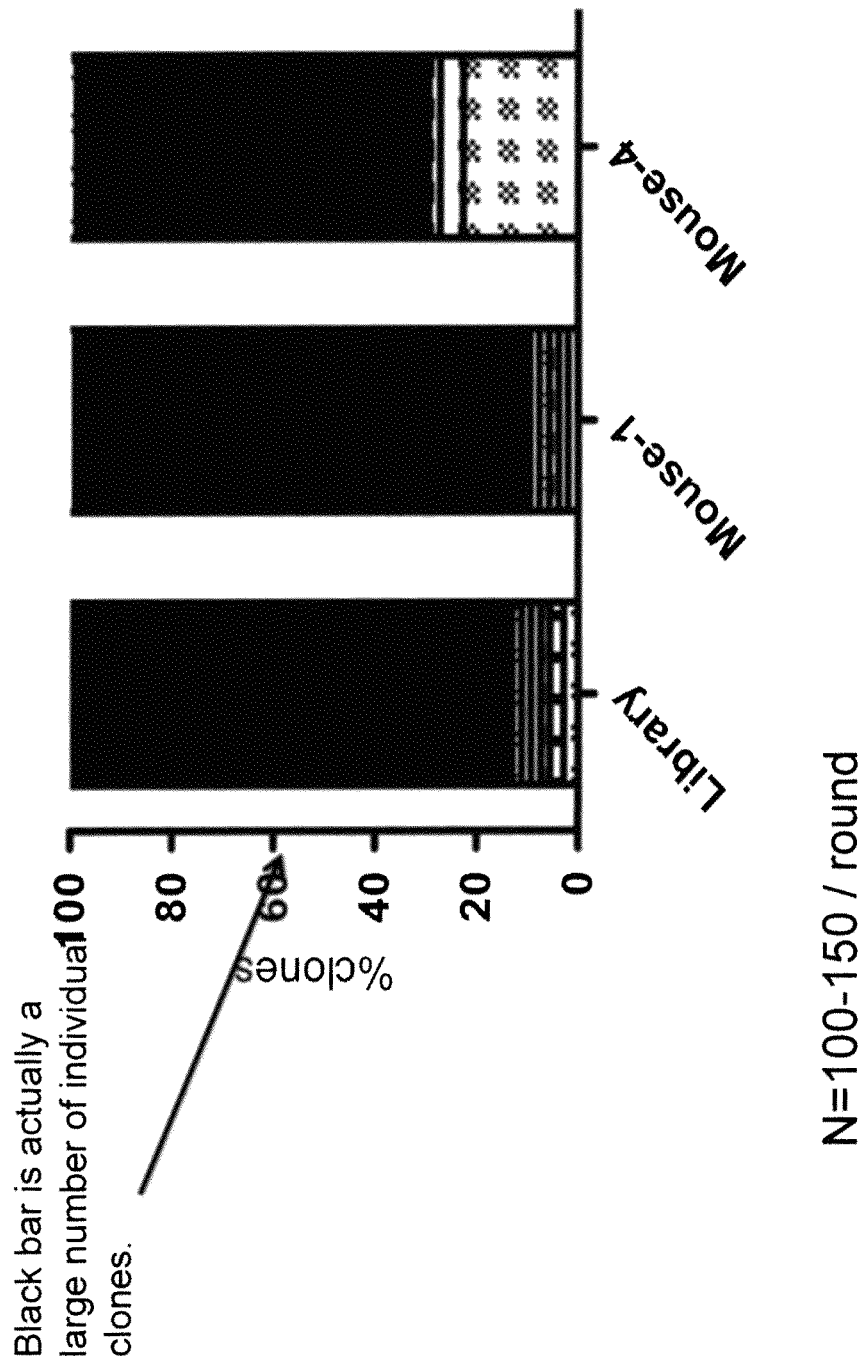
Figure 13. AAV shuffle library screening in FRG mice.

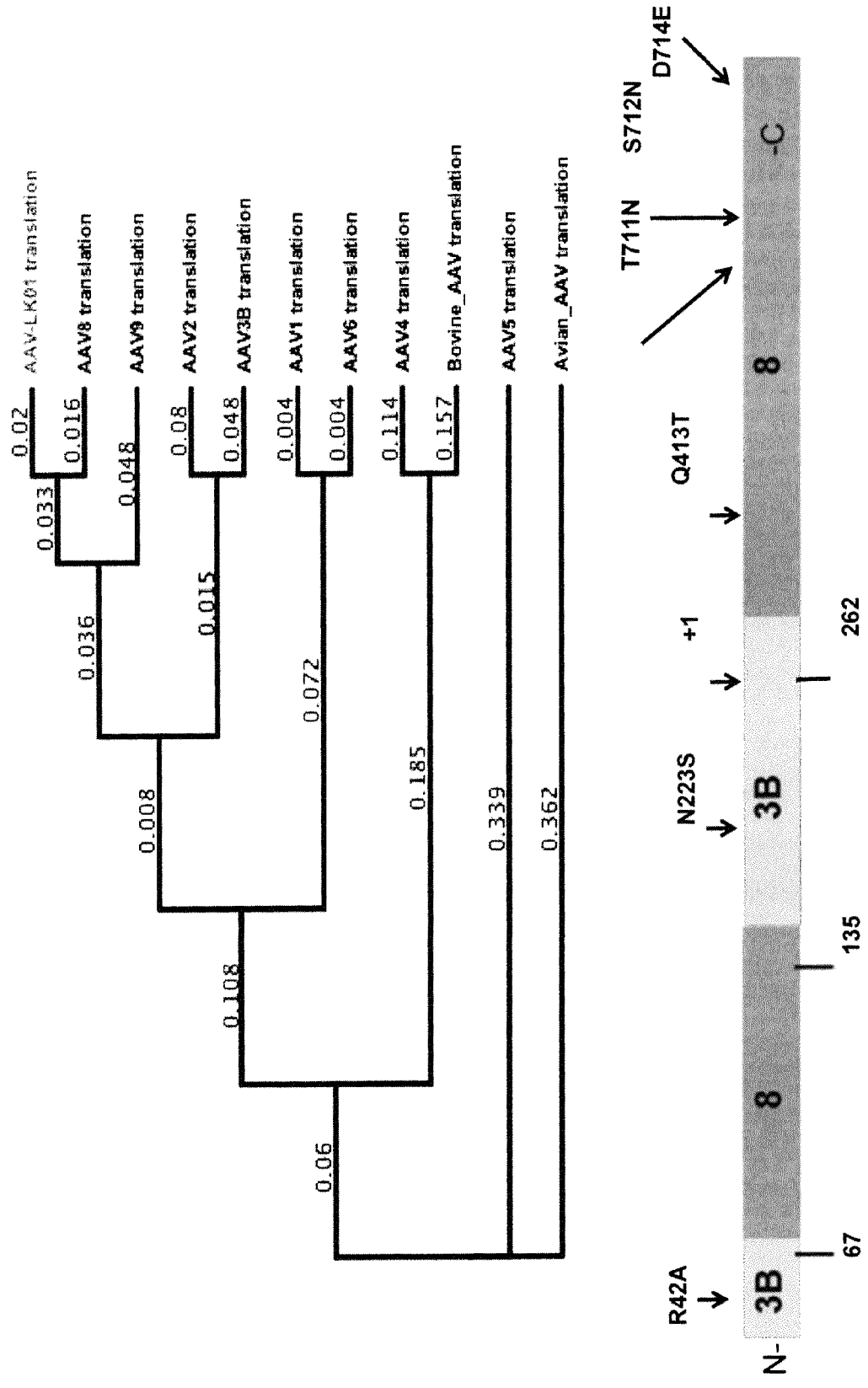
Figure 14. AAV shuffle library screening in FRG mice. AAV-LK01.

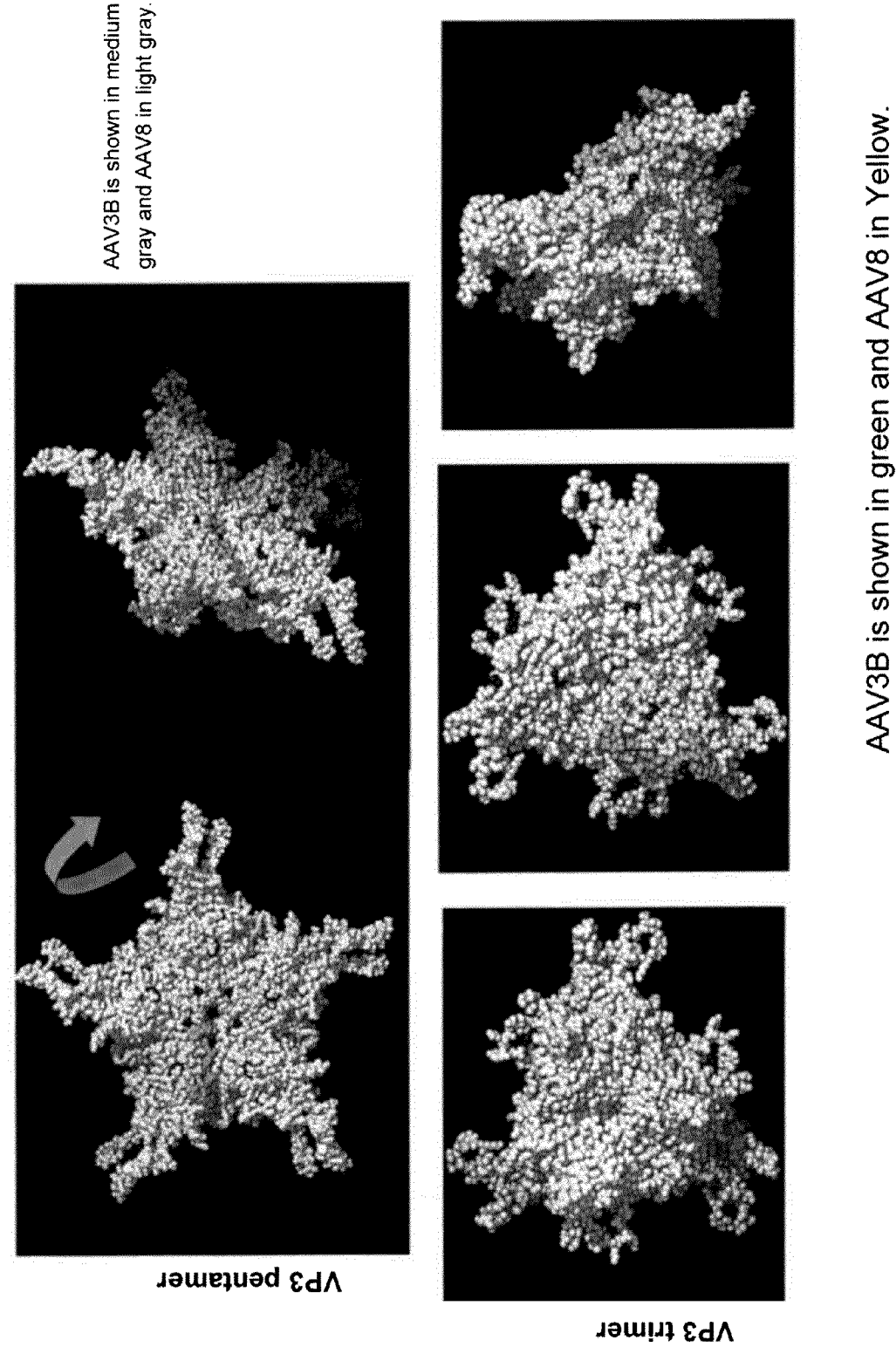
Figure 15. AAV shuffle library screening in FRG mice. Structural model of a VP3 subunit of AAV-LK01

Figure 16. AAV shuffle library screening in vitro and in FRG mice. AAV-PAEC and AAV-LK01 Heparin Binding.

| AAV2 | AAV-LK1 | AAV-PAEC |
|---|---|---|
| R475 | K (8) | P (1/6) |
| R484 | R (8) | Y (1/3/6) |
| R487 | R (8) | Q (1/3/6) |
| K532 | R (8) | D (1/6/8) |
| R585 | Q (8) | Q (1/3/6/Bovine) |
| R588 | T (8) | S (1/6/Avian) |

Comparison of residues implicated in heparin binding in AAV2 to residues in new AAVs. AAV sources of the amino acids in new AAVs at indicated positions are given in parenthesis.

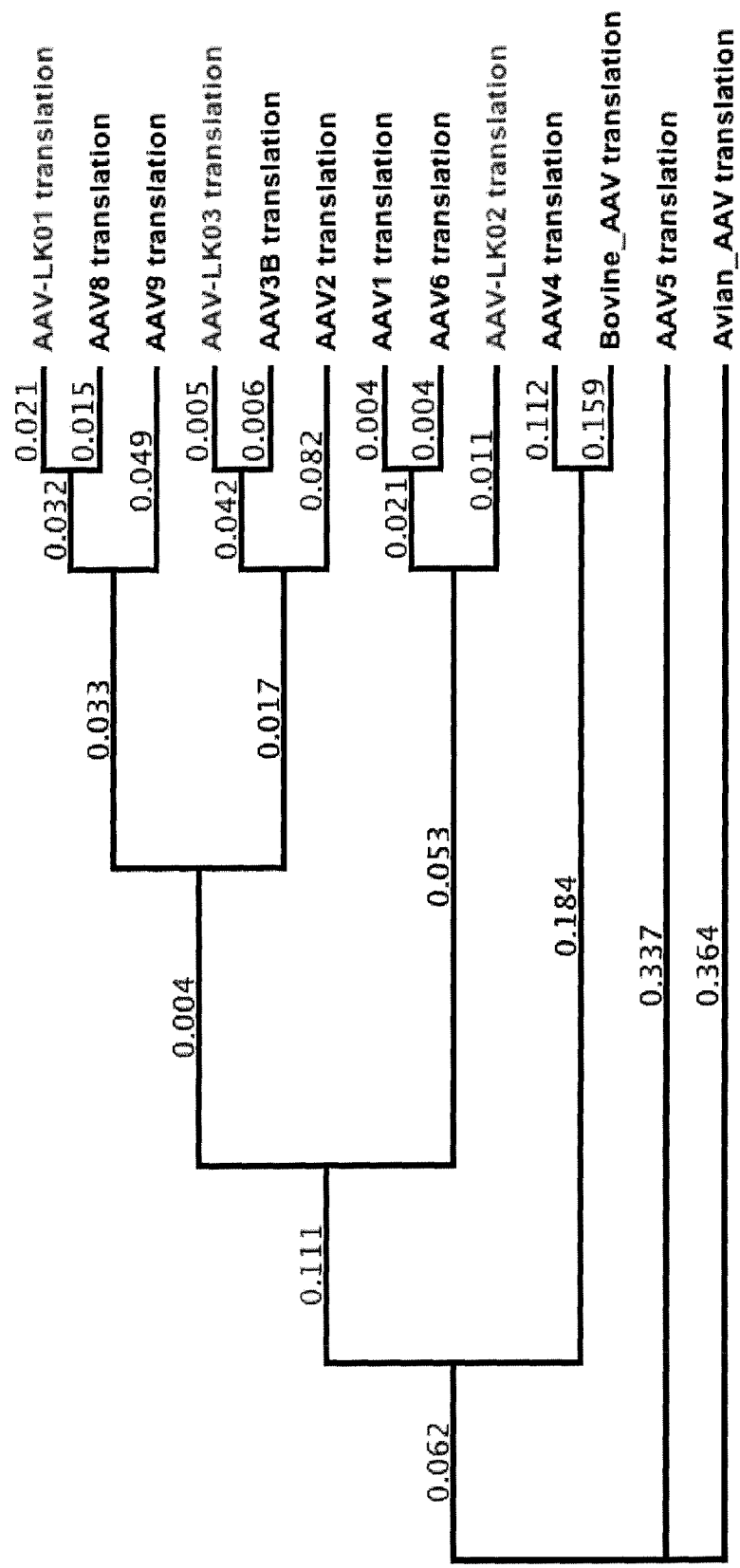
Figure 17. AAV shuffle library screening in FRG mice. Top 3 isolates.

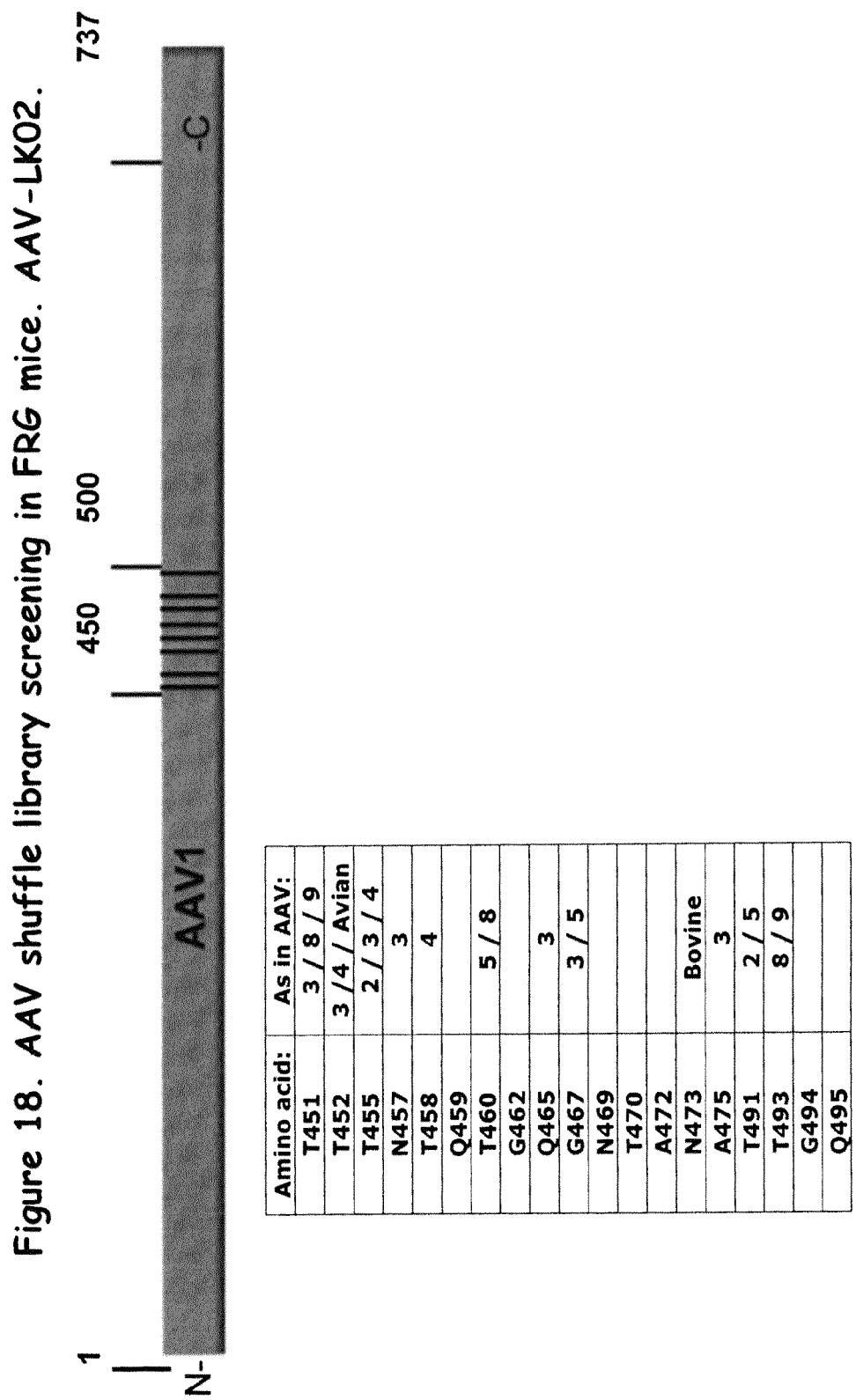
Figure 18. AAV shuffle library screening in FR6 mice. AAV-LK02.

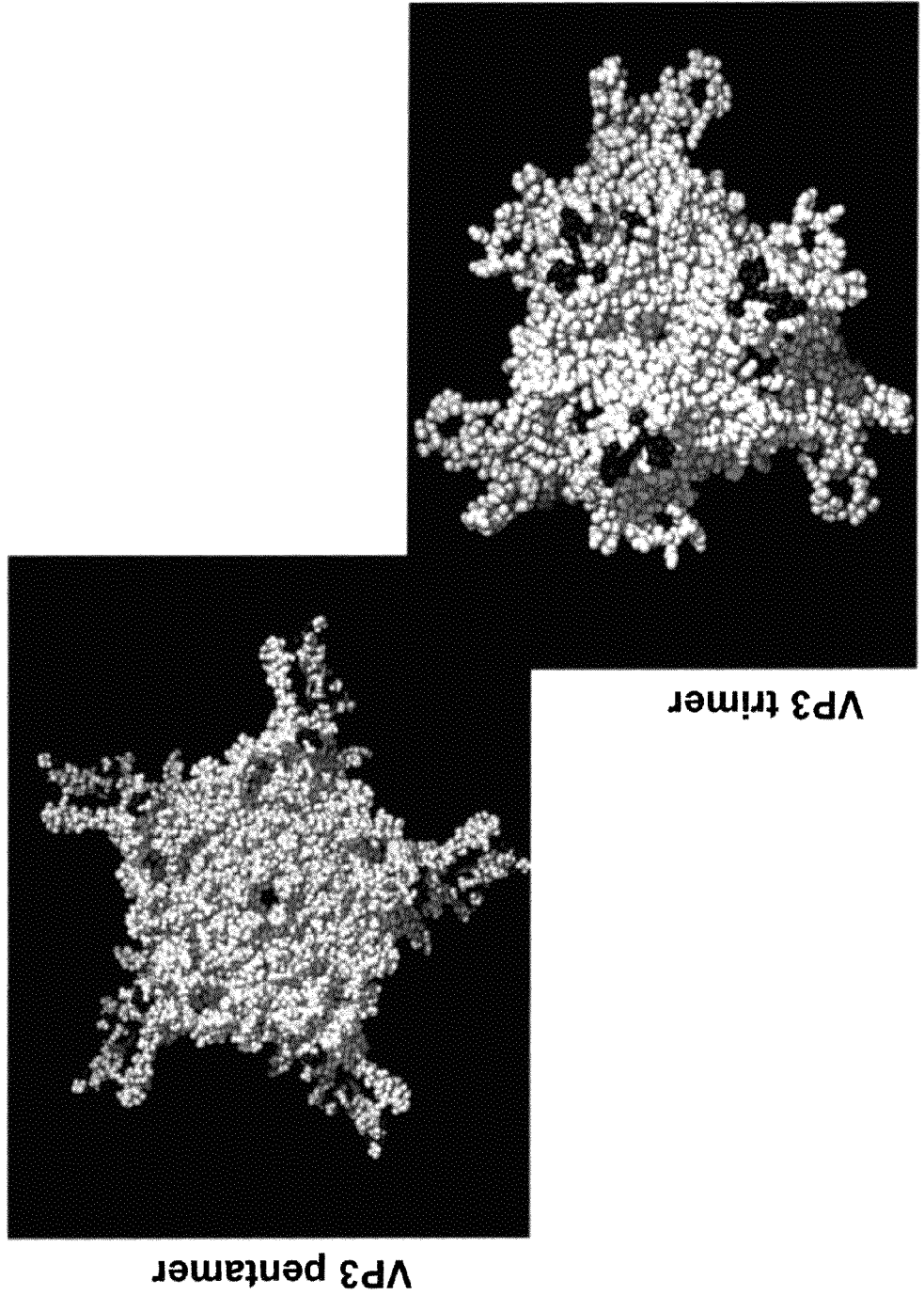
Figure 19. AAV shuffle library screening in FRG mice. Structural model of a VP3 subunit of AAV-LK02

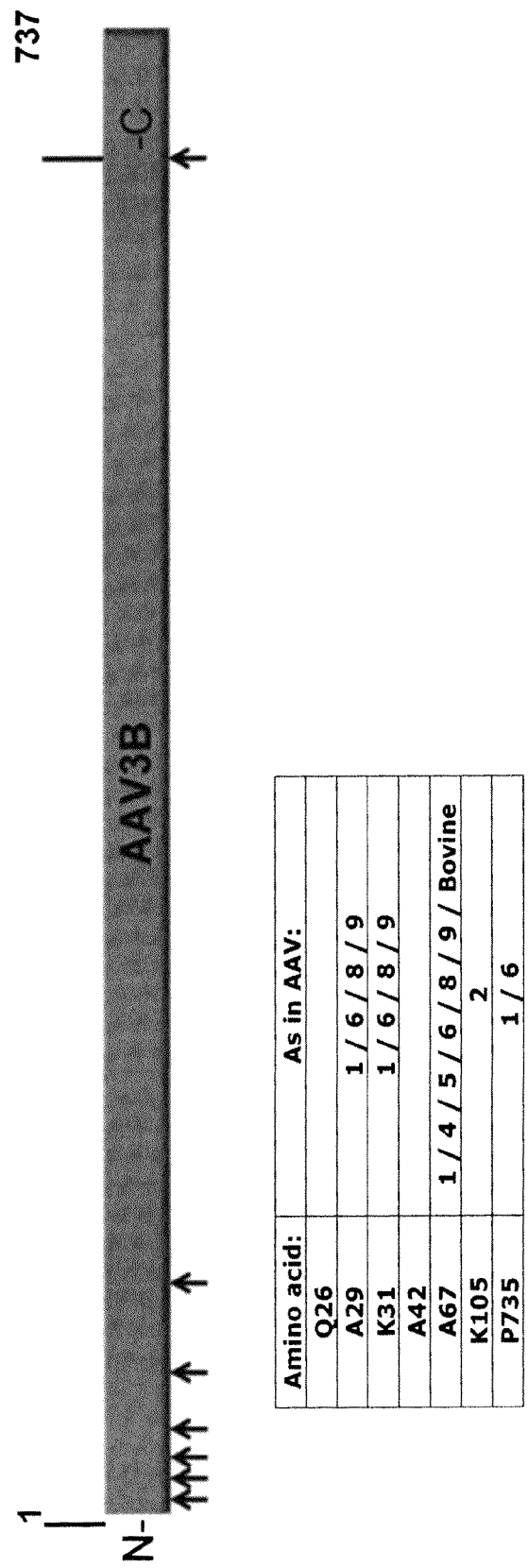
Figure 20. AAV shuffle library screening in FRG mice. AAV-LK03.

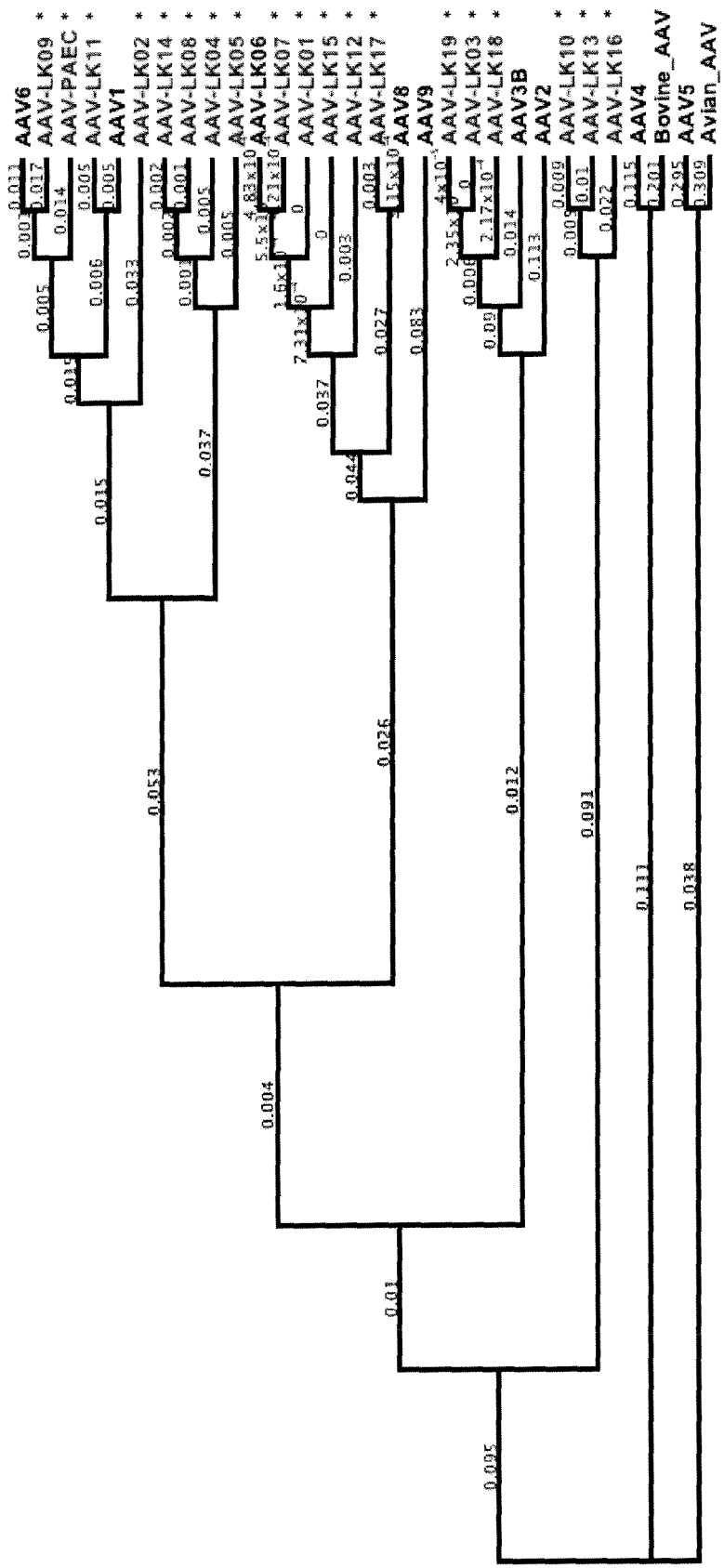
Figure 21. DNA sequence relatedness between selected AAVs (*) and wtAAVs

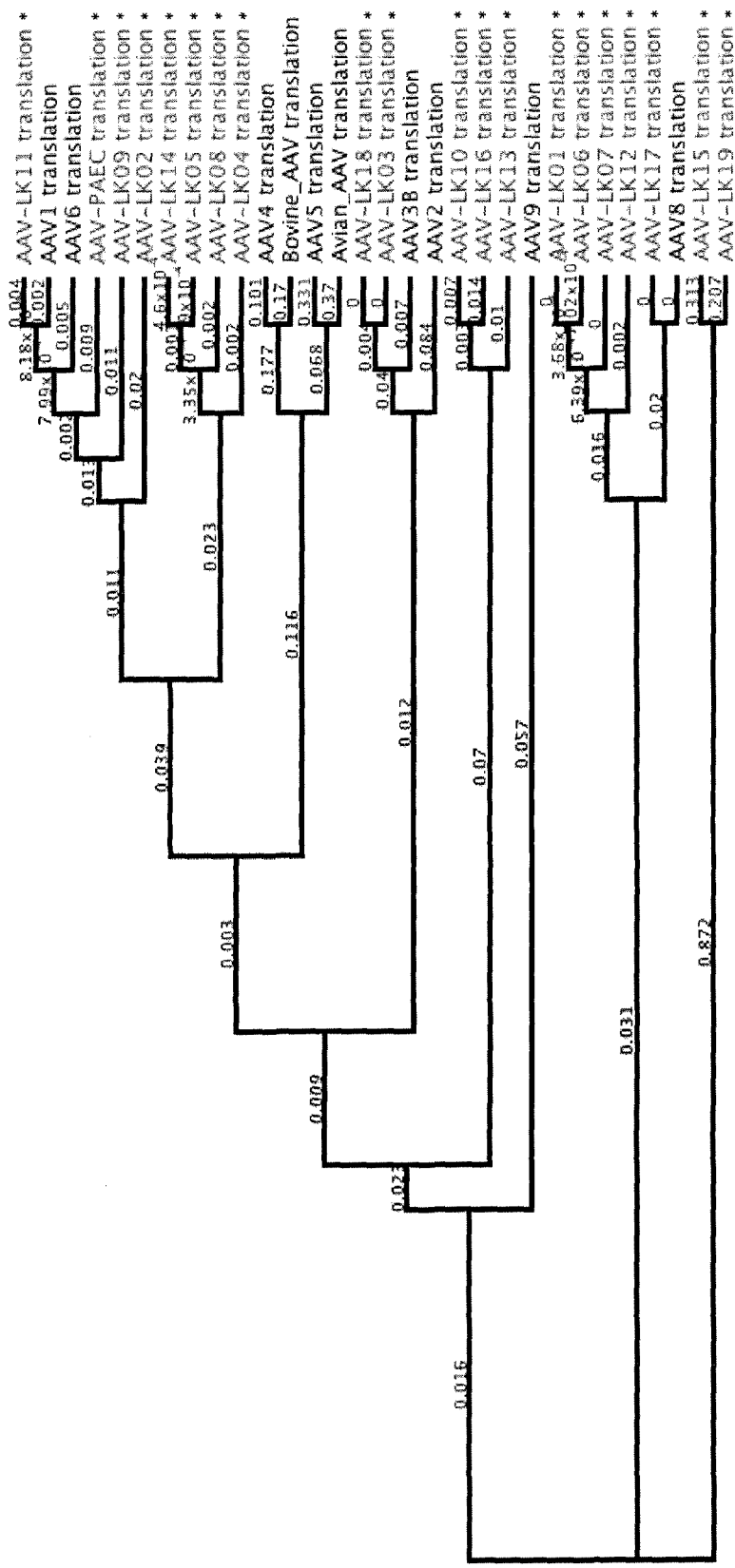
Figure 22. Amino acid sequence relatedness between selected AAVs (*) and wtAAVs

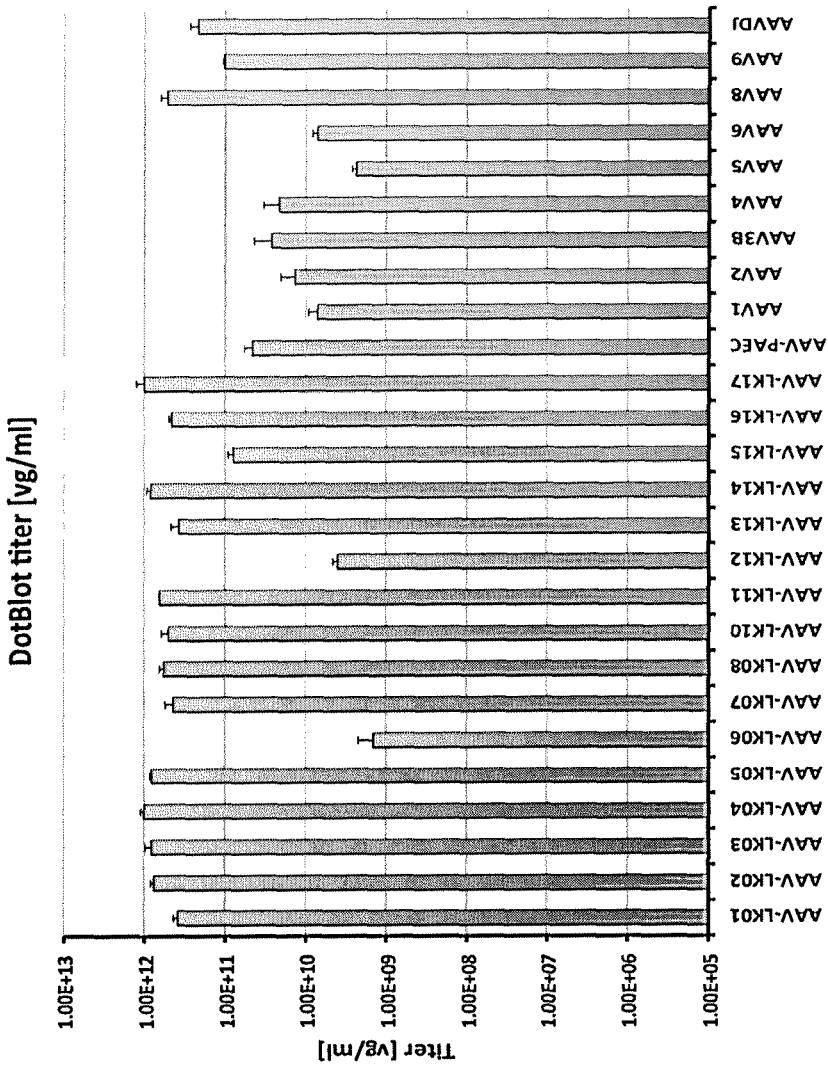
Figure 23A. Comparison of new AAV isolates and wtAAV. Dot Blot Titer.
Figure 23B. Comparison of new AAV isolates and wtAAV.

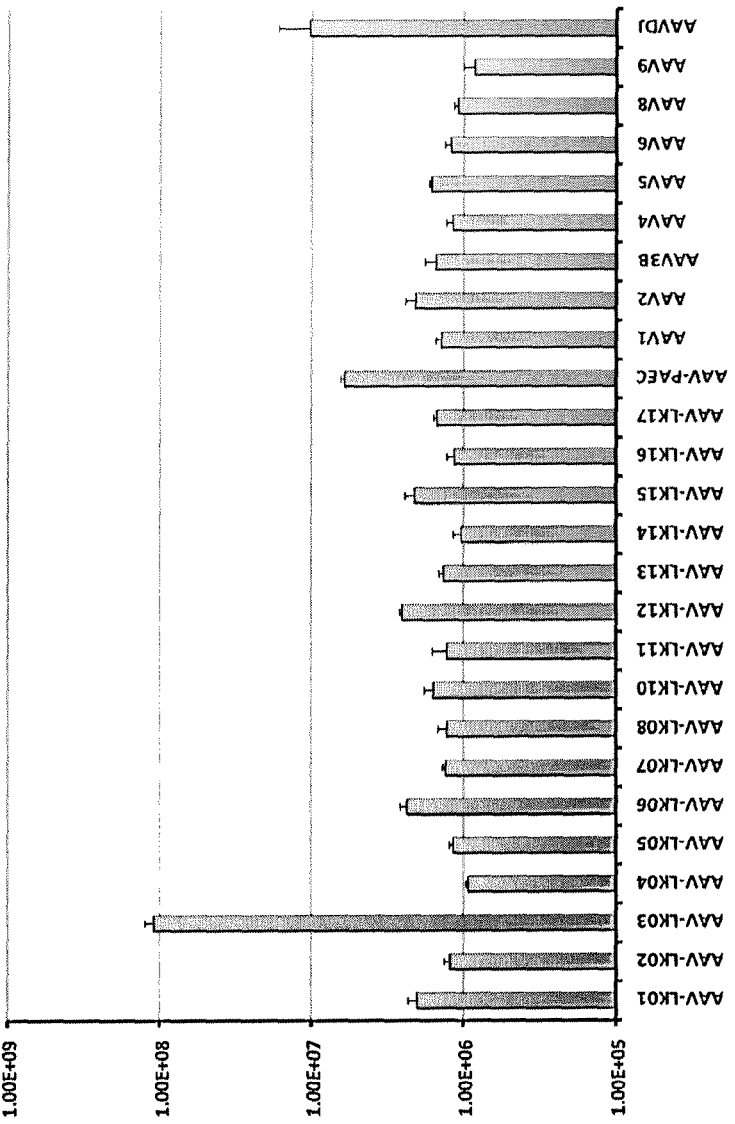
Figure 24A. Comparison of new AAV isolates and wtAAV. Transduction Titer on Huh7.5 cells.
Figure 24B. Comparison of new AAV isolates and wtAAV. AAV Transduction titer on Huh7.5 cells Figure 25A. Comparison of new AAV isolates and wtAAV. Transduction efficiency on Huh7.5 cells per AAV vector genome (vg).

| Vector | DotBlot titer [vg/ml] | Transduction vg/well | Transduction titer [IU/ml] | trans titer/vg | trans titer/vg normalized |
|---|---|---|---|---|---|
| AAV-LK01 | 7.44632E+11 | 7.45E+09 | 2.04E+06 | 0.000273356 | 2.950739054 |
| AAV-LK02 | 7.63456E+11 | 7.63E+09 | 1.23E+06 | 0.000160913 | 1.736970222 |
| AAV-LK03 | 8.23146E+11 | 8.23E+07 | 1.09E+08 | 1.327528594 | 14329.97187 |
| AAV-LK04 | 1.00388E+12 | 1.00E+10 | 9.30E+05 | 0.000092640 | 1.000002784 |
| AAV-LK05 | 8.07062E+11 | 8.07E+09 | 1.17E+06 | 0.000144784 | 1.562871385 |
| AAV-LK06 | 1429693637 | 1.43E+07 | 2.34E+06 | 0.163881264 | 1769.011914 |
| AAV-LK07 | 4.39393E+11 | 4.39E+09 | 1.31E+06 | 0.000297684 | 3.213339014 |
| AAV-LK08 | 5.76405E+11 | 5.76E+09 | 1.28E+06 | 0.000222760 | 2.404578032 |
| AAV-LK10 | 5.01822E+11 | 5.02E+09 | 1.59E+06 | 0.000316247 | 3.413723011 |
| AAV-LK11 | 6.44077E+11 | 6.44E+09 | 1.29E+06 | 0.000200054 | 2.159474583 |
| AAV-LK12 | 4050798638 | 4.05E+07 | 2.53E+06 | 0.062506193 | 674.721423 |
| AAV-LK13 | 3.76009E+11 | 3.76E+09 | 1.35E+06 | 0.000359034 | 3.875578066 |
| AAV-LK14 | 8.36847E+11 | 8.37E+09 | 1.04E+06 | 0.000123678 | 1.335043948 |
| AAV-LK15 | 793479996858 | 7.93E+08 | 2.10E+06 | 0.002644679 | 28.54791925 |
| AAV-LK16 | 4.58932E+11 | 4.59E+09 | 1.15E+06 | 0.000251345 | 2.7131327 |
| AAV-LK17 | 1.00746E+12 | 1.01E+10 | 1.50E+06 | 0.000148890 | 1.60718548 |
| AAV-PAEC | 457501963886 | 4.58E+07 | 6.05E+06 | 0.132130580 | 1426.280012 |
| AAV1 | 7148468185 | 7.15E+07 | 1.39E+06 | 0.019472703 | 210.1975744 |
| AAV2 | 135820895552 | 1.36E+08 | 2.08E+06 | 0.0152848355 | 164.991744 |
| AAV3B | 264493322286 | 2.64E+08 | 1.53E+06 | 0.005790316 | 62.50341435 |
| AAV4 | 214454045556 | 2.14E+08 | 1.19E+06 | 0.005525659 | 59.64658183 |
| AAV5 | 23828227728 | 2.38E+07 | 1.63E+06 | 0.068364297 | 737.9565706 |
| AAV6 | 7148468185 | 7.15E+07 | 1.22E+06 | 0.016996648 | 183.4698656 |
| AAV8 | 5.19932E+11 | 5.20E+09 | 1.09E+06 | 0.000210316 | 2.2702504 |
| AAV9 | 1.03415E+11 | 1.03E+09 | 8.49E+05 | 0.000820968 | 8.861917046 |
| AAVDJ | 2.21364E+11 | 2.21E+08 | 1.04E+07 | 0.046789402 | 505.0669466 |

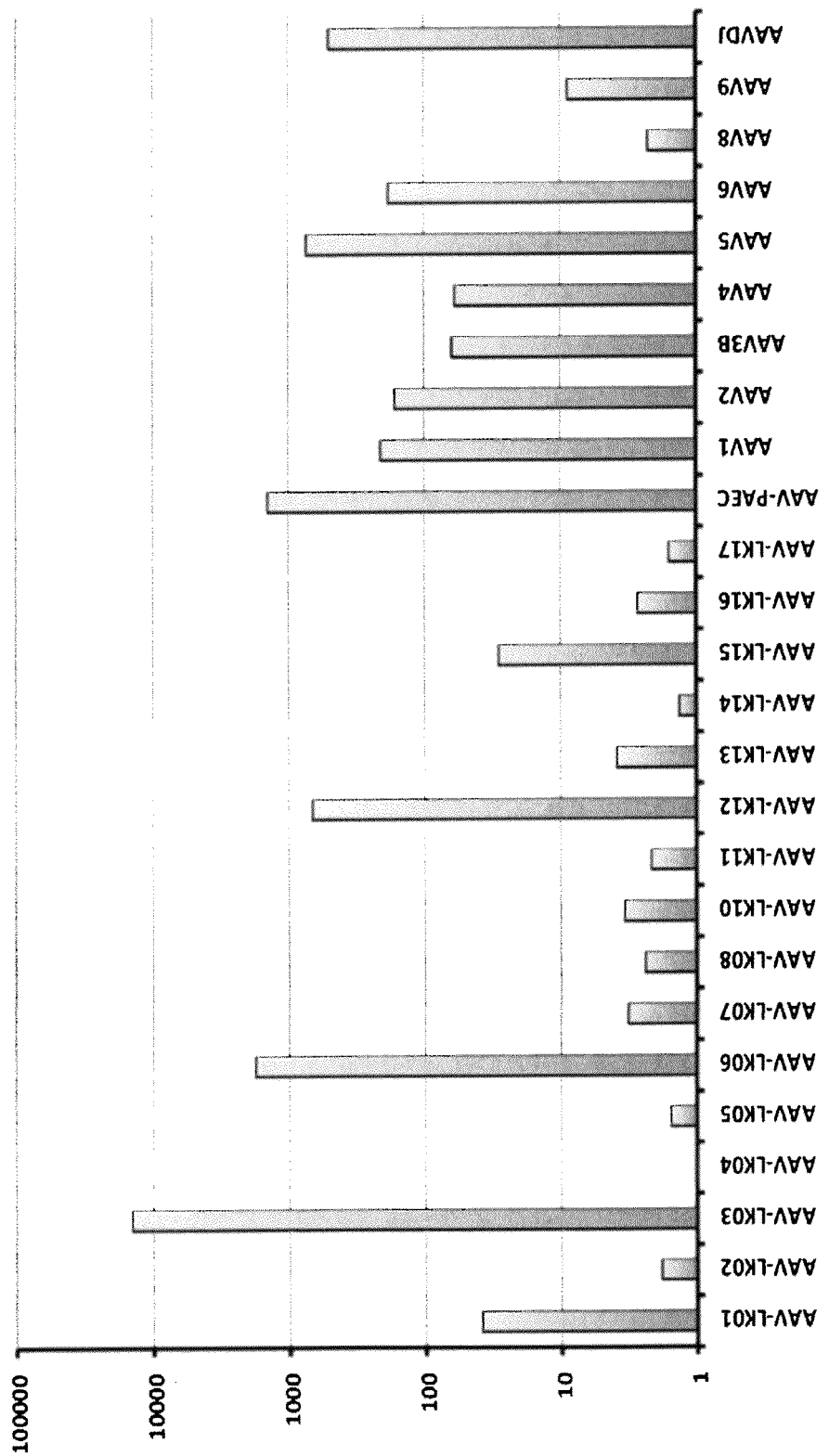
Figure 25B. Comparison of new AAV isolates and wtAAV. Transduction efficiency on Huh7.5 cells per AAV vector genome (vg). Huh7.5 Cells. Transduction titer / vg [normalized the the lowest - AAV-LK04]

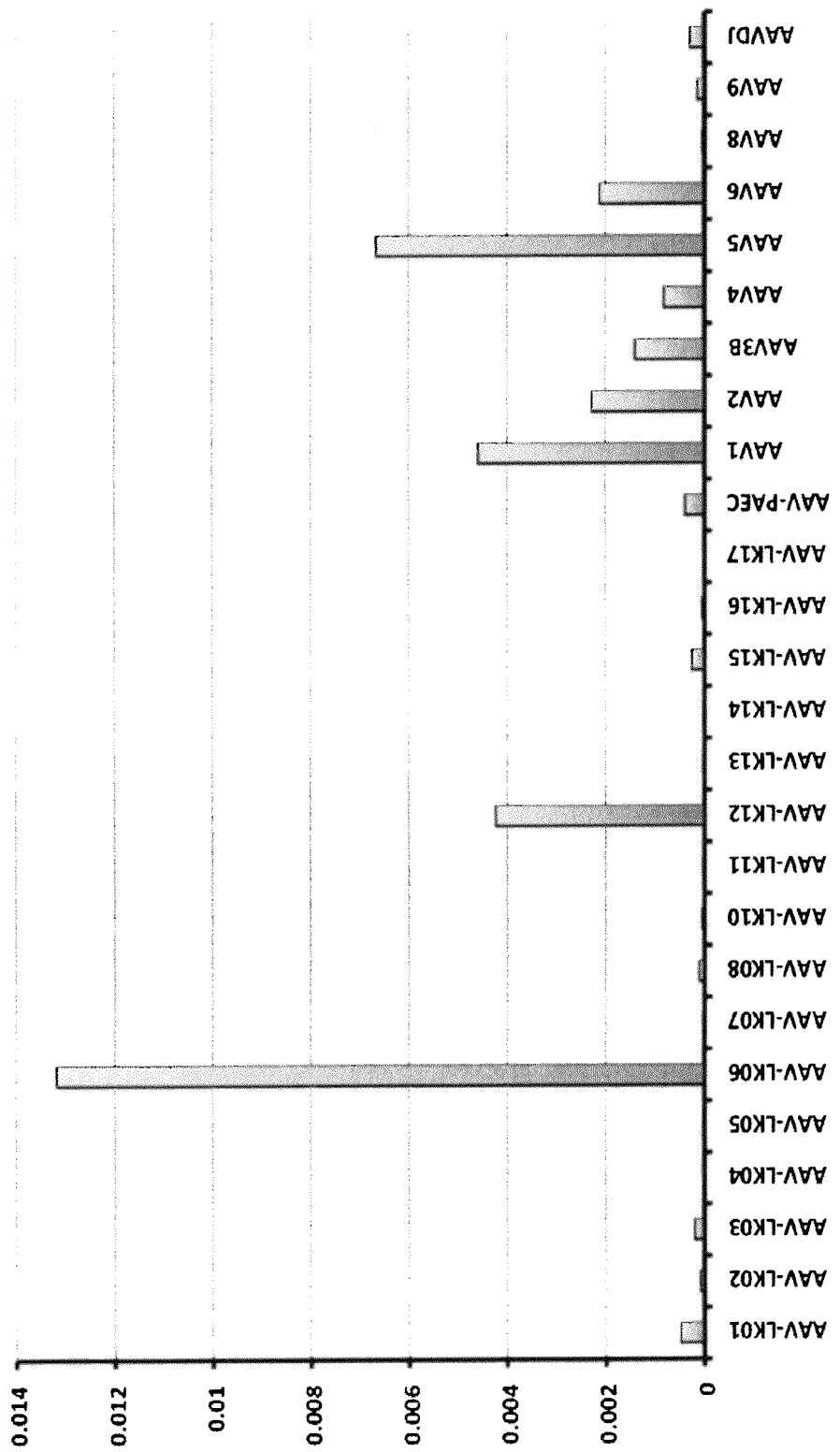
Figure 26. Comparison of new AAV isolates and wtAAV. Transduction efficiency on 293 cells per AAV vector genome (vg). 293 cells. Transduction titer / vg

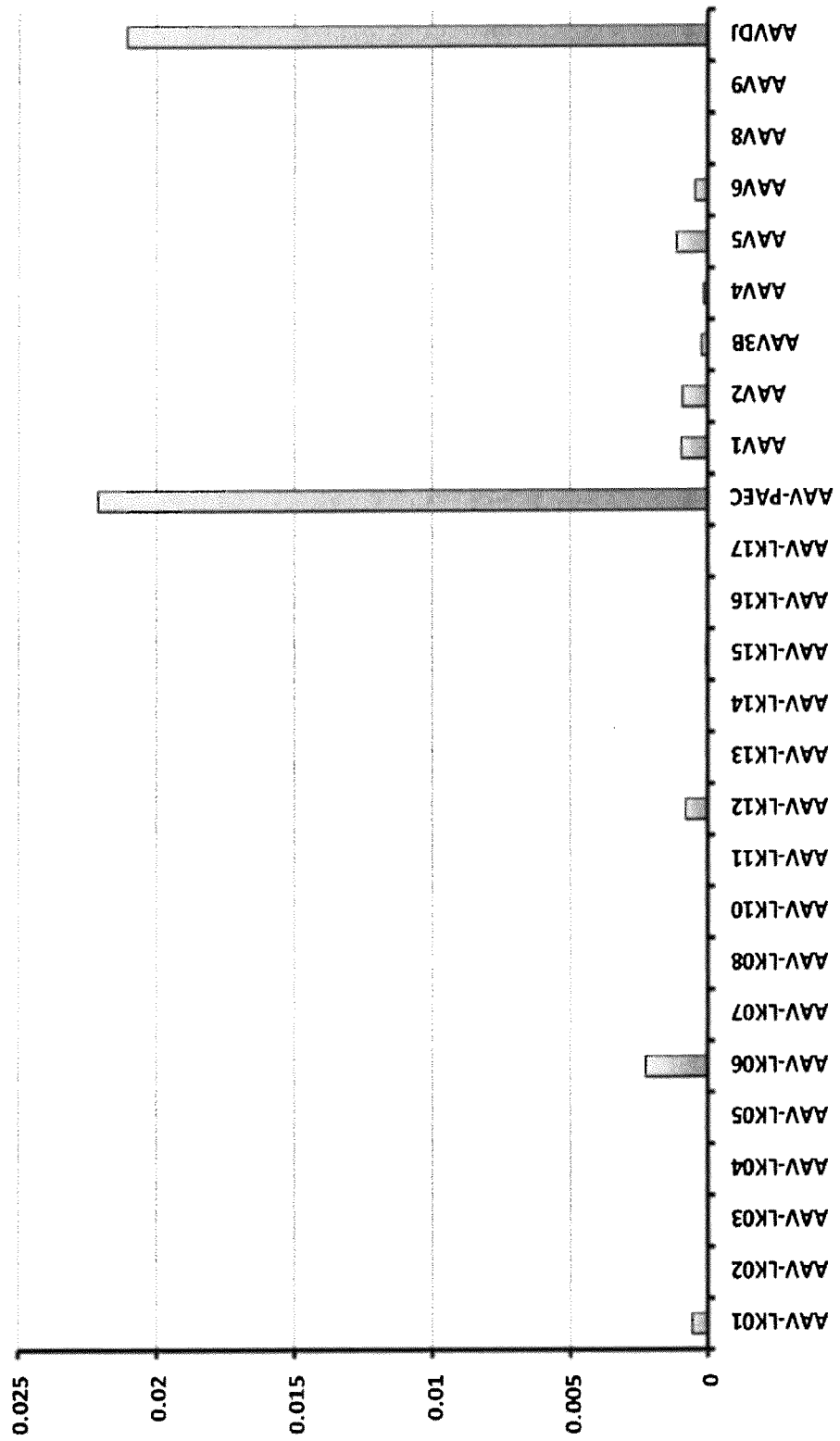
Figure 27. Comparison of new AAV isolates and wtAAV. Transduction efficiency on NIH3T3 cells per AAV vector genome (vg). 3T3 Cells. Transduction titer / vg

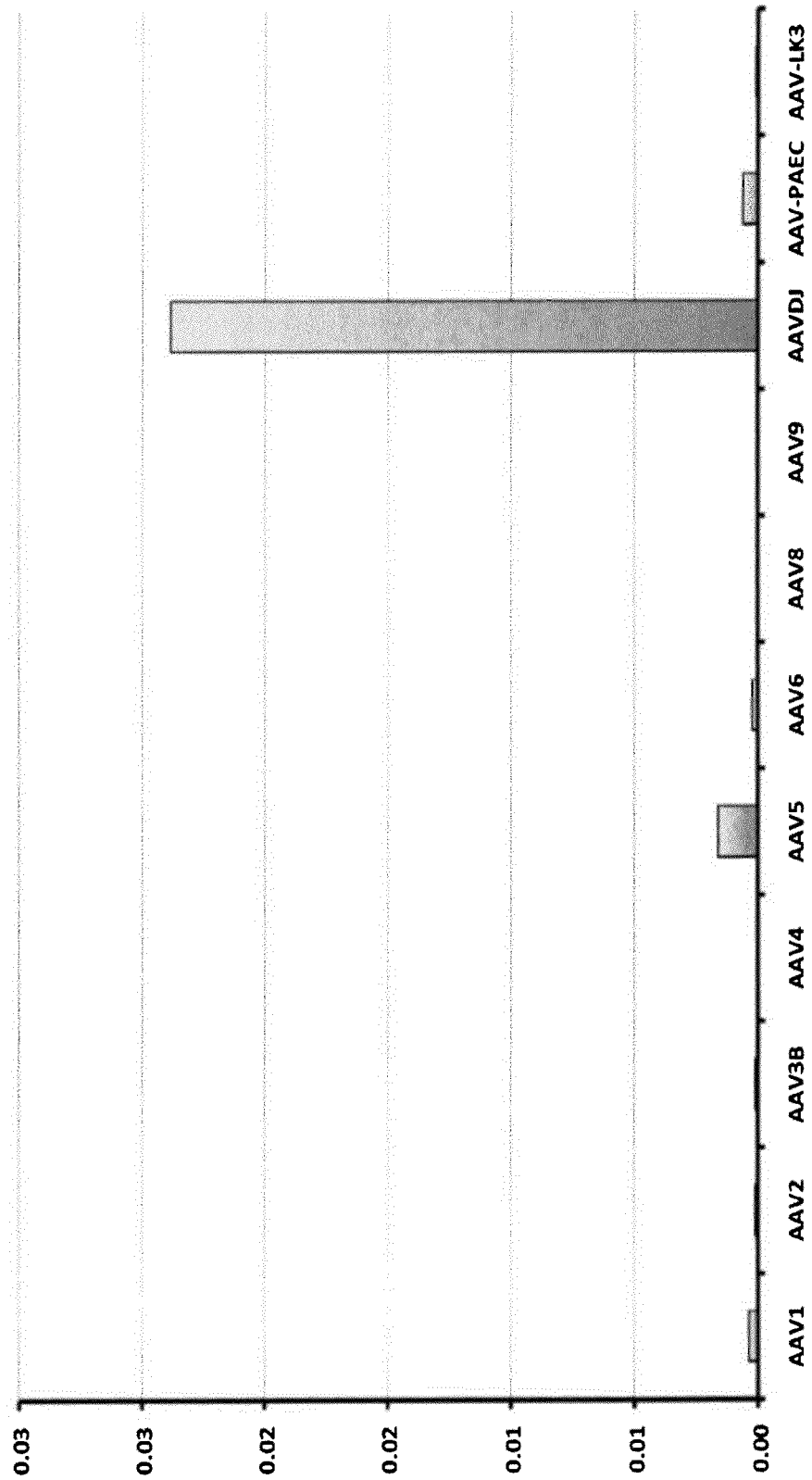
Figure 28. Comparison of selected AAV isolates and wtAAV. Transduction efficiency on MEF cells per AAV vector genome (vg). MEF Cells. Transduction titer / vg Dot Blot titer [vg/ml]

Figure 30. Neutralization by Hepatocyte Growth Factor

Figure 31. Transduction of Primary Human Hepatocytes

Human FIX expression in C57/BL6 mice in vivo

Neutralization by human pooled IgG (IVIG)

Figure 46.

Relative transduction of AAV serotypes in different cell lines

| Cells: | Species: | Origin: | AAV1 | AAV2 | AAV3B | AAV4 | AAV5 | AAV6 | AAV8 | AAV9 | AAVDJ | AAVLK01 | AAVLK02 | AAVLK03 | AAVLK19 | PAEC |
|---|---|---|---|---|---|---|---|---|---|---|---|---|---|---|---|---|
| Hela | Human | Epithelial | 1.41E+01 | 4.70E+02 | 1.78E+02 | 4.25E+00 | 1.14E+02 | 9.51E+01 | 1.86E+00 | 1.00E+00 | 1.32E+03 | 1.26E+00 | 1.05E+00 | 1.61E+03 | 1.68E+02 | 7.47E+00 |
| PAEC | Human | Endothelial | 9.94E+01 | 3.84E+01 | 1.95E+01 | 5.18E+01 | 3.47E+02 | 1.08E+02 | 3.38E+00 | 1.16E+01 | 8.11E+01 | 1.04E+01 | 1.00E+00 | 8.36E+02 | 6.16E+01 | 1.37E+01 |
| Huh7 | Human | Hepatocytes | 1.69E+01 | 6.57E+02 | 3.32E+01 | 8.82E+00 | 5.92E+01 | 1.84E+01 | 5.76E+00 | 1.98E+00 | 1.38E+03 | 1.77E+00 | 1.70E+00 | 1.42E+03 | 1.06E+03 | 2.34E+01 |
| Primary Keratinocytes | Human | Keratinocytes | 9.41E+01 | 1.90E+02 | 4.78E+01 | 3.41E+01 | 7.56E+01 | 1.09E+02 | 2.17E+00 | 5.57E+00 | 1.63E+01 | 5.63E+00 | 1.48E+00 | 1.57E+02 | 8.23E+02 | 1.23E+01 |
| Primary Hepatocytes | Human | Hepatocytes | NA | 2.50E+01 | 5.00E+01 | NA | NA | NA | 5.00E+00 | NA | 1.00E+02 | 1.00E+00 | 1.00E+00 | 5.00E+02 | 4.00E+01 | NA |
| FRhK-4 | Rhesus monkey | Epithelial | 1.21E+02 | 5.60E+02 | 1.02E+02 | 5.27E-01 | 4.01E+01 | 6.69E+01 | 1.66E+01 | 1.03E+01 | 8.47E+01 | 6.57E+00 | 1.00E+00 | 8.29E+01 | 4.21E+01 | 5.87E+01 |
| MEF | Mouse | Fibroblasts | 3.30E+02 | 2.10E+02 | 9.43E+00 | 1.23E+01 | 3.62E+02 | 1.95E+01 | 1.14E+02 | 1.64E+01 | 1.79E+04 | 1.30E+01 | 2.95E+01 | 4.33E+01 | 1.06E+02 | 2.17E+02 |
| 3T3 | Mouse | Fibroblasts | 1.40E+02 | 1.94E+03 | 4.93E+00 | 2.52E+01 | 1.55E+02 | 1.63E+01 | 1.52E+02 | 2.59E+02 | 7.63E+04 | 2.17E+01 | 4.88E+01 | 1.50E+01 | 1.86E+02 | 3.74E+02 |
| H4TG | Rat | Hepatocytes | 3.18E+02 | 9.52e2 | 3.68E+01 | 3.89E-01 | 7.34E+02 | 2.68E+02 | 2.64E+02 | 6.33E+01 | 1.61E+04 | 4.60E+01 | 6.60E+01 | 7.70E+00 | 1.59E+01 | 9.28E+02 |
| LMH | Chicken | Hepatocytes | 9.77E+01 | 3.50E+01 | 5.11E+01 | 1.82E+01 | 1.15E+01 | 1.19E+02 | 4.44E+00 | 1.08E+01 | 1.54E+01 | 7.28E+00 | 1.00E+00 | 1.06E+02 | 1.69E+02 | 3.85E+01 |

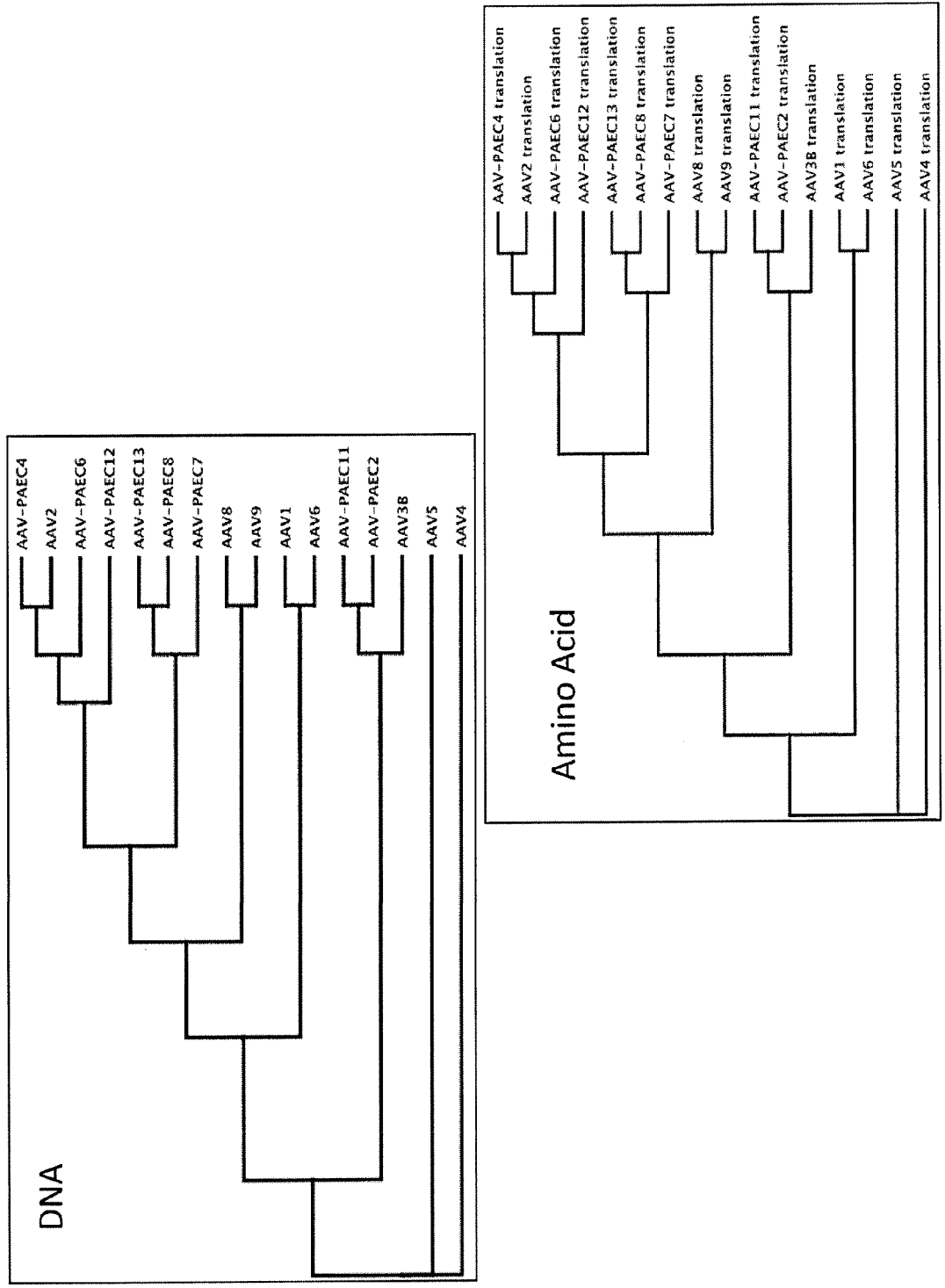
Figure 47. New AAV isolates obtained on human PAEC cells.

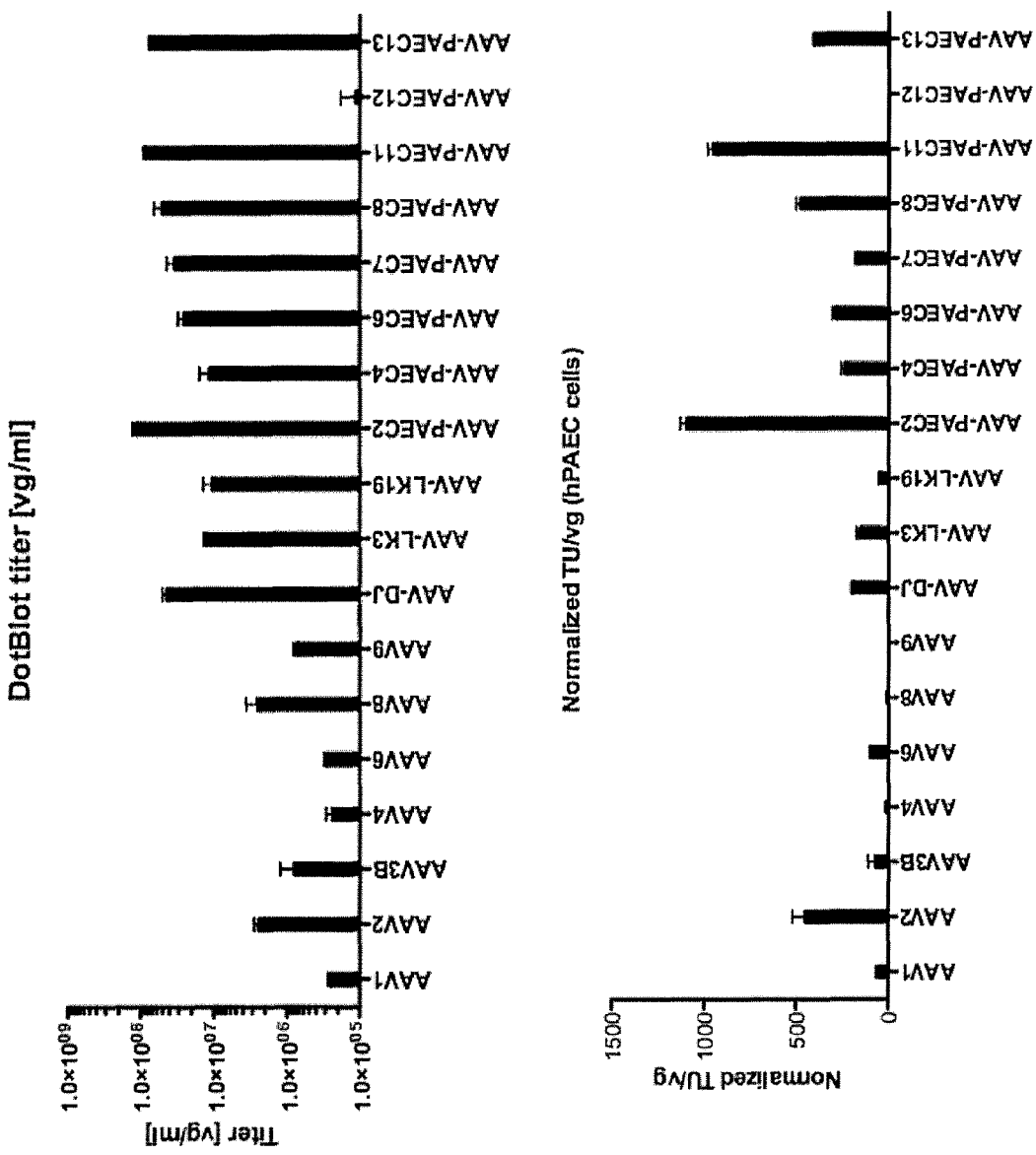
Figure 48. Comparison of new AAV-PAEC and wtAAVs. Titer and transduction of hPAEC cells.

SEQUENCE LISTING

```
<160> NUMBER OF SEQ ID NOS: 56

<210> SEQ ID NO 1
<211> LENGTH: 2211
<212> TYPE: DNA
<213> ORGANISM: Artificial sequence
<220> FEATURE:
<223> OTHER INFORMATION: Recombinant sequence

<400> SEQUENCE: 1
atggctgctg acggttatct tccagattgg ctcgaggaca acctttctga aggcattcgt      60
gagtggtggg ctctgaaacc tggagtccct caacccaaag cgaaccaaca acaccaggac     120
aaccgtcggg gtcttgtgct tccgggttac aaatacctcg gacccggtaa cggactcgac     180
aaaggagagc ccgtcaacgc ggcggatgca gcggccctcg agcacgacaa ggcctacgac     240
cagcagctca aagcgggtga caatccgtac ctgcggtata ccacgccga cgccgagttt     300 caggagcgtc tgcaagaaga tacgtctttt gggggcaacc tcgggcgagc agtcttccag     360
gccaagaaga gggttctcga acctttggt ctggttgagg aagtgctaa gacggctcct     420 ggaaagaaac gtccggtaga gcagtcgcca caagagccag actcctcctc gggcatcggc     480
aagacaggcc agcagcccgc taaaaagaga ctcaattttg gtcagactgg cgactcagag     540 tcagtcccg acccacaacc tctcggagaa cctccagcaa cccccgctgc tgtgggacct     600
actacaatgg cttcaggcgg tggcgcacca atggcagaca ataacgaagg cgccgacgga     660
gtgggtaatg cctcaggaaa ttggcattgc gattccacat ggctgggcga cagagtcatc     720
accaccagca cccgcacctg ggccttgccc acctacaata accacctcta caagcaaatc     780
tccagtgctt caacggggc cagcaacgac aaccactact cggctacag cacccctgg     840 gggtattttg atttcaacag attccactgc catttctcac cacgtgactg gcagcgactc     900
atcaacaaca attggggatt ccggcccaag agactcaact tcaagctctt caacatccaa     960
gtcaaggagg tcacgacgaa tgatggcgtc acgaccatcg ctaataacct taccagcacg    1020
gttcaagtct ctctcggactc ggagtaccag cttccgtacg tcctcggctc tgcgcaccag    1080
ggctgcctcc ctccgttccc ggcggacgtg ttcatgattc cgcaatacgg ctacctgacg    1140
ctcaacaatg gcagccaagc cgtgggacgt tcatcctttt actgcctgga atatttccct    1200
tctcagatgc tgagaacggg caacaacttt accttcagct cacctttga ggaagtgcct    1260 ttccacagca gctacgcgca cagccagagc ctggaccggc tgatgaatcc tctcatcgac    1320
caatacctgt attacctgaa cagaactcaa aatcagtccg gaagtgccca aaacaaggac    1380
ttgctgttta gccgtgggtc tccagctggc atgtctgttc agcccaaaaa ctggctacct    1440
ggaccctgtt atcggcagca gcgcgtttct aaaacaaaaa cagacaacaa caacagcaat    1500
tttacctgga ctggtgcttc aaaatataac ctcaatgggc gtgaatccat catcaaccct    1560
ggcactgcta tggcctcaca caaagacgac gaagacaagt tctttcccat gagcggtgtc    1620
atgatttttg gaaaagagag cgccggagct tcaaacactg cattggacaa tgtcatgatt    1680
```

```
acagacgaag aggaaattaa agccactaac cctgtggcca ccgaaagatt tgggaccgtg    1740
gcagtcaatt tccagagcag cagcacagac cctgcgaccg gagatgtgca tgttatggga    1800
gccttacctg gaatggtgtg gcaagacaga gacgtatacc tgcagggtcc tatttgggcc    1860
aaaattcctc acacgatgg acactttcac ccgtctcctc tcatgggcgg ctttggactt    1920
aagcacccgc tcctcagat cctcatcaaa aacacgcctg ttcctgcgaa tcctccggca    1980
gagttttcgg ctacaaagtt tgcttcattc atcacccagt attccacagg acaagtgagc    2040
gtggagattg aatgggagct gcagaaagaa aacagcaaac gctggaatcc cgaagtgcag    2100
tatacatcta actatgcaaa atctgccaac gttgatttca ctgtggacaa caatggactt    2160
tatactgagc ctcgccccat tggcacccgt tacctcaccc gtccctgta a              2211

<210> SEQ ID NO 2
<211> LENGTH: 2214
<212> TYPE: DNA
<213> ORGANISM: Artificial sequence
<220> FEATURE:
<223> OTHER INFORMATION: Recombinant sequence

<400> SEQUENCE: 2
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaataccttg acccggcaa cggactcgac      180 aagggggagc cggtcaacgc agcagacgcg gcggccctcg agcacgacaa ggcctacgac     240
cagcagctgc aggcgggtga caatccgtac ctgcggtata accacgccga cgccgagttt     300
caggagcgtc tgcaagaaga tacgtctttt ggggggcaacc ttggcagagc agtcttccag    360
gccaaaaaga ggatccttga gcctcttggt ctggttgagg aagcagctaa aacggctcct     420
ggaagaagaa ggcctgtaga tcagtctcct caggaaccgg actcatcatc tggtgttggc     480
aaatcgggca acagcctgc cagaaaaaga ctaaatttcg gtcagactgg cgactcagag     540
tcagtcccag accctcaacc tctcggagaa ccaccagcag ccccacaag tttgggatct     600 aatacaatgg cttcaggcgg tggcgcacca atgcagacaa taacgagggg tgccgatggg    660
gtgggtagtt cctcgggaaa ttggcattgc gattcccaat ggctggggga cagagtcatc    720
accaccagca cccgaacctg ggccctgccc cctacaacaa tcacctctta aagcaaatc     780 tccaacggga catcggagg agccaccaac gacaacacct acttcggcta cagcaccccc    840
tgggggtatt ttgactttaa cagattccac tgccactttt caccacgtga ctggcagcga    900
ctcatcaaca caactgggg attccggccc aagagactca gcttcaagct cttcaacatc    960
caggtcaagg aggtcacgca gaatgaaggc accaagacca tcgccaataa cctcaccagc   1020
accatccagg tgtttacgga ctcggagtac cagctgccgt acgttctcgg ctctgcgcac   1080
cagggctgcc tccctccgtt cccggcgac gtgttcatga ttccgcaata cggctacctg   1140
acgctcaaca atggcagcca agccgtggga cgttcatcct tttactgcct ggaatatttc   1200
ccttctcaga tgctgagaac gggcaacaac tttaccttca gctacacctt tgaggaagtg   1260
cctttccaca gcagctacgc gcacagccag agccttgacc ggctgatgaa tcctctgatt   1320
gaccagtacc tgtactactt gtctcggact caaacaacag gaggcacggc aaatacgcag   1380
actctgggct tcagccaagg tgggcctaat acaatggcca atcaggcaaa gaactggctg   1440
ccaggacccc gttaccgcca acaacgcgtc tcaacgacaa ccgggcaaaa caacaatagc   1500
aactttgcct ggactgctgg gaccaaatac catctgaatg gaagaaattc attggctaat   1560
```

```
cctggcatcg ctatggcaac acacaaagac gacgaggagc gttttttcc cagtaacggg      1620 atcctgattt ttggcaaaca aaatgctgcc agagacaatg cggattacag cgatgtcatg      1680
ctcaccagcg aggaagaaat caaaaccact aaccctgtgg ctacagagga atacggtatc      1740
gtggcagata acttgcagca gcaaaacacg gctcctcaaa ttggaactgt caacagccag      1800
ggggccttac ccggtatggt ctggcagaac cgggacgtgt acctgcaggg tcccatctgg      1860
gccaagattc tcacacggga cggcaacttc cacccgtctc cgctgatggg cggctttggc      1920
ctgaaacatc ctccgcctca gatcctgatc aagaacacgc ctgtacctgc ggatcctccg      1980
accaccttca accagtcaaa gctgaactct ttcatcacgc aatacagcac cggacaggtc      2040
agcgtggaga tcgagtggga gctgcagaag gaaaacagca agcgctggaa cccggagatc      2100
cagtacactt ccaactatta caagtctaat aatgttgaat ttgctgttaa tactgaaggt      2160
gtatatagtg aaccccgccc cattggcacc agatacctga ctcgtaatct gtaa           2214
```

<210> SEQ ID NO 3
<211> LENGTH: 2211
<212> TYPE: DNA
<213> ORGANISM: Artificial sequence
<220> FEATURE:
<223> OTHER INFORMATION: Recombinant sequence

<400> SEQUENCE: 3

```
atggctgccg atggttatct tccagattgg ctcgaggaca acctctctga gggcattcgc        60
gagtggtggg acttgaaacc tggagccccg aagcccaaag ccaaccagca aaagcaggac       120
gacggccggg gtctggtgct tcctggctac aagtacctcg gacccttcaa cggactcgac       180 aaggggagc ccgtcaacgc ggcggacgca gcggccctcg agcacgacaa ggcctacgac       240
cagcagctca aagcgggtga caatccgtac ctgcggtata ccacgccga cgccgagttt       300 caggagcgtc tgcaagaaga tacgtctttt gggggcaacc tcgggcgagc agtcttccag       360
gccaagaagc gggttctcga acctctcggt ctggttgagg aaggcgctaa gacggctcct       420
ggaaagaaac gtccggtaga gcagtcgcca aagagccag actcctcctc gggcatcggc       480
aagacaggcc agcagcccgc taaaaagaga ctcaattttg gtcagactgg cgactcagag       540
tcagtccccg acccacaacc tctcggagaa cctccagcaa ccccgctgc tgtgggacct       600 actacaatgg cttcaggcgg tggcgcacca atggcagaca taacgaagg cgccgacgga       660 gtgggtaatg cctcaggaaa ttggcattgc gattccacat ggctgggcga cagagtcatc       720
accaccagca cccgaacatg ggccttgccc acctataaca accacctcta caagcaaatc       780
tccagtgctt caacggggggc cagcaacgac aaccactact cggctacag cacccctgg       840 gggtattttg attcaacag attccactgc catttctcac cacgtgactg gcagcgactc       900
atcaacaaca ttggggatt ccggcccaag agactcaact tcaagctctt caacatccaa       960
gtcaaggagg tcacgacgaa tgatggcgtc acgaccatcg ctaataacct taccagcacg      1020
gttcaagtct ctcggactc ggagtaccag ctgccgtacg ttctcggctc tgcccaccag      1080
ggctgcctgc ctccgttccc ggcggacgtg ttcatgattc cccagtacgg ctacctaaca      1140
ctcaacaacg gtagtcaggc cgtgggacgc tcctccttct actgcctgga atactttcct      1200
tcgcagatgc tgagaaccgg caacaacttc cagtttactt acaccttcga ggacgtgcct      1260
ttccacagca gctacgcccca gccagagc ttggaccggc tgatgaatcc tctgattgac      1320
cagtacctgt actacttgtc tcggactcaa acaacaggag gcacggcaaa tacgcagact      1380
```

-continued

| | |
|---|---|
| ctgggcttca gccaaggtgg gcctaataca atggccaatc aggcaaagaa ctggctgcca | 1440 |
| ggacccctgtt accgccaaca acgcgtctca acgacaaccg ggcaaaacaa caatagcaat | 1500 |
| tttacctgga ctggtgcttc aaaatataac ctcaatgggc gtgaatccat catcaaccct | 1560 |
| ggcactgcta tggcctcaca caaagacgac gaagacaagt tctttcccat gagcggtgtc | 1620 |
| atgattttg gaaagagag cgccggagct tcaaacactg cattggacaa tgtcatgatt | 1680 |
| acagacgaag aggaaattaa agccactaac cctgtggcca ccgaaagatt tgggaccgtg | 1740 |
| gcagtcaatt tccagagcag cagcacagac cctgcgaccg gagatgtgca tgctatggga | 1800 |
| gcattacctg gcatggtgtg gcaagataga acgtgtacc tgcagggtcc catttgggcc | 1860 |
| aaaattcctc acacagatgg acactttcac ccgtctcctc ttatgggcgg ctttggactc | 1920 |
| aagaacccgc ctcctcagat cctcatcaaa aacacgcctg ttcctgcgaa tcctccggcg | 1980 |
| gagttttcag ctacaaagtt tgcttcattc atcacccaat actccacagg acaagtgagt | 2040 |
| gtggaaattg aatgggagct gcagaaagaa acagcaagc gctggaatcc gaagtgcag | 2100 |
| tacacatcca attatgcaaa atctgccaac gttgatttta ctgtggacaa caatggactt | 2160 |
| tatactgagc ctcgccccat tggcacccgt tacctcaccc gtcccctgta a | 2211 |

<210> SEQ ID NO 4
<211> LENGTH: 2211
<212> TYPE: DNA
<213> ORGANISM: Artificial sequence
<220> FEATURE:
<223> OTHER INFORMATION: Recombinant sequence

<400> SEQUENCE: 4

| | |
|---|---|
| atggctgctg acggttatct tccagattgg ctcgaggaca acctttctga aggcattcga | 60 |
| gagtggtggg cgctgcaacc tggagcccct aaacccaagg caaatcaaca acatcaggac | 120 |
| aacgctcggg gtcttgtgct tccgggttac aaatacctcg acccggcaa cggactcgac | 180 |
| aaggggggaac ccgtcaacgc agcggacgcg gcagccctcg agcacgacaa ggcctacgac | 240 |
| cagcagctca aggccggtga caaccctac ctcaagtaca accacgccga cgccgagttc | 300 |
| caggagcggc tcaaagaaga tacgtctttt gggggcaacc tcgggcgagc agtcttccag | 360 |
| gccaaaaaga ggcttcttga acctcttggt ctggttgagg aagcggctaa gacggctcct | 420 |
| ggaaagaaga ggcctgtaga tcagtctcct caggaaccgg actcatcatc tggtgttggc | 480 |
| aaatcgggca acagcctgc cagaaaaaga ctaaatttcg gtcagactgg cgactcagag | 540 |
| tcagtcccag accctcaacc tctcggagaa ccaccagcag cccccacaag tttgggatct | 600 |
| aatacaatgg cttcaggcgg tggcgcacca atggcagaca taacgagggg tgccgatgga | 660 |
| gtgggtaatt cctcaggaaa ttggcattgc gattccaat ggctgggcga cagagtcatc | 720 |
| accaccagca ccagaacctg ggccctgccc acttacaaca accatctcta caagcaaatc | 780 |
| tccagccaat caggagcttc aaacgacaac cactactttg ctacagcac ccttgggggg | 840 |
| tattttgact ttaacagatt ccactgccac ttctcaccac gtgactggca gcgactcatt | 900 |
| aacaacaact ggggattccg gcccaagaaa ctcagcttca gctcttcaa catccaagtt | 960 |
| aaagaggtca cgcagaacga tggcacgacg actattgcca ataacctac cagcacggtt | 1020 |
| caagtgttta cggactcgga gtatcagctc ccgtacgtgc tcgggtcggc gcaccaaggc | 1080 |
| tgtctcccgc cgtttccagc ggacgtcttc atggtccctc agtatggata cctcaccctg | 1140 |
| aacaacggaa gtcaagcggt gggacgctca tcctttact gcctggagta cttcccttcg | 1200 |
| cagatgctaa ggactggaaa taacttccaa ttcagctata ccttcgagga tgtaccttt | 1260 |

```
cacagcagct acgctcacag ccagagtttg gatcgcttga tgaatcctct tattgatcag    1320
tatctgtact acctgaacag aacgcaagga acaacctctg aacaaccaa ccaatcacgg     1380 ctgcttttta gccaggctgg gcctcagtct atgtctttgc aggccagaaa ttggctacct    1440
gggccctgct accggcaaca gagactttca agactgctca acgacaacaa caacagtaac   1500
tttccttgga cagcggccag caaatatcat ctcaatggcc gcgactcgct ggtgaatcca   1560
ggaccagcta tggccagtca caaggacgat gaagaaaaat ttttccctat gcacggcaat   1620
ctaatatttg gcaaagaagg gacaacggca agtaacgcag aattagataa tgtaatgatt   1680
acggatgaag aagagattcg taccaccaat cctgtggcaa cagagcagta tggaactgtg   1740
gcaaataact tgcagagctc aaatacagct cccacgacta gaactgtcaa tgatcagggg   1800
gccttacctg gcatggtgtg gcaagatcgt gacgtgtacc ttcaaggacc tatctgggca   1860
aagattcctc acacggatgg acactttcat ccttctcctc tgatgggagg ctttggactg   1920
aaacatccgc ctcctcaaat catgatcaaa aatactccgg taccggcaaa tcctccgacg   1980
actttcagcc cggccaagtt tgcttcattt atcactcagt actccactgg acaggtcagc   2040
gtggaaattg agtgggagct acagaaagaa aacagcaaac gttggaatcc agagattcag   2100
tacacttcca actacaacaa gtctgttaat gtggacttta ctgtagacac taatggtgtt   2160
tatagtgaac ctcgccccat ggcacccgt taccttaccc gtcccctgta a              2211

<210> SEQ ID NO 5
<211> LENGTH: 2211
<212> TYPE: DNA
<213> ORGANISM: Artificial sequence
<220> FEATURE:
<223> OTHER INFORMATION: Recombinant sequence

<400> SEQUENCE: 5
atggctgccg atggttatct tccagattgg ctcgaggaca accttagtga aggaattcgc    60
gagtggtggg ctttgaaacc tggagcccct caacccaagg caaatcaaca acatcaagac    120
aacgctcgag tcttgtgct tccgggttac aaataccttg acccggcaa cggactcgac     180 aagggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ccggtagac gccatcaccc cagcgttctc cagactcctc tacgggcatc    480
ggcaagaaag ccaacagcc cgctaaaaag agactcaatt ttggtcagac tggcgactca    540
gagtcagtcc ccgacccaca acctctcgga gaacctccag caaccccgc tgctgtggga    600 cctactacaa tggcttcagg cggtggcgca ccaatggcag acaataacga gggtgccgat    660
ggagtgggta ttcctcagg aaaattggcat tgcgattccc aatggctggg cgacagagtc    720
atcaccacca gcaccagaac ctgggccctg cccacttaca caaccatct ctacaagcaa    780 atctccagcc aatcaggagc ttcaaacgac aaccactact ttggctacag caccccttgg    840
gggtattttg actttaacag attccactgc cacttttcac cacgtgactg caaagactc    900 atcaacaaca actggggatt ccgacccaag agactcaact tcaagctctt caacatccaa   960
gtcaaggagg tcacgacgaa tgatggcgtc acgaccatcg ctaataacct taccagcacg   1020
gttcaagtct tctcggactc ggagtaccag ttgccgtacg tcctcggctc tgcgcaccag    1080
```

| | | |
|---|---|---|
| ggctgcctcc ctccgttccc ggcggacgtg ttcatgattc cgcagtacgg ctacctaacg | 1140 | |
| ctcaacaatg cagccaagc cgtgggacgt tcatccttt actgcctgga atatttccct | 1200 | |
| tctcagatgc tgagaacggg caacaacttt accttcagct acactttga ggacgttcct | 1260 | |
| ttccacagca gctacgctca cagccagagt ctggaccgtc tcatgaatcc tctcatcgac | 1320 | |
| cagtacctgt attacttgag cagaacaaac actccaagtg gaaccaccac gcagtcaagg | 1380 | |
| cttcagtttt tcaggccgg agcgagtgac attcgggacc agtctaggaa ctggcttcct | 1440 | |
| ggaccctgtt accgccagca gcgcgtttct aaaacaaaaa cagacaacaa caacagcaat | 1500 | |
| tttacctgga ctggtgcttc aaaatataac cttaatgggc gtgaatctat aatcaaccct | 1560 | |
| ggcactgcta tggcctcaca caaagacgac gaagacaagt tctttcccat gagcggtgtc | 1620 | |
| atgattttg gaaagagag cgccggagct tcaaacactg cattggacaa tgtcatgatt | 1680 | |
| acagacgaag aggaaattaa agccactaac cctgtggcca ccgaaagatt tgggaccgtg | 1740 | |
| gcagtcaatt tccagagcag cagcacagac cctgcgaccg gagatgtgca tgttatggga | 1800 | |
| gccttacctg gaatggtgtg gcaagacaga gacgtatacc tgcagggtcc tatttgggcc | 1860 | |
| aaaattcctc acacggatgg acactttcac ccgtctcctc ttatgggcgg ctttggactc | 1920 | |
| aagaacccgc ctcctcagat cctcatcaaa aacacgcctg ttcctgcgaa tcctccggcg | 1980 | |
| gagttttcag ctacaaagtt tgcttcattc atcacccaat actccacagg acaagtgagt | 2040 | |
| gtggaaattg aatgggagct gcagaaagaa acagcaagc gctggaatcc gaagtgcag | 2100 | |
| tacacatcca attatgcaaa atctgccaac gttgatttta ctgtggacaa caatggactt | 2160 | |
| tatactgagc ctcgccccat ggcacccgt taccttaccc gtccctgta a | 2211 | |

<210> SEQ ID NO 6
<211> LENGTH: 2211
<212> TYPE: DNA
<213> ORGANISM: Artificial sequence
<220> FEATURE:
<223> OTHER INFORMATION: Recombinant sequence

<400> SEQUENCE: 6

| | | |
|---|---|---|
| atggctgccg atggttatct tccagattgg ctcgaggaca acctctctga gggcattcgc | 60 | |
| gagtggtggg acttgaaacc tggagcccct aaacccaagg caaatcaaca acatcaggac | 120 | |
| aacgctcgag gtcttgtgct tccgggttac aaataccttg acccggcaa cggactcgac | 180 | |
| aaggggagc cggtcaacgc agcagacgcg gcggccctcg agcacgacaa ggcctacgac | 240 | |
| cagcagctca aggccggaga caacccgtac ctcaagtaca accacgccga cgccgagttc | 300 | |
| caggagcggc tcaaagaaga tacgtcttt gggggcaacc tcgggcgagc agtcttccag | 360 | |
| gccaaaaaga ggcttcttga acctcttggt ctggttgagg aagcggctaa gacggctcct | 420 | |
| ggaaagaaga gaccggtaga gccatcaccc agcgttctc cagactcctc tacgggcatc | 480 | |
| ggcaagaaag ccaacagcc cgctaaaaag agactcaatt ttggtcagac tggcgactca | 540 | |
| gagtcagtcc ccgacccaca acctctcgga gaacctccag caaccccgc tgctgtggga | 600 | |
| cctactacaa tggcttcagg cggtggcgca ccaatggcag acaataacga gggtgccgat | 660 | |
| ggagtgggta ttcctcagg aaattggcat gcgattccc aatggctggg cgacagagtc | 720 | |
| atcaccacca gcaccagaac ctgggccctg cccacttaca acaaccatct ctacaagcaa | 780 | |
| atctccagcc aatcaggagc ttcaaacgac aaccactact ttggctacag cacccttgg | 840 | |
| gggtattttg actttaacag attccactgc cactttcac cacgtgactg gcaaagactc | 900 | |
| atcaacaaca ctgggggatt ccgacccaag agactcaact tcaagctctt caacatccaa | 960 | |

```
gtcaaggagg tcacgacgaa tgatggcgtc acgaccatcg ctaataacct taccagcacg    1020
gttcaagtct tctcggactc ggagtaccag ttgccgtacg tcctcggctc tgcgcaccag    1080
ggctgcctcc ctccgttccc ggcggacgtg ttcatgattc cgcagtacgg ctacctaacg    1140
ctcaacaatg gcagccaagc cgtgggacgt tcatccttt actgcctgga atatttccct    1200
tctcagatgc tgagaacggg caacaacttt accttcagct acacttttga ggacgttcct    1260
ttccacagca gctacgctca cagccagagt ctggaccgtc tcatgaatcc cctcatcgac    1320
cagtacctgt attacttgag cagaacaaac actccaagtg gaaccaccac gcagtcaagg    1380
cttcagtttt ctcaggccgg agcgagtgac attcgggacc agtctaggaa ctggcttcct    1440
ggaccctgtt accggcagca gcgcgtttct aaaacaaaaa cagacaacaa caacagcaac    1500
tttacctgga ctggtgcttc aaaatataac cttaatgggc gtgaatctat aatcaaccct    1560
ggcactgcta tggcctcaca caaagacgac gaagacaagt tctttcccat gagcggtgtc    1620 atgattttg aaaggagag cgccggagct tcaaacactg cattggacaa tgtcatgatc    1680
acagacgaag aggaaatcaa agccactaac cccgtggcca ccgaaagatt tgggactgtg    1740
gcagtcaatc tccagagcag cagcacagac cctgcgaccg gagatgtgca tgttatggga    1800
gccttacctg gaatggtgtg gcaagacaga gacgtgtacc tgcagggtcc tatttgggcc    1860
aaaattcctc acacggatgg acactttcac ccgtctcctc tcatgggcgg ctttggactt    1920
aagcacccgc ctcctcagat cctcatcaaa acacgcctg ttcctgcgaa tcctccggca    1980
gagttttcgg ctacaaagtt tgcttcattc atcacccagt attccacagg acaagtgagt    2040
gtggaaattg aatgggagct gcagaaagaa acagcaagc gctggaatcc cgaagtgcag    2100
tacacatcca attatgcaaa atctgccaac gttgattta ctgtggacaa caatggactt    2160
tatactgagc ctcgccccat tggcacccgt tacctcaccc gtccctgta a              2211

<210> SEQ ID NO 7
<211> LENGTH: 2214
<212> TYPE: DNA
<213> ORGANISM: Artificial sequence
<220> FEATURE:
<223> OTHER INFORMATION: Recombinant sequence

<400> SEQUENCE: 7
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag tcttgtgct tccgggttac aaataccttg acccggcaa cggactcgac      180 aaggggagc cggtcaacgc agcagacgcg gcggccctcg agcacgacaa ggcctacgac     240
cagcagctgc aggcgggtga caatccgtac ctgcggtata accacgccga cgccgagttt    300
caggagcgtc tgcaagaaga tacgtctttt ggggcaacc ttggcagagc agtcttccag     360
gccaaaaaga ggatccttga gcctcttggt ctggttgagg aagcagctaa aacgctcct     420 ggaaagaaga ggcctgtaga tcagtctcct caggaaccgg actcatcatc tggtgttggc    480
aaatcgggca acagcctgc cagaaaaaga ctaaatttcg gtcagactgg cgactcagag    540
tcagtcccag accctcaacc tctcggagaa ccaccgcag cccccacaag tttgggatct    600
aatacaatgg cttcaggcgg tggcgcacca atggcagaca taacgagg tgccgatggg     660 gtgggtagtt cctcgggaaa ttggcattgc gattcccaat gactggggga cagagtcatc    720
accaccagca cccgaacctg ggccctgccc acctacaaca atcacctcta caagcaaatc    780
```

| | |
|---|---|
| tccaacggga catcgggagg agccaccaac gacaacacct acttcggcta cagcaccccc | 840 |
| tgggggtatt ttgactttaa cagattccac tgccactttt caccacgtga ctggcagcga | 900 |
| ctcatcaaca caactgggga ttccggccc aagagactca gcttcaagct cttcaacatc | 960 |
| caggtcaagg aggtcacgca gaatgaaggc accaagacca cgccaataa cctcaccagc | 1020 |
| accatccagg tgtttacgga ctcggagtac cagctgccgt acgttctcgg ctctgcgcac | 1080 |
| cagggctgcc tccctccgtt cccggcggac gtgttcatga ttccgcaata cggctacctg | 1140 |
| acgctcaaca atggcagcca agccgtggga cgttcatcct tttactgcct ggaatatttc | 1200 |
| ccttctcaga tgctgagaac gggcaacaac tttaccttca gctacacctt tgaggaagtg | 1260 |
| cctttccaca gcagctacgc gcacagccag agcttggacc ggctgatgaa tcctctgatt | 1320 |
| gaccagtacc tgtactactt gtctcggact caaacaacag gaggcacggc aaatacgcag | 1380 |
| actctgggct tcagccaagg tgggcctaat acaatggcca atcaggcaaa gaactggctg | 1440 |
| ccaggacccct gttaccgcca caacgcgtc tcaacgacaa ccgggcaaaa caacaatagc | 1500 |
| aactttgcct ggactgctgg gaccaaatac catctgaatg aagaaattc attggctaat | 1560 |
| cctggcatcg ctatggcaac acacaaagac gacgaggagc gtttttttcc cagtaacggg | 1620 |
| atcctgattt ttggcaaaca aaatgctgcc agagacaatg cggattacag cgatgtcatg | 1680 |
| ctcaccagcg aggaagaaat caaaaccact aaccctgtgg ctacagagga atacggtatc | 1740 |
| gtggcagata acttgcagca gcaaaacacg gctcctcaaa ttggaactgt caacagccag | 1800 |
| ggggccttac ccggtatggt ctggcagaac cgggacgtgt acctgcaggg tcccatctgg | 1860 |
| gccaagattc tcacacggga cggcaacttc caccgtctc cgctgatggg cggctttggc | 1920 |
| ctgaaacatc ctccgcctca gatcctgatc aagaacacgc ctgtacctgc ggatcctccg | 1980 |
| accaccttca accagtcaaa gctgaactct ttcatcacgc aatacagcac cggacaggtc | 2040 |
| agcgtggaga tcgagtggga gctgcagaag gaaaacagca gcgctggaa cccggagatc | 2100 |
| cagtacactt ccaactatta caagtctaat aatgttgaat ttgctgttaa tactgaaggt | 2160 |
| gtatatagtg aaccccgccc cattggcacc agatacctga ctcgtaatct gtaa | 2214 |

<210> SEQ ID NO 8
<211> LENGTH: 2214
<212> TYPE: DNA
<213> ORGANISM: Artificial sequence
<220> FEATURE:
<223> OTHER INFORMATION: Recombinant sequence

<400> SEQUENCE: 8

| | |
|---|---|
| atggctgccg atggttatct tccagattgg ctcgaggaca accttagtga aggaattcgc | 60 |
| gagtggtggg cttttgaaacc tggagcccct caacccaagg caaatcaaca acatcaagac | 120 |
| aacgctcgag gtcttgtgct tccgggttac aaataccttg accccggcaa cggactcgac | 180 |
| aagggggagc cggtcaacgc agcagacgcg gcggccctcg agcacgacaa ggcctacgac | 240 |
| cagcagctgc aggcgggtga caatccgtac ctgcggtata accacgccga cgccgagttt | 300 |
| caggagcgtc tgcaagaaga tacgtctttt gggggcaacc ttggcagagc agtcttccag | 360 |
| gccaaaaga ggatccttga gcctcttggt ctggttgagg aagcagctaa aacgctcct | 420 |
| ggaaagaaga ggcctgtaga tcagtctcct caggaaccgg actcatcatc tggtgttggc | 480 |
| aaatcgggca aacagcctgc cagaaaaaga ctaaatttcg gtcagactgg cgactcagag | 540 |
| tcagtcccag acccctcaacc tctcggagaa ccaccagcag cccccacaag tttgggatct | 600 |
| aatacaatgg cttcaggcgg tggcgcacca atggcagaca ataacgaggg tgccgatggg | 660 |

-continued

```
gtgggtagtt cctcgggaaa ttggcattgc gattcccaat ggctggggga cagagtcatc      720
accaccagca cccgaacctg ggccctgccc acctacaaca atcacctcta caagcaaatc      780
tccaacggga catcgggagg agccaccaac gacaacacct acttcggcta cagcacccccc    840 tgggggtatt ttgactttaa cagattccac tgccactttt caccacgtga ctggcagcga      900
ctcatcaaca caactgggg attccggccc aagagactca gcttcaagct cttcaacatc       960
caggtcaagg aggtcacgca gaatgaaggc accaagacca tcgccaataa cctcaccagc     1020
accatccagg tgtttacgga ctcggagtac cagctgccgt acgttctcgg ctctgcgcac     1080
cagggctgcc tccctccgtt cccggcggac gtgttcatga ttccgcaata cggctacctg     1140
acgctcaaca atggcagcca agccgtggga cgttcatcct tttactgcct ggaatatttc     1200
ccttctcaga tgctgagaac gggcaacaac tttaccttca gctacacctt tgaggaagtg     1260
ccttttcaca gcagctacgc gcacagccag agcttggacc ggctgatgaa tcctctgatt     1320
gaccagtacc tgtactactt gtctcggact caaacaacag gaggcacggc aaatacgcag     1380
actctgggct tcagccaagg tgggcctaat acaatggcca atcaggcaaa gaactggctg     1440 ccaggacccct gttaccgcca acaacgcgtc tcaacgacaa ccgggcaaaa caacaatagc    1500
aactttgcct ggactgctgg gaccaaatac catctgaatg gaagaaattc attggctaat     1560
cctggcatcg ctatgcaac acacaaagac gacgaggagc gttttttttcc cagtaacggg     1620 atcctgattt ttggcaaaca aaatgctgcc agagacaatg cggattacag cgatgtcatg     1680
ctcaccagcg aggaagaaat caaaaccact aaccctgtgg ctacagagga atacggtatc     1740
gtggcagata acttgcagca gcaaaacacg gctcctcaaa ttggaactgt caacagccag     1800
ggggccttac ccgtatggt ctggcagaac cgggacgtgt acctgcaggg tcccatctgg      1860
gccaagattc ctcacacgga cggcaacttc cacccgtctc cgctgatggg cggctttggc     1920
ctgaaacatc ctccgcctca gatcctgatc aagaacacgc ctgtacctgc ggatcctccg     1980
accaccttca accagtcaaa gctgaactct ttcatcacgc aatacagcac cggacaggtc     2040
agcgtggaga tcgagtggga gctgcagaag gaaaacagca agcgctggaa cccggagatc     2100
cagtacactt ccaactatta caagtctaat aatgttgaat ttgctgttaa tactgaaggt     2160
gtatatagtg aaccccgccc cattggcacc agatacctga ctcgtaatct gtaa            2214
```

<210> SEQ ID NO 9
<211> LENGTH: 2211
<212> TYPE: DNA
<213> ORGANISM: Artificial sequence
<220> FEATURE:
<223> OTHER INFORMATION: Recombinant sequence

<400> SEQUENCE: 9

```
atggctgccg atggttatct tccagattgg ctcgaggaca acctctctga gggcattcgc       60
gagtggtggg acttgaaacc tggagcccct aaacccaagg caaatcaaca acatcaggac      120
aacgctcgag gtcttgtgct tccgggttac aaataccttg acccggcaa cggactcgac       180 aagggggagc cggtcaacgc agcagacgcg gcggccctcg agcacgacaa ggcctacgac      240
cagcagctca aggccggaga caacccgtac ctcaagtaca accacgccga cgccgagttc      300
caggagcggc tcaagaagaa tacgtctttt ggggggcaacc tcgggcgagc agtcttccag     360
gccaaaaaga ggcttcttga acctcttggt ctggttgagg aagcggctaa gacggctcct      420
ggaaagaaga gaccggtaga gccatcaccc cagcgttctc cagactcctc tacgggcatc      480
```

-continued

| | |
|---|---|
| ggcaagaaag gccaacagcc cgctaaaaag agactcaatt ttggtcagac tggcgactca | 540 |
| gagtcagtcc ccgacccaca acctctcgga gaacctccag caaccccgc tgctgtggga | 600 |
| cctactacaa tggcttcagg cggtggcgca ccaatggcag acaataacga gggtgccgat | 660 |
| ggagtgggta attcctcagg aaattggcat tgcgattccc aatggctggg cgacagagtc | 720 |
| atcaccacca gcaccagaac ctgggccctg cccacttaca acaaccatct ctacaagcaa | 780 |
| atctccagcc aatcaggagc ttcaaacgac aaccactact ttggctacag cacccttgg | 840 |
| gggtattttg actttaacag attccactgc cacttttcac cacgtgactg gcaaagactc | 900 |
| atcaacaaca actggggatt ccgacccaag agactcaact tcaagctctt caacatccaa | 960 |
| gtcaaggagg tcacgacgaa tgatggcgtc acgaccatcg ctaataacct taccagcacg | 1020 |
| gttcaagtct tctcggactc ggagtaccag ttgccgtacg tcctcggctc tgcgcaccag | 1080 |
| ggctgcctcc ctccgttccc ggcggacgtg ttcatgattc cgcagtacgg ctacctaacg | 1140 |
| ctcaacaatg gcagccaagc cgtgggacgt tcatcctttt actgcctgga atatttccct | 1200 |
| tctcagatgc tgagaacggg caacaacttt accttcagct acacttttga ggacgttcct | 1260 |
| ttccacagca gctacgctca cagccagagt ctggaccgtc tcatgaatcc tctcatcgac | 1320 |
| cagtacctgt attacttgag cagaacaaac actccaagtg gaaccaccac gcagtcaagg | 1380 |
| cttcagtttt tcaggccgg agcgagtgac attcgggacc agtctaggaa ctggcttcct | 1440 |
| ggaccctgtt accgccagca gcgcgtttct aaaacaaaaa cagacaacaa caacagcaat | 1500 |
| tttacctgga ctggtgcttc aaaatataac cttaatgggc gtgaatctat aatcaaccct | 1560 |
| ggcactgcta tggcctcaca caaagacgac gaagacaagt tctttcccat gagcggtgtc | 1620 |
| atgattttg gaaagagag cgccggagct tcaaacactg cattggacaa tgtcatgatt | 1680 |
| acagacgaag aggaaattaa agccactaac cctgtggcca ccgaaagatt tgggaccgtg | 1740 |
| gcagtcaatt tccagagcag cagcacagac cctgcgaccg gagatgtgca tgctatggga | 1800 |
| gcattacctg gcatggtgtg gcaagataga acgtgtacc tgcagggtcc catttgggcc | 1860 |
| aaaattcctc acacagatgg acactttcac ccgtctcctc ttatgggcgg ctttggactc | 1920 |
| aagaacccgc ctcctcagat cctcatcaaa aacacgcctg ttcctgcgaa tcctccggcg | 1980 |
| gagtttcag ctacaaagtt tgcttcattc atcacccaat actccacagg acaagtgagt | 2040 |
| gtggaaattg aatgggagct gcagaaagaa aacagcaagc gctggaatcc cgaagtgcag | 2100 |
| tacacatcca attatgcaaa atctgccaac gttgatttta ctgtggacaa caatggactt | 2160 |
| tatactgagc ctcgccccat tggcacccgt taccttaccc gtcccctgta a | 2211 |

<210> SEQ ID NO 10
<211> LENGTH: 2211
<212> TYPE: DNA
<213> ORGANISM: Artificial sequence
<220> FEATURE:
<223> OTHER INFORMATION: Recombinant sequence

<400> SEQUENCE: 10

| | |
|---|---|
| atggctgccg atggttatct tccagattgg ctcgaggaca accttagtga aggaattcgc | 60 |
| gagtggtggg cgctgaaacc tggagccccg aagcccaaag ccaaccagca aaagcaggac | 120 |
| gacggccggg gtctggtgct tccgggttac aaatacctcg acccggtaa cggactcgac | 180 |
| aaaggagagc cggtcaacga ggcggacgcg gcagccctcg agcacgacaa ggcctacgac | 240 |
| cagcagctca agcgggtga caatccgtac ctgcggtata accacgccga cgccgagttt | 300 |
| caggagcgtc tgcaagaaga tacgtctttt gggggcaacc tcgggcgagc agtcttccag | 360 |

```
gccaagaagc gggttctcga acctctcggt ctggttgagg aaggcgctaa gacggctccc    420
ggaaagaaac gtccggtaga gcagtcgcca aagagccag actcctctac ggcatcggc     480 aagaaaggcc aacagcccgc cagaaaaaga ctcaatttcg gtcagactgg cgactcagag    540
tcagttccag accctcaacc tctcggagaa cctccagcag cgccctctgg tgtgggacct    600
actacaatgg cttcaggcgg tggcgcacca atggcagaca ataacgaagg cgccgacgga    660
gtgggtaatg cctcaggaaa ttggcattgc gattccacat ggctgggcga cagagtcatc    720
accaccagca cccgaacatg ggccttgccc acctataaca accacctcta caagcaaatc    780
tccagtgctt caacggggc cagcaacgac aacacctact cggctacag cacccccgg     840 gggtattttg atttcaacag attccactgc catttctcac cacgtgactg cagcgactc    900 atcaacaaca attggggatt ccggcccaag agactcaact tcaaactctt caacatccaa    960
gtcaaggagg tcacgacgaa tgatggcgtc acgaccatcg ctaataacct taccagcacg   1020
gttcaagtct ctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg cagccaggc agtgggacgg tcatcctttt actgcctgga atatttccca   1200
tcgcagatgc tgagaacggg caataacttt accttcagct acaccttcga ggacgtgcct   1260
ttccacagca gctacgcgca cagccagagc ctggaccggc tgatgaatcc tctcatcgac   1320
cagtacctgt attcctgaa cagaactcag aatcagtccg gaagtgccca aaacaaggac   1380
ttgctgttta ccgggggtc tccagctggc atgtctgttc agcccaaaaa ctggctacct   1440
ggaccctgtt atcggcagca gcgcgtttct aaaacaaaaa cagacaacaa caacagcaat   1500
tttacctgga ctggtgcttc aaaatataac ctcaatgggc gtgaatccat catcaaccct   1560
ggcactgcta tggcctcaca caaagacgac gaagacaagt tctttcccat gagcggtgtc   1620 atgattttg gaaaagagag cgccggagct tcaaacactg cattggacaa tgtcatgatt   1680
acagacgaag aggaaattaa agccactaac cctgtggcca ccgaaagatt tgggaccgtg   1740
gcagtcaatt tccagagcag cagcacagac cctgcgaccg gagatgtgca tgttatggga   1800
gccttacctg gaatggtgtg gcaagacaga gacgtatacc tgcagggtcc tatttgggcc   1860
aaaattcctc acacagatgg acactttcac ccgtctcctc ttatgggcgg cttttggactc   1920 aagaacccgc ctcctcagat cctcatcaaa aacacgcctg ttcctgcgaa tcctccggca   1980
gagttttcgg ctacaaagtt tgcttcattc atcacccagt attccacagg acaagtgagc   2040
gtggagattg aatgggagct gcagaaagaa acagcaaac gctggaatcc gaagtgcag   2100 tatacatcta actatgcaaa atctgccaac gttgatttca ctgtggacaa caatggactt   2160
tatactgagc ctcgccccat tggcacccgt tacctcaccc gtcccctgta a           2211
```

<210> SEQ ID NO 11
<211> LENGTH: 2205
<212> TYPE: DNA
<213> ORGANISM: Artificial sequence
<220> FEATURE:
<223> OTHER INFORMATION: Recombinant sequence

<400> SEQUENCE: 11

```
atggctgctg acggttatct tccagattgg ctcgaggaca acctttctga aggcattcgt     60
gagtggtggg ctctgaaacc tggagtccct caacccaaag cgaaccaaca acaccaggac    120
aaccgtcggg gtcttgtgct tccgggttac aaatacctcg acccggtaa cggactcgac    180
```

```
aaaggagagc cggtcaacga ggcggacgcg gcagccctcg aacacgacaa ggcctacgac    240
cagcagctca aggccggaga caacccgtac ctcaagtaca ccacgccga cgccgagttc    300 caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct     600 cttacaatgg cttcaggtgg tggcgcacca gtggcagaca taacgaagg tgccgatgga     660 gtgggtagtt cctcgggaaa ttggcattgc gattcccaat ggctggggga cagagtcatc    720
accaccagca cccgaacctg ggccctgccc acctacaaca ccacctcta caaacaaatt     780 tccagccaat caggagcctc gaacgacaat cactactttg gctacagcac cccttggggg    840
tattttgact tcaacagatt ccactgccac ttttcaccac gtgactggca gcgactcatc    900
aacaacaact ggggattccg gcccaagaga ctcagcttca gctcttcaa catccaggtc     960 aaagaggtta cggacaacaa tggagtcaag accatcgcca ataaccttac cagcacggtc   1020
caggtcttca cggactcaga ctatcagctc ccgtacgtgc tcgggtcggc tcacgagggc   1080
tgcctcccgc cgttcccagc ggacgttttc atgattcctc agtacgggta tctgacgctt   1140
aatgatggaa gccaggccgt gggtcgttcg tccttttact gcctggaata tttcccgtcg   1200
caaatgctaa gaacgggtaa caacttccag ttcagctacg agtttgagaa cgtacctttc   1260
catagcagct acgctcacag ccaaagcctg gaccgactaa tgaatccact catcgaccaa   1320
tacttgtact atctctcaaa gactattaac ggttctggac agaatcaaca aacgctaaaa   1380
ttcagtgtgg ccggacccag caacatggct gtccagggaa gaaactacat acctggaccc   1440
agctaccgac aacaacgtgt ctcaaccact gtgactcaaa acaacaacag cgaatttgct   1500
tggcctggag cttcttcttg ggctctcaat ggacgtaata gcttgatgaa tcctggacct   1560
gctatggcca gccacaaaga aggagaggac cgtttctttc ctttgtctgg atctttaatt   1620
tttggcaaac aaggaactgg aagagacaac gtggatgcgg acaaagtcat gataaccaac   1680
gaagaagaaa ttaaaactac taacccggta gcaacggagt cctatggaca gtggccaca    1740 aaccaccaga gtgcccaagc acaggcgcag accggctggg ttcaaaacca aggaatactt   1800
ccgggtatgg tttggcagga cagagatgtg tacctgcaag acccatctg gccaagatt    1860 cctcacacgg acgcaacttc cacccgtctc cgctgatgg gcggctttgg cctgaaacat   1920
cctccgcctc agatcctgat caagaacacg cctgtacctg cggatcctcc gaccaccttc   1980
aaccagtcaa agctgaactc tttcatcacg caatacagca ccggacaggt cagcgtggaa   2040
attgaatggg agctgcagaa ggaaaacagc aagcgctgga atcccgaagt gcagtataca   2100
tctaactatg caaatctgc caacgttgat ttcactgtgg acaacaatgg actttatact   2160
gagcctcgcc ccattggcac ccgttacctc acccgtcccc tgtaa                  2205
```

<210> SEQ ID NO 12
<211> LENGTH: 2211
<212> TYPE: DNA
<213> ORGANISM: Artificial sequence
<220> FEATURE:
<223> OTHER INFORMATION: Recombinant sequence

<400> SEQUENCE: 12

```
atggctgccg atggttatct tccagattgg ctcgaggaca acctctctga gggcattcgc     60
```

```
gagtggtggg cgctgaaacc tggagccccg aagcccaaag ccaaccagca aaagcaggac    120
gacggccggg gtctggtgct tcctggctac aagtacctcg acccttcaa cggactcgac    180 aaggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagt gggttctcga acctctcggt ctggttgagg aaggcgctaa gacggctcct    420
ggaaagaaac gtccggtaga gcagtcgcca caagagccag actcctcctc gggcatcggc    480
aagacaggcc agcagcccgc taaaaagaga ctcaattttg gtcagactgg cgactcagag    540
tcagtccccg acccacaacc tctcggagaa cctccagcaa ccccgctgc tgtgggacct    600 actacaatgg cttcaggcgg tggcgcacca atggcagaca taacgaagg cgccgacgga    660 gtgggtaatg cctcaggaaa ttggcattgc gattccacat ggctgggcga cagagtcatc    720
accaccagca cccgcacctg gccttgccc acctacaata accacctcta caagcaaatc    780
tccagtgctt caacggggc cagcaacgac aaccactact tcggctacag cacccccctgg   840 gggtattttg atttcaacag attccactgc catttctcac cacgtgactg gcagcgactc    900
atcaacaaca attggggatt ccggcccaag agactcaact tcaagctctt caacatccaa    960
gtcaaggagg tcacgacgaa tgatggcgtc acaaccatcg ctaataacct taccagcacg   1020
gttcaagtct ctctcggactc ggagtaccag cttccgtacg tcctcggctc tgcgcaccag   1080
ggctgcctcc ctccgttccc ggcggacgtg ttcatgattc cgcaatacgg ctacctgacg   1140
ctcaacaatg gcagccaagc cgtgggacgt tcatccttt actgcctgga atatttccct    1200
tctcagatgc tgagaacggg caacaacttt accttcagct acacctttga ggaagtgcct    1260
ttccacagca gctacgcgca cagccagagc ctggaccggc tgatgaatcc tctcatcgac    1320
caatacctgt attacctgaa cagaactcaa aatcagtccg gaagtgccca aaacaaggac    1380
ttgctgttta gccgtgggtc tccagctggc atgtctgttc agcccaaaaa ctggctacct    1440
ggaccctgtt atcggcagca gcgcgtttct aaaacaaaaa cagacaacaa caacagcaat    1500
tttacctgga ctggtgcttc aaaatataac ctcaatgggc gtgaatccat catcaaccct    1560
ggcactgcta tggcctcaca caaagacgac gaagacaagt tctttcccat gagcggtgtc    1620
atgatttttg gaaaggagag cgccggagct tcaaacactg cattggacaa tgtcatgatc    1680
accgacgaag aggaaatcaa agccactaac cccgtggcca ccgaaagatt tgggactgtg    1740
gcagtcaatc tccagagcag cagcacagac cctgcgaccg agatgtgca tgttatggga    1800 gccttacctg gcatggtgtg gcaagataga gacgtgtacc tgcagggtcc catttgggcc    1860
aaaattcctc acacagatgg acactttcac ccgtctcctc ttatgggcgg ctttggactc    1920
aagaacccgc ctcctcagat cctcatcaaa aacacgcctg ttcctgcgaa tcctccggcg    1980
gagttttcag ctacaaagtt tgcttcattc atcacccaat actccacagg acaagtgagt    2040
gtggaaattg aatgggagct gcagaaagaa aacagcaagc gctggaatcc cgaagtgcag    2100
tacacatcca attatgcaaa atctgccaac gttgattta ctgtggacaa caatggactt    2160
tatactgagc ctcgccccat tggcacccgt tacctcaccc gtccctgta a             2211
```

<210> SEQ ID NO 13
<211> LENGTH: 2214
<212> TYPE: DNA
<213> ORGANISM: Artificial sequence
<220> FEATURE:

<223> OTHER INFORMATION: Recombinant sequence

<400> SEQUENCE: 13

| | | | | | |
|---|---|---|---|---|---|
| atggctgccg | atggttatct | tccagattgg | ctcgaggaca | accttagtga | aggaattcgc | 60 |
| gagtggtggg | cttttgaaacc | tggagcccct | caacccaagg | caaatcaaca | acatcaagac | 120 |
| aacgctcgag | gtcttgtgct | tccgggttac | aaataccttg | acccggcaa | cggactcgac | 180 |
| aaggggagc | cggtcaacgc | agcagacgcg | gcggccctcg | agcacgacaa | ggcctacgac | 240 |
| cagcagctgc | aggcgggtga | caatccgtac | ctgcggtata | ccacgccga | cgccgagttt | 300 |
| caggagcgtc | tgcaagaaga | tacgtctttt | gggggcaacc | ttggcagagc | agtcttccag | 360 |
| gccaaaaaga | ggatccttga | gcctcttggt | ctggttgagg | aagcagctaa | aacggctcct | 420 |
| ggaaagaaga | ggcctgtaga | tcagtctcct | caggaaccgg | actcatcatc | tggtgttggc | 480 |
| aaatcgggca | acagcctgc | cagaaaaaga | ctaaatttcg | gtcagactgg | cgactcagag | 540 |
| tcagtcccag | accctcaacc | tctcggagaa | ccaccagcag | ccccacaag | tttgggatct | 600 |
| aatacaatgg | cttcaggcgg | tggcgcacca | atggcagaca | taacgaggg | tgccgatggg | 660 |
| gtgggtagtt | cctcgggaaa | ttggcattgc | gattcccaat | ggctggggga | cagagtcatc | 720 |
| accaccagca | cccgaacctg | ggccctgccc | acctacaaca | atcacctcta | caagcaaatc | 780 |
| tccaacggga | catcgggagg | agccaccaac | gacaacacct | acttcggcta | cagcaccccc | 840 |
| tgggggtatt | ttgactttaa | cagattccac | tgccactttt | caccacgtga | ctggcagcga | 900 |
| ctcatcaaca | caactgggg | attccggccc | aagagactca | gcttcaagct | cttcaacatc | 960 |
| caggtcaagg | aggtcacgca | gaatgaaggc | accaagacca | tcgccaataa | cctcaccagc | 1020 |
| accatccagg | tgtttacgga | ctcggagtac | cagctgccgt | acgttctcgg | ctcggcgcac | 1080 |
| cagggctgcc | tccctccgtt | cccggcgac | gtcttcatgg | tgccacagta | tggatacctg | 1140 |
| acgctcaaca | atggcagcca | agccgtggga | cgttcatcct | tttactgcct | ggaatatttc | 1200 |
| ccttctcaga | tgctgagaac | gggcaacaac | tttaccttca | gctacacctt | tgaggaagtg | 1260 |
| cctttccaca | gcagctacgc | gcacagccag | agcttggacc | ggctgatgaa | tcctctgatt | 1320 |
| gaccagtacc | tgtactactt | gtctcggact | caaacaacag | gaggcacggc | aaatacgcag | 1380 |
| actctgggct | tcagccaagg | tgggcctaat | acaatggcca | atcaggcaaa | gaactggctg | 1440 |
| ccaggaccct | gttaccgcca | caacgcgtc | tcaacgacaa | ccgggcaaaa | caacaatagc | 1500 |
| aactttgcct | ggactgctgg | gaccaaatac | catctgaatg | gaagaaattc | attggctaat | 1560 |
| cctggcatcg | ctatgcaac | acacaaagac | gacgaggagc | gttttttttcc | cagtaacggg | 1620 |
| atcctgattt | ttggcaaaca | aaatgctgcc | agagacaatg | cggattacag | cgatgtcatg | 1680 |
| ctcaccagcg | aggaagaaat | caaaaccact | aaccctgtgg | ctacagagga | atacggtatc | 1740 |
| gtggcagata | acttgcagca | gcaaaacacg | gctcctcaaa | ttggaactgt | caacagccag | 1800 |
| ggggacttac | ccggtatggt | ctggcagaac | cgggacgtgt | acctgcaggg | tcccatctgg | 1860 |
| gccaagattc | ctcacgga | cggcaacttc | cacccgtctc | cgctgatggg | cggctttggc | 1920 |
| ctgaaacatc | ctccgcctca | gatcctgatc | aagaacacgc | tgtacctgc | ggatcctccg | 1980 |
| accaccttca | accagtcaaa | gctgaactct | ttcatcacgc | aatacagcac | cggacaggtc | 2040 |
| agcgtggaga | tcgagtggga | gctgcagaag | gaaaacagca | agcgctggaa | cccggagatc | 2100 |
| cagtacactt | ccaactatta | caagtctaat | aatgttgaat | ttgctgttaa | tactgaaggt | 2160 |
| gtatatagtg | aaccccgccc | cattggcacc | agataccctg | actcgtaatct | gtaa | 2214 |

```
<210> SEQ ID NO 14
<211> LENGTH: 2205
<212> TYPE: DNA
<213> ORGANISM: Artificial sequence
<220> FEATURE:
<223> OTHER INFORMATION: Recombinant sequence

<400> SEQUENCE: 14
```

| | | | | | |
|---|---|---|---|---|---|
| atggctgctg | acggttatct | tccagattgg | ctcgaggaca | acctttctga | aggcattcgt | 60 |
| gagtggtggg | ctctgaaacc | tggagtccct | caacccaaag | cgaaccaaca | acaccaggac | 120 |
| aactgtcggg | gtcttgtgct | tccgggttac | aaatacctcg | acccggtaa | cggactcgac | 180 |
| aaaggagagc | cggtcaacga | ggcggacgcg | gcagccctcg | aacacgacaa | ggcctacgac | 240 |
| cagcagctca | aggccggaga | caacccgtac | ctcaagtaca | accacgccga | cgccgagttc | 300 |
| caggagcggc | tcaaagaaga | tacgtctttt | gggggcaacc | tcgggcgagc | agtcttccag | 360 |
| accaaaaaga | ggcttcttga | acctcttggt | ctggttgagg | aagcggctaa | gacggctcct | 420 |
| ggaaagaaga | ggcctgtaga | gcagtctcct | caggaaccgg | actcctccgc | gggtattggc | 480 |
| aaatcgggtg | cacagcccgc | taaaaagaga | ctcaatttcg | gtcagactgg | cgacacagag | 540 |
| tcagtcccag | accctcaacc | aatcggagaa | cctcccgcag | cccctcagg | tgtgggatct | 600 |
| cttacaatgg | cttcaggtgg | tggcgcacca | gtggcagaca | ataacgaagg | tgccgatgga | 660 |
| gtgggtagtt | cctcgggaaa | ttggcattgc | gattcccaat | ggctggggga | cagagtcatc | 720 |
| accaccagca | cccgaacctg | ggccctgccc | acctacaaca | accacctcta | caaacaaatt | 780 |
| tccagccaat | caggagcctc | gaacgacaat | cactactttg | ctacagcac | cccttggggg | 840 |
| tattttgact | tcaacagatt | ccactgccac | ttttcaccac | gtgactggca | gcgactcatc | 900 |
| aacaacaact | ggggattccg | gcccaagaga | ctcagcttca | agctcttcaa | catccaggtc | 960 |
| aaagaggtta | cggacaacaa | tggagtcaag | accatcgcca | taaccttac | cagcacggtc | 1020 |
| caggtcttca | cggactcaga | ctatcagctc | ccgtacgtgc | tcgggtcggc | tcacgagggc | 1080 |
| tgcctcccgc | cgttcccagc | ggacgttttc | atgattcctc | agtacgggta | tctgacgctt | 1140 |
| aatgatggaa | gccaggccgt | gggtcgttcg | tccttttact | gcctggaata | tttcccgtcg | 1200 |
| caaatgctaa | gaacgggtaa | caacttccag | ttcagctacg | agtttgagaa | cgtacctttc | 1260 |
| catagcagct | acgctcacag | ccaaagcctg | gaccgactaa | tgaatccact | catcgaccaa | 1320 |
| tacttgtact | atctctcaaa | gactattaac | ggttctggac | agaatcaaca | aacgctaaaa | 1380 |
| ttcagtgtgg | ccggacccag | caacatggct | gtccagggaa | gaaactacat | acctggaccc | 1440 |
| agctaccgac | aacaacgtgt | ctcaaccact | gtgactcaaa | acaacaacag | cgaatttgct | 1500 |
| tggcctggag | cttcttcttg | ggctctcaat | ggacgtaata | gcttgatgaa | tcctggacct | 1560 |
| gctatggcca | gccacaaaga | aggagaggac | cgtttctttc | ctttgtctgg | atctttaatt | 1620 |
| tttggcaaac | aaggaactgg | aagagacaac | gtggatgcgg | acaaagtcat | gataaccaac | 1680 |
| gaagaagaaa | ttaaaactac | taaccccgta | gcaacggagt | cctatggaca | agtggccaca | 1740 |
| aaccaccaga | gtgcccaagc | acaggcgcag | accggctggg | ttcaaaacca | aggaatactt | 1800 |
| ccgggtatgg | tttggcagga | cagagatgtg | tacctgcaag | gacccatctg | gccaagatt | 1860 |
| cctcacacga | cggcaacttt | ccaccgtct | ccgctgatgg | gcggctttgg | cctgaaacat | 1920 |
| cctccgcctc | agatcctgat | caagaacacg | cctgttcctg | cgaatcctcc | ggcggagttt | 1980 |
| tcagctacaa | agtttgcttc | attcatcacc | cagtactcca | caggacaagt | gagtgtggaa | 2040 |
| attgaatggg | agctgcagaa | agaaaacagc | aagcgctgga | atcccgaagt | gcagtacaca | 2100 |

```
tccaattatg caaaatctgc caacgttgat tttactgtgg acaacaatgg actttatact    2160
gagcctcgcc ccattggcac ccgttacctt accaaacctc tgtaa                   2205

<210> SEQ ID NO 15
<211> LENGTH: 2211
<212> TYPE: DNA
<213> ORGANISM: Artificial sequence
<220> FEATURE:
<223> OTHER INFORMATION: Recombinant sequence

<400> SEQUENCE: 15
atggctgccg atggttatct tccagattgg ctcgaggaca acctctctga gggcattcgc     60
gagtggtggg acttgaaacc tggagcccct aaacccaagg caaatcaaca acatcaggac    120
aacgctcgag gtcttgtgct tccgggttac aaataccttg acccggcaa cggactcgac    180 aaggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga gaccggtaga gccatcaccc cagcgttctc cagactcctc tacgggcatc    480
ggcaagaaag ccaacagcc cgctaaaaag agactcaatt ttggtcagac tggcgactca    540
gagtcagtcc ccgacccaca acctctcgga gaacctccag caaccccgc tgctgtggga    600 cctactacaa tggcttcagg cggtggcgca ccaatggcag acaataacga gggtgccgat    660
ggagtgggta attcctcagg aaattggcat gcgattccc aatggctggg cgacagagtc    720
atcaccacca gcaccagaac ctgggccctg cccacttaca acaaccatct ctacaagcaa    780
atctccagcc aatcaggagc ttcaaacgac aaccactact ttggctacag caccccttgg    840
gggtattttg actttaacag attccactgc cacttttcac cacgtgactg gcaaagactc    900
atcaacaaca ctgggggatt ccgacccaag agactcaact tcaagctctt caacatccaa    960
gtcaaggagg tcacgacgaa tgatggcgtc acgaccatcg ctaataacct taccagcacg   1020
gttcaagtct ctctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg gcagccaagc cgtgggacgt tcatcctttt actgcctgga atatttccct   1200
tctcagatgc tgagaacggg caacaacttt accttcagct cacttttga ggacgttcct   1260 ttccacagca gctacgctca cagccagagt ctggaccgtc tcatgaatcc tctcatcgac   1320
cagtacctgt attacttgag cagaacaaac actccaagtg gaaccaccac gcagtcaagg   1380 cttcagttttt ctcaggccgg agcgagtgac attcgggacc agtctaggaa ctggcttcct   1440
ggaccctgtt accgccagca gcgcgtttct aaaacaaaaa cagacaacaa caacagcaat   1500
tttacctgga ctggtgcttc aaaatataac cttaatgggc gtgaatctat aatcaaccct   1560
ggcactgcta tggcctcaca caaagacgac gaagacaagt tctttcccat gagcggtgtc   1620 atgattttg aaaagagag cgccggagct tcaaacactg cattggacaa tgtcatgatc   1680
acagacgaag aggaaatcaa agccactaac cccgtggcca ccgaaagatt tgggactgtg   1740
gcagtcaatc tccagagcag cagcacagac cctgcgaccg gagatgtgca tgttatggga   1800
gcattacctg gcatggtgtg gcaagataga gacgtgtacc tgcagggtcc catttgggcc   1860
aaaattcctc acacagatgg acactttcac ccgtctcctc ttatgggcgg ctttggactc   1920
aagaacccgc ctcctcagat cctcatcaaa aacacgcctg ttcctgcgaa tcctccggcg   1980
```

| | |
|---|---|
| gagttttcag ctacaaagtt tgcttcattc atcacccaat actccacagg acaagtgagt | 2040 |
| gtggaaattg aatgggagct gcagaaagaa aacagcaagc gctggaatcc cgaagtgcag | 2100 |
| tacacatcca attatgcaaa atctgccaac gttgatttta ctgtggacaa caatggactt | 2160 |
| tatactgagc ctcgcccat tggcacccgt taccttaccc gtcccctgta a | 2211 |

<210> SEQ ID NO 16
<211> LENGTH: 2214
<212> TYPE: DNA
<213> ORGANISM: Artificial sequence
<220> FEATURE:
<223> OTHER INFORMATION: Recombinant sequence

<400> SEQUENCE: 16

| | |
|---|---|
| atggctgccg atggttatct tccagattgg ctcgaggaca accttagtga aggaattcgc | 60 |
| gagtggtggg ctttgaaacc tggagcccct caacccaagg caaatcaaca acatcaagac | 120 |
| aacgctcgag gtcttgtgct tccgggttac aaatacctg acccggcaa cggactcgac | 180 |
| aaggggagc cggtcaacgc agcagacgcg gcggccctcg agcacgacaa ggcctacgac | 240 |
| cagcagctgc aggcgggtga caatccgtac ctgcggtata accacgccga cgccgagttt | 300 |
| caggagcgtc tgcaagaaga tacgtctttt ggggcaacc ttggcagagc agtcttccag | 360 |
| gccaaaaaga ggatccttga gcctcttggt ctggttgagg aagcagctaa acggctcct | 420 |
| ggaaagaaga ggcctgtaga tcagtctcct caggaaccgg actcatcatc tggtgttggc | 480 |
| aaatcgggca acagcctgc cagaaaaaga ctaaatttcg gtcagactgg cgactcagag | 540 |
| tcagtcccag accctcaacc tctcggagaa ccaccagcag cccccacaag tttgggatct | 600 |
| aatacaatgg cttcaggcgg tggcgcacca atggcagaca taacgaggg tgccgatggg | 660 |
| gtgggtagtt cctcgggaaa ttggcattgc gattcccaat ggctggggga cagagtcatc | 720 |
| accaccagca cccgaacctg ggccctgccc acctacaaca tcacctcta caagcaaatc | 780 |
| tccaacggga catcggagg agccaccaac gacaacacct acttcggcta cagcaccccc | 840 |
| tgggggtatt ttgactttaa cagattccac tgccactttt caccacgtga ctggcagcga | 900 |
| ctcatcaaca caactgggg attccggccc aagagactca gcttcaagct cttcaacatc | 960 |
| caggtcaagg aggtcacgca gaatgaaggc accaagacca tcgccaataa cctcaccagc | 1020 |
| accatccagg tgtttacgga ctcggagtac cagctgccgt acgttctcgg ctctgcgcac | 1080 |
| cagggctgcc tccctccgtt cccggcggac gtgttcatga ttccgcaata cggctacctg | 1140 |
| acgctcaaca atggcagcca agccgtggga cgttcatcct tttactgcct ggaatatttc | 1200 |
| ccttctcaga tgctgagaac gggcaacaac tttaccttca gctacacctt tgaggaagtg | 1260 |
| cctttccaca gcagctacgc gcacagccag agccttggac ggctgatgaa tcctctgatt | 1320 |
| gaccagtacc tgtactactt gtctcggact caaacaacag gaggcacggc aaatacgcag | 1380 |
| actctgggct tcagccaagg tgggcctaat acaatggcca atcaggcaaa gaactggctg | 1440 |
| ccaggaccct gttaccgcca acaacgcgtc tcaacgacaa ccgggcaaaa caacaatagc | 1500 |
| aactttgcct ggactgctgg gaccaaatac catctgaatg gaagaaattc attggctaat | 1560 |
| cctggcatcg ctatgcaac acacaaagac gacgaggagc gttttttcc cagtaacggg | 1620 |
| atcctgattt ttggcaaaca aaatgctgcc agagacaatg cggattacag cgatgtcatg | 1680 |
| ctcaccagcg aggaagaaat caaaaccact aaccctgtgg ctacagagga atacggtatc | 1740 |
| gtggcagata acttgcagca gcaaaacacg gctcctcaaa ttggaactgt caacagccag | 1800 |

```
ggggccttac ccggtatggt ctggcagaac cgggacgtgt acctgcaggg tcccatctgg    1860
gccaagattc ctcacacgga cggcaacttc cacccgtctc cgctgatggg cggctttggc    1920
ctgaaacatc ctccgcctca gatcctgatc aagaacacgc ctgtacctgc ggatcctccg    1980
accaccttca accagtcaaa gctgaactct ttcatcacgc aatacagcac cggacaggtc    2040
agcgtggaga tcgagtggga gctgcagaag gaaaacagca agcgctggaa cccggagatc    2100
cagtacactt ccaactatta caagtctaat aatgttgaat ttgctgttaa tactgaaggt    2160
gtatatagtg aaccccgccc cattggcacc agatacctga ctcgtaatct gtaa          2214
```

<210> SEQ ID NO 17
<211> LENGTH: 2205
<212> TYPE: DNA
<213> ORGANISM: Artificial sequence
<220> FEATURE:
<223> OTHER INFORMATION: Recombinant sequence

<400> SEQUENCE: 17

```
atggctgctg acggttatct tccagattgg ctcgaggaca acctttctga aggcattcgt      60
gagtggtggg ctctgaaacc tggagtccct caacccaaag cgaaccaaca acaccaggac     120
aaccgtcggg tcttgtgct tccgggttac aaatacctcg acccggtaa cggactcgac       180 aaaggagagc cggtcaacga ggcggacgcg gcagccctcg aacacgacaa ggcctacgac     240
cagcagctca aggccggaga caacccgtac ctcaagtaca accacgccga cgccgagttc     300
caggagcggc tcaaagaaga tacgtctttt gggggcaacc tcgggcgagc agtcttccag     360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaagaga ctcaatttcg gtcagactgg cgacacagag     540
tcagtcccag accctcaacc aatcggagaa cctcccgcag cccctcagg tgtgggatct      600 cttacaatgg cttcaggtgg tggcgcacca gtggcagaca taacgaagg tgccgatgga     660 gtgggtagtt cctcgggaaa ttggcattgc gattcccaat ggctggggga cagagtcatc     720
accaccagca cccgaacctg ggccctgccc acctacaaca accacctcta caaacaaatt     780
tccagccaat caggagcctc gaacgacaat cactactttg gctacagcac cccttggggg     840
tattttgact tcaacagatt ccactgccac ttttcaccac gtgactggca gcgactcatc     900
aacaacaact ggggattccg gcccaagaga ctcagcttca gctcttcaa catccaggtc     960 aaagaggtta cggacaacaa tggagtcaag accatcgcca taaccttac cagcacggtc    1020 caggtcttca cggactcaga ctatcagctc ccgtacgtgc tcgggtcggc tcacgagggc    1080
tgcctcccgc cgttcccagc ggacgttttc atgattcctc agtacgggta tctgacgctt    1140
aatgatggaa gccaggccgt gggtcgttcg tcctttttact gcctggaata tttcccgtcg    1200
caaatgctaa gaacgggtaa caactttcag ttcagctacg agtttgagaa cgtacctttc    1260
catagcagct acgctcacag ccaaagcctg gaccgactaa tgaatccact catcgaccaa    1320
tacttgtact atctctcaaa gactattaac ggttctggac agaatcaaca aacgctaaaa    1380
ttcagtgtgg ccggacccag caacatggct gtccagggaa gaaactacat acctggaccc    1440
agctaccgac aacaacgtgt ctcaaccact gtgactcaaa acaacaacag cgaatttgct    1500
tggcctggag cttcttcttg ggctctcaat ggacgtaata gcttgatgaa tcctggacct    1560
gctatggcca gccacaaaga aggagaggac cgttttctttc ctttgtctgg atctttaatt    1620
tttggcaaac aaggaactgg aagagacaac gtggatgcgg acaaagtcat gataaccaac    1680
```

```
gaagaagaaa ttaaaactac taacccggta gcaacggagt cctatggaca agtggccaca   1740
aaccaccaga gtgcccaagc acaggcgcag accggctggg ttcaaaacca aggaatactt   1800
ccgggtatgg tttggcagga cagagatgtg tacctgcaag gacccatttg ggccaaaatt   1860
cctcacacgg acggcaactt tcaccttct ccgctgatgg gagggtttgg aatgaaacac    1920
ccgcctcctc agatcctcat caaaaacaca cctgtacctg cggatcctcc aacggccttc   1980
aacaaggaca agctgaactc tttcatcacc cagtattcta ctggccaagt cagcgtggag   2040
atcgagtggg agctgcagaa ggaaaacagc aagcgctgga accccgagat ccagtacacc   2100
tccaactact acaaatctac aagtgtggac tttgctgtta atacagaagg cgtgtactct   2160
gaaccccgcc ccattggcac ccgttacctc acccgtaatc tgtaa                   2205
```

<210> SEQ ID NO 18
<211> LENGTH: 2217
<212> TYPE: DNA
<213> ORGANISM: Artificial sequence
<220> FEATURE:
<223> OTHER INFORMATION: Recombinant sequence

<400> SEQUENCE: 18

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtacctcg gacccttcaa cggactcgac    180 aaggggagc ccgtcaacgc ggcggacgca gcggccctcg agcacgacaa ggcctacgac     240
cagcagctgc aggcgggtga caatccgtac ctgcggtata ccacgccga cgccgagttt    300 caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca acaaccacct ctacaagcaa    780
atctccaacg gacatcgggg aggagccacc aacgacaaca cctacttcgg ctacagcacc    840
cccctggggt attttgactt taacagattc cactgccact tttccaccg tgactggcag     900 cgactcatca caacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca acaacggtag tcaggccgtg gacgctcct ccttctactg cctggaatac     1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
```

-continued

```
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga tttttggcaa acaaaatgct gccagagaca atgcggatta cagcgatgtc    1680
atgctcacca gcgaggaaga aatcaaaacc actaaccctg tggctacaga ggaatacggt    1740
atcgtggcag ataacttgca gcagcaaaac acggctcctc aaattggaac tgtcaacagc    1800 caggggggcct tacccggtat ggtctggcag aaccgggacg tgtacctgca gggtcccatc    1860
tgggccaaga ttcctcacac ggacggcaac ttccacccct ctcccctcat gggtggattc    1920
ggacttaaac atcctccgcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
atccagtaca cctccaacta ctacaaatct acaagtgtgg actttgctgt taatacagaa    2160
ggcgtgtact ctgaaccccg ccccattggc acccgttacc tcacccgtaa tctgtaa       2217
```

<210> SEQ ID NO 19
<211> LENGTH: 2211
<212> TYPE: DNA
<213> ORGANISM: Artificial sequence
<220> FEATURE:
<223> OTHER INFORMATION: Recombinant sequence

<400> SEQUENCE: 19

```
atggctgctg acggttatct tccagattgg ctcgaggaca acctttctga aggcattcga    60
gagtggtggg cgctgcaacc tggagcccct aaacccaagg caaatcaaca acatcaggac    120
aacgctcggg gtcttgtgct tccgggttac aaataccctcg acccggcaa cggactcgac    180 aagggggaac ccgtcaacgc agcggacgcg gcagccctcg agcacgacaa ggcctacgac    240
cagcagctca aggccggtga caaccccctac ctcaagtaca ccacgccga cgccgagttc    300 caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga tcagtctcct caggaaccgg actcatcatc tggtgttggc    480
aaatcgggca acagcctgc cagaaaaaga ctaaatttcg gtcagactgg cgactcagag    540
tcagtcccag accctcaacc tctcggagaa ccaccagcag ccccccacaag tttgggatct    600 aatacaatgg cttcaggcgg tggcgcacca atggcagaca taacgagggg tgccgatgga    660
gtgggtaatt cctcaggaaa ttggcattgc gattcccaat ggctgggcga cagagtcatc    720
accaccagca ccagaacctg gccctgccc acttacaaca accatctcta caagcaaatc    780
tccagccaat caggagcttc aaacgacaac cactactttg gctacagcac cccttggggg    840
tattttgact ttaacagatt ccactgccac ttctcaccac gtgactggca gcgactcatt    900
aacaacaact ggggattccg gcccaagaaa ctcagcttca gctcttcaa catccaagtt    960 aaagaggtca cgcagaacga tggcacgacg actattgcca ataaccttac cagcacggtt    1020
caggtgttta cggactcgga gtatcagctc ccgtacgtgc tcgggtcggc gcaccaaggc    1080
tgtctcccgc cgtttccagc ggacgtcttc atggtccctc agtatggata cctcaccctg    1140
aacaacggaa gtcaagcggt gggacgctca tccttttact gcctggagta cttcccttcg    1200
cagatgctaa ggactggaaa taacttccaa ttcagctata ccttcgagga tgtacctttt    1260
cacagcagct acgctcacag ccagagtttg gatcgcttga tgaatcctct tattgatcag    1320
tatctgtact acctgaacag aacgcaagga acaacctctg gaacaaccaa ccaatcacgg    1380
```

```
ctgctttttta gccaggctgg gcctcagtct atgtctttgc aggccagaaa ttggctacct   1440
gggccctgct accggcaaca gagactttca aagactgcta acgacaacaa caacagtaac   1500
tttccttgga cagcggccag caaatatcat ctcaatggcc gcgactcgct ggtgaatcca   1560
ggaccagcta tggccagtca caaggacgat gaagaaaaat ttttccctat gcacggcaat   1620
ctaatatttg gcaaagaagg gacaacggca agtaacgcag aattagataa tgtaatgatt   1680
acggatgaag aagagattcg taccaccaat cctgtggcaa cagagcagta tggaactgtg   1740
gcaaataact tgcagagctc aaatacagct cccacgacta gaactgtcaa tgatcagggg   1800
gccttacctg gcatggtgtg gcaagatcgt gacgtgtacc ttcaaggacc tatctgggca   1860
aagattcctc acacggatgg acactttcat ccttctcctc tgatgggagg ctttggactg   1920
aaacatccgc ctcctcaaat catgatcaaa aatactccgg taccggcaaa tcctccgacg   1980
actttcagcc cggccaagtt tgcttcattt atcactcagt actccactgg acaggtcagc   2040
gtggaaattg agtgggagct acagaaagaa aacagcaaac gttggaatcc agagattcag   2100
tacacttcca actacaacaa gtctgttaat gtggacttta ctgtagacac taatggtgtt   2160
tatagtgaac ctcgccccat ggcacccgt taccttaccc gtcccctgta a            2211

<210> SEQ ID NO 20
<211> LENGTH: 2211
<212> TYPE: DNA
<213> ORGANISM: Artificial sequence
<220> FEATURE:
<223> OTHER INFORMATION: Recombinant sequence

<400> SEQUENCE: 20
atggctgctg acggttatct tccagattgg ctcgaggaca acctttctga aggcattcga     60
gagtggtggg cgctgcaacc tggagcccct aaacccaagg caaatcaaca acatcaggac    120
aacgctcggg gtcttgtgct tccgggttac aaataccctcg acccggcaa cggactcgac    180 aaggggggaac ccgtcaacgc agcggacgcg gcagccctcg agcacgacaa ggcctacgac    240
cagcagctca aggccggtga caaccccctac ctcaagtaca ccacgccga cgccgagttc    300 caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga tcagtctcct caggaaccgg actcatcatc tggtgttggc    480
aaatcgggca acagcctgc cagaaaagag ctaaatttcg gtcagactgg cgactcagag    540
tcagtcccag accctcaacc tctcggagaa ccaccagcag cccccacaag tttgggatct    600
aatacaatgg cttcaggcgg tggcgcacca atggcagaca ataacgaggg tgccgatgga    660
gtgggtaatt cctcaggaaa ttggcattgc gattcccaat ggctgggcga cagagtcatc    720
accaccagca ccagaacctg ggccctgccc acttacaaca accatctcta caagcaaatc    780
tccagccaat caggagcttc aaacgacaac cactactttg ctacagcac cccttgggg    840 tatttttgact ttaacagatt ccactgccac ttctcaccac gtgactggca gcgactcatt    900
aacaacaact ggggattccg gcccaagaaa ctcagcttca gctcttcaa catccaagtt    960 aaagaggtca cgcagaacga tggcacgacg actattgcca ataaccttac cagcacggtt   1020
caagtgttta cggactcgga gtatcagctc ccgtacgtgc tcgggtcggc gcaccaaggc   1080
tgtctcccgc cgtttccagc ggacgtcttc atggtccctc agtatggata cctcaccctg   1140
aacaacggaa gtcaagcggt gggacgctca tcctttact gcctggagta cttcccttcg   1200
```

```
cagatgctaa ggactggaaa taacttccaa ttcagctata ccttcgagga tgtacctttt    1260
cacagcagct acgctcacag ccagagtttg gatcgcttga tgaatcctct tattgatcag    1320
tatctgtact acctgaacag aacgcaagga acaacctctg gaacaaccaa ccaatcacgg    1380
ctgcttttta gccaggctgg gcctcagtct atgtctttgc aggccagaaa ttggctacct    1440
gggccctgct accggcaaca gagactttca agactgctaa cgacaacaa caacagtaac     1500 tttccttgga cagcggccag caaatatcat ctcaatggcc gcgactcgct ggtgaatcca    1560
ggaccagcta tggccagtca caaggacgat gaagaaaaat tttccctat gcacggcaat     1620 ctaatatttg gcaaagaagg acaacggca agtaacgcag aattagataa tgtaatgatt     1680
acggatgaag aagagattcg taccaccaat cctgtggcaa cagagcagta tggaactgtg    1740
gcaaataact tgcagagctc aaatacagct cccacgacta gaactgtcaa tgatcagggg    1800
gccttacctg gcatggtgtg gcaagatcgt gacgtgtacc ttcaaggacc tatctgggca    1860
aagattcctc acacggatgg acactttcat ccttctcctc tgatgggagg ctttggactg    1920
aaacatccgc ctcctcaaat catgatcaaa atactccgg taccggcaaa tcctccgacg     1980
actttcagcc cggccaagtt tgcttcattt atcactcagt actccactgg acaggtcagc    2040
gtggaaattg agtgggagct acagaaagaa acagcaaac gttggaatcc agagattcag     2100
tacacttcca actacaacaa gtctgttaat gtggacttta ctgtagacac taatggtgtt    2160
tatagtgaac ctcgccccat ggcacccgt taccttaccc gtcccctgta a              2211
```

<210> SEQ ID NO 21
<211> LENGTH: 2217
<212> TYPE: DNA
<213> ORGANISM: Artificial Sequence
<220> FEATURE:
<223> OTHER INFORMATION: Recombinant sequence

<400> SEQUENCE: 21

```
atggctgccg atggttatct tccagattgg ctcgaggaca ctctctctga aggaataaga     60
cagtggtggg cgctgaaacc tggagccccg aagcccaaag ccaaccagca aaagcaggac    120
gacggccggg gtctggtgct tcctggctac aagtacctcg gacccttcaa cggactcgac    180 aaggggagc ccgtcaacgc ggcggatgca gcggccctcg agcacgacaa ggcctacgac     240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag ccaacagcc cgccagaaaa gactcaatt tggtcagac tggcgactca      540 gagtcagttc cagacccctca acctctcgga gaaccaccag cagccccac aagtttggga    600 tctaatacaa tggcttcagg cggtggcgca ccaatggcag acaataacga gggtgccgat    660
ggagtgggta attcctcagg aaattggcat tgcgattccc aatggctggg cgacagagtc    720
atcaccacca gcacccgcac ctgggccttg cccacctaca ataaccacct ctacaagcaa    780
atctccagtg cttcaacggg ggccagcaac gacaaccact acttcggcta cagcaccccc    840
tgggggtatt ttgactttaa ccgcttccac tgccacttct cgccaagaga ctggcaaaga    900
ctcatcaaca acaattgggg attccggccc aagagactca acttcaaact cttcaacatc    960
caagtcaagg aggtcacgac gaatgatggc gtcacgacca tcgccaataa cctcaccagc    1020
accatccagg tgtttacgga ctcggagtac cagctgccgt acgttctcgg ctctgcccac    1080
```

```
cagggctgcc tgcctccgtt cccggcggac gtgttcatga ttccccagta tggataccct    1140
accctgaaca acggaagtca agcggtggga cgctcatcct tttactgcct ggagtacttc    1200
ccttcgcaga tgctaaggac tggaaataac ttccaattca gctataccct cgaggatgta    1260 cctttcaca gcagctacgc tcacagccag agtttggatc gcttgatgaa tcctcttatt    1320
gatcagtatc tgtactacct gaacagaacg caaggaacaa cctctggaac aaccaaccaa    1380
tcacggctgc tttttagcca ggctgggcct cagtctatgt ctttgcaggc cagaaattgg    1440
ctacctgggc cctgctaccg gcaacagaga cttttcaaaga ctgctaacga caacaacaac    1500
agtaactttc cttggacagc agccagcaaa tatcatctca atggccgcga ctcgctggtg    1560
aatccaggac cagctatggc cagtcacaag gacgatgaag aaaaattttt ccctatgcac    1620
ggcaatctaa tatttggcaa agaagggaca acggcaagta acgcagaatt agataatgta    1680
atgattacgg atgaagaaga gattcgtacc accaatcctg tggcaacaga gcagtatgga    1740
actgtggcaa ataacttgca gagctcaaat acagctccca cgactagaac tgtcaatgat    1800
cagggggcct acctggcat ggtgtggcaa gatcgtgacg tgtaccttca ggggcccatc    1860
tgggcaaaga ttccacacac ggacggacat tttcacccct ctccctcat gggtggattc    1920 ggacttaaac accctcctcc gcagattctc atcaagaaca ccccggtacc tgcgaatcct    1980
tcgaccacct tcagtgcggc aaagtttgct tccttcatca cacagtactc cacgggacag    2040
gtcagcgtgg agatcgagtg ggagctgcag aaggaaaaca gcaagcgctg gaacccggag    2100
atccagtaca cttccaacta ttacaagtct aataatgttg aatttgctgt taatactgaa    2160
ggtgtatata gtgaacccgg ccccattggc accagatacc tgactcgtaa tctgtaa     2217

<210> SEQ ID NO 22
<211> LENGTH: 2208
<212> TYPE: DNA
<213> ORGANISM: Artificial Sequence
<220> FEATURE:
<223> OTHER INFORMATION: Recombinant sequence

<400> SEQUENCE: 22
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg acccttcaa cggactcgac    180 aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt ggggggcaacc tcggacagagc agtcttccag    360 gcgaaaaaga gggttcttga acctctgggc ctggttgagg aacctgttaa gacggctccg    420 ggaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg acccccagcc tctcggacag ccaccagcag ccccctctgg tctgggaact    600
aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg ctacagcac ccctggggg    840 tattttgact tcaacagatt ccactgccac ttttcaccac gtgactggca aagactcatc    900
```

```
aacaacaact ggggattccg acccaagaga ctcaacttca agctctttaa cattcaagtc      960
aaagaggtca cgcagaatga cggtacgacg acgattgcca ataaccttac cagcacggtt     1020
caggtgttta ctgactcgga gtaccagctc ccgtacgtcc tcggctcggc gcatcaagga     1080
tgcctcccgc cgttcccagc agacgtcttc atggtgccac agtatggata cctcaccctg     1140
aacaacggga gtcaggcagt aggacgctct tcatttact gcctggagta ctttccttct     1200
cagatgctgc gtaccggaaa caactttacc ttcagctaca cttttgagga cgttcctttc     1260
cacagcagct acgctcacag ccagagtctg daccgtctca tgaatcctct catcgaccag     1320
tacctgtatt acttgagcag aacaaacact ccaagtggaa ccaccacgca gtcaaggctt     1380
cagttttctc aggccggagc gagtgacatt cgggaccagt ctaggaactg gcttcctgga     1440
ccctgttacc gccagcagcg agtatcaaag acatctgcgg ataacaacaa cagtgaatac     1500
tcgtggactg gagctaccaa gtaccacctc aatggcagag actctctggt gaatccgggc     1560
ccggccatgg caagccacaa ggacgatgaa gaaaagtttt tcctcagag cggggttctc     1620
atctttggga agcaaggctc agagaaaaca atgtgtgaca ttgaaaaggt catgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc aggggcccat ctgggcaaag     1860
attccacaca cggacggaca ttttcacccc tctcccctca tgggtggatt cggacttaaa     1920
caccctcctc cacagattct catcaagaac accccggtac ctgcgaatcc ttcgaccacc     1980
ttcagtgcgg caaagtttgc ttccttcatc acacagtact ccacgggaca ggtcagcgtg     2040
gagatcgagt gggagctgca gaaggaaaac agcaaacgct ggaatcccga aattcagtac     2100
acttccaact acaacaagtc tgttaatgtg gactttactg tggacactaa tggcgtgtat     2160
tcagagcctc gccccattgg caccagatac ctgactcgta atctgtaa                  2208
```

<210> SEQ ID NO 23
<211> LENGTH: 2208
<212> TYPE: DNA
<213> ORGANISM: Artificial sequence
<220> FEATURE:
<223> OTHER INFORMATION: Recombinant sequence

<400> SEQUENCE: 23

```
atggctgccg atggttatct tccagattgg ctcgaggaca acctctctga gggcattcgc       60
gagtggtggg cgctgaaacc tggagccccg aagcccaaag ccaaccagca aaagcaggac      120
gacggccggg gtctggtgct tcctggctac aagtacctcg gacccttcaa cggactcgac      180
aaggggagc ccgtcaacgc ggcggacgcc gcggccctcg agcacgacaa ggcctacgac      240
cagcagctgc aggcgggtga caatccgtac ctgcggtata ccacgccga cgccgagttt      300
caggagcgtc tgcaagaaga tacgtctttt ggggcaacc tcgggcgagc agtcttccag      360
gccaaaaaga ggcttcttga acctcttggt ctggttgagg aagcagctaa aacggctcct      420
ggaaagaaga ggcctgtaga gcagtctcct caggaaccgg actcctccgc gggtattggc      480
aaatcgggtg cacagcccgc caaaaagaga ctcaatttcg gtcagactgg cgactcagag      540
tcagtcccag accctcaacc tctcggagaa ccaccagcag cccccacaag tttgggatct      600
aatacaatgg cttcaggcgg tggcgcacca atggcagaca ataacgaagg cgccgacgga      660
gtgggtaatg cctcaggaaa ttggcattgc gattccacat ggctgggcga cagagtcatc      720
accaccagca cccgcacctg ggccttgccc acctacagca accatctcta caagcaaatc      780
```

```
tccagccaat caggagcttc aaacgacaac gactactttg gctacagcac cccttggggg      840
tattttgatt tcaacagatt ccactgccac ttttcaccac gtgactggca aagactcatc      900
aacaacaact ggggattccg acccaagaga ctcaacttca agctctttaa cattcaagtc      960
aaagaggtca cgcagaatga cggtacgacg acgattgcca ataaccttac cagcacggtt     1020
caggtgttta ctgactcgga gtaccagctc ccgtacgtcc tcggctcggc catcaagga      1080 tgcctcccgc cgttcccagc agacgtcttc atggtgccac agtatggata cctcaccctg     1140
aacaacggga gtcaggcagt aggacgctct tcattttact gcctggagta ctttccttct     1200
cagatgctgc gtaccggaaa caactttacc ttcagctaca cttttgagga cgttcctttc     1260
cacagcagct acgctcacag ccagagtctg gaccgtctca tgaatcctct catcgaccag     1320
tacctgtatt acttgagcag aacaaacact ccaagtggaa ccaccacgca gtcaaggctt     1380
cagttttctc aggccggagc gagtgacatt cggaccagt ctaggaactg gcttcctgga      1440
ccctgttacc gccagcagcg agtatcaaag acatctgagg ataacaacaa cagtgaatac     1500
tcgtggactg gagctaccaa gtaccacctc aatggcagag actctctggt gaatccgggc     1560
ccggccatgg caagccacaa ggacgatgaa gaaaagtttt tcctcagag cggggttctc      1620 atctttggga agcaaggctc agagaaaaca aatgtggaca ttgaaaaggt catgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc aggggcccat ctgggcaaag     1860
attccacaca cggacggaca ttttcacccc tctcccctca tgggtggatt cggacttaaa     1920
caccctcctc cacagattct catcaagaac accccggtac ctgcgaatcc ttcgaccacc     1980
ttcagtgcgg caaagtttgc ttccttcatc acacagtact ccacgggaca ggtcagcgtg     2040
gagatcgagt gggagctgca gaaggaaaac agcaaacgct ggaatcccga aattcagtac     2100
acttccaact acaacaagtc tgttaatgtg gactttactg tggacactaa tggcgtgtat     2160
tcagagcctc gccccattgg caccagatac ctgactcgta atctgtaa                  2208
```

<210> SEQ ID NO 24
<211> LENGTH: 2208
<212> TYPE: DNA
<213> ORGANISM: Artificial Sequence
<220> FEATURE:
<223> OTHER INFORMATION: Recombinant sequence

<400> SEQUENCE: 24

```
atggctgccg atggttatct tccagattgg ctcgaggaca acctctctga gggcattcgc       60
gagtggtggg cgctgaaacc tggagccccg aagcccaaag ccaaccagca aaagcaggac      120
gacggccggg gtctggtgct tcctggctac aagtacctcg accccttcaa cggactcgac      180
aagggggagc ccgtcaacgc ggcggacgca gcggccctcg agcacgacaa ggcctacgac      240
cagcagctgc aggcgggtga caatccgtac ctgcggtata ccacgccga cgccgagttc      300 caggagcgtc tgcaagaaga tacgtctttt ggggcaacc tcgggcgagc agtcttccag      360
gccaagaaga gggttctcga acctttggt ctggttgagg aaggtgctaa gacggctcct      420
ggaaagaaac gtccggtaga gcagtcgcca caagagccag actcctcctc gggcattggc      480
aagacaggcc agcagcccgc taaaaagaga ctcaattttg gtcagactgg cgactcagag      540
tcagtcccag accctcaacc tctcggagaa ccaccagcag cccccacaag tttgggatct       600
```

| | |
|---|---|
| aatacaatgg cttcaggcgg tggcgcacca atggcagaca ataacgaggg cgccgacgga | 660 |
| gtgggtaatt cctcgggaaa ttggcattgc gattccacat ggatgggcga cagagtcatc | 720 |
| accaccagca cccgaacctg ggccctgccc acctacaaca accacctcta caaacaaatt | 780 |
| tccagccaat caggagcttc aaacgacaac cactactttg ctacagcac cccttggggg | 840 |
| tattttgact ttaacagatt ccactgccac ttttcaccac gtgactggca gcgactcatt | 900 |
| aacaacaact ggggattccg gcccaagaaa ctcaacttca agctctttaa catccaggtc | 960 |
| aaggaggtca cgcagaatga aggcaccaag accatcgcca ataacctcac cagcaccatc | 1020 |
| caggtgttta cggactcgga gtaccagctg ccgtacgttc tcggctctgc ccaccagggc | 1080 |
| tgcctgcctc cgttcccggc ggacgtgttc atgattcccc agtacggcta cctaacactc | 1140 |
| aacaacggta gtcaggccgt gggacgctcc tccttctact gcctggaata ctttccttcg | 1200 |
| cagatgctga gaaccggcaa caacttccag tttacttaca ccttcgagga cgtgcctttc | 1260 |
| cacagcagct acgcccacag ccagagcttg gaccggctga tgaatcctct gattgaccag | 1320 |
| tacctgtatt acttgtctcg gactcaaaca acaggaggca cgacaaatac gcagactctg | 1380 |
| ggcttcagcc aaggtgggcc taatacaatg gccaatcagg caaagaactg gctgcctgga | 1440 |
| ccctgttacc gccagcagcg agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt ttcctcagag cggggttctc | 1620 |
| atctttggga agcaaggctc agagaaaaca aatgtggaca ttgaaaaggt tatgattaca | 1680 |
| gacgaagagg aaatcaggac aaccaatccc gtggctacgg agcagtatgg ttctgtatct | 1740 |
| accaacctcc agagaggcaa cagacaagca gctaccgcag atgtcaacac acagggcgtt | 1800 |
| cttccaggca tggtctggca ggacagagat gtgtaccttc agggtcccat ttgggccaaa | 1860 |
| attcctcaca cagatggaca ctttcacccg tcccctctta tgggcggctt tggactcaag | 1920 |
| aacccgcctc ctcagatcct catcaaaaac acgcctgttc ctgcgaatcc tccggcagag | 1980 |
| ttttcagcta caaagtttgc ttcattcatc acccaatact ccacaggaca agtgagtgtg | 2040 |
| gaaattgaat gggagctgca gaaagaaaac agcaagcgct ggaatcccga agtgcagtac | 2100 |
| acatccaatt atgcaaaatc tgccaacgtt gattttactg tggacactaa tggcgtgtat | 2160 |
| tcagagcctc gccccattgg caccagatac ctcacccgta atctgtaa | 2208 |

<210> SEQ ID NO 25
<211> LENGTH: 2214
<212> TYPE: DNA
<213> ORGANISM: Artificial Sequence
<220> FEATURE:
<223> OTHER INFORMATION: Recombinant sequence

<400> SEQUENCE: 25

| | |
|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg gacccttcaa cggactcgac | 180 |
| aaggggagc ccgtcaacgc ggcggatgca gcggccctcg agcacgacaa ggcctacgac | 240 |
| cagcagctca agcgggtga caatccgtac ctgcggtata accgccga cgccgagttt | 300 |
| caggagcgtc tgcaagaaga tacgtctttt gggggcaacc tcgggcgagc agtcttccag | 360 |
| gccaagaaga gggttctcga accttttggt ctggttgagg aaggtgctaa gacggctcct | 420 |
| ggaaagaaac gtccggtaga gcagtcgcca caagagccag actcctcctc gggcattggc | 480 |

| | | |
|---|---|---|
| aagacaggcc agcagcctgc aagaaaaaga ttgaattttg gtcagactgg agacgcagac | 540 |
| tcagtacctg accccagcc tctcggacag ccaccagcag cccctctgg tctgggaact | 600 |
| aatacgatgg ctacaggcag tggcgcacca atggcagaca taacgaggg cgccgacgga | 660 |
| gtgggtaatt cctcgggaaa ttggcattgc gattcccaat ggctggggga cagagtcatc | 720 |
| accaccagca cccgaacctg ggccctgccc acctacaaca atcacctcta caagcaaatc | 780 |
| tccaacagca catctggagg atcttcaaat gacaacgcct acttcggcta cagcaccccc | 840 |
| tgggggtatt ttgatttcaa cagattccac tgccatttct caccacgtga ctggcagcga | 900 |
| ctcatcaaca caattgggg attccggccc aagagactca acttcaagct cttcaacatc | 960 |
| caggtcaagg aggtcacgca gaatgaaggc accaagacca tcgccaataa cctcaccagc | 1020 |
| accatccagg tgtttacgga ctcggagtac cagctgccgt acgttctcgg ctctgcccac | 1080 |
| cagggctgcc tgcctccgtt cccggcggac gtgttcatga ttccccagta cggctaccta | 1140 |
| acactcaaca acgtagtca ggccgtggga cgctcctcct tctactgcct ggaatacttt | 1200 |
| ccttcgcaga tgctgagaac cggcaacaac ttccagttta cttacacctt cgaggacgtg | 1260 |
| cctttccaca gcagctacgc ccacagccag agcttggacc ggctgatgaa tcctctgatt | 1320 |
| gaccagtacc tgtactactt gtctcggact caaacaacag gaggcacgac aaatacgcag | 1380 |
| actctgggct tcagccaagg tgggcctaat acaatggcca atcaggcaaa gaactggctg | 1440 |
| ccaggaccct gttaccgcca gcagcgagta tcaaagacat ttgcggataa caacaacagt | 1500 |
| gaatactcgt ggactggagc taccaagtac cacctcaatg gcagagactc tctggtgaat | 1560 |
| ccgggcccgg ccatggcaag ccacaaggac gatgaagaaa agttttttcc tcagagcggg | 1620 |
| gttctcatct ttgggaagca aggctcgag aaaacaaatg tggacattga aaaggtcatg | 1680 |
| attacagacg aagaggaaat caggacaacc aatcccgtgg ctacggagca gtatggttct | 1740 |
| gtatctacca acctccagag aggcaacaga caagcagcta ccgcagatgt caacacacaa | 1800 |
| ggcgttcttc caggcatggt ctggcaggac agagatgtgt accttcaggg gcccatctgg | 1860 |
| gcaaagattc cacacacgga cggacatttt cacccctctc ccctcatggg tggattcgga | 1920 |
| cttaaacacc ctccgcctca gatcctgatc aagaacacgc ctgtacccgc ggatcctccg | 1980 |
| accaccttca accagtcaaa gctgaactct ttcatcaccc agtattctac tggccaagtc | 2040 |
| agcgtggaga tcgagtggga gctgcagaag gaaaacagca agcgctggaa ccccgagatc | 2100 |
| cagtacacct ccaactacta caaatctaca agtgtggact tgctgttaa tacagaaggc | 2160 |
| gtgtactctg aaccccgccc cattggcacc cgttacctca cccgtaatct gtaa | 2214 |

<210> SEQ ID NO 26
<211> LENGTH: 2217
<212> TYPE: DNA
<213> ORGANISM: Artificial Sequence
<220> FEATURE:
<223> OTHER INFORMATION: Recombinant sequence

<400> SEQUENCE: 26

| | | |
|---|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg gacccttcaa cggactcgac | 180 |
| aaggggagc ccgtcaacgc ggcggatgca acggccctcg agcacgacaa ggcctacgac | 240 |
| cagcagctgc aggcgggtga caatccgtac ctgcggtata accacgccga cgccgagttt | 300 |

-continued

| | |
|---|---|
| caggagcgtc tgcaagaaga tacgtctttt gggggcaacc tcgggcgagc agtcttccag | 360 |
| gccaagaagc gggttctcga acctctcggt ctggttgagg aaggcgctaa gacggctcct | 420 |
| ggaaagaaga gaccggtaga gccatcaccc cagcgttctc cagactcctc tacgggcatc | 480 |
| ggcaagaaag ccaacagcc cgccagaaaa agactcaatt ttggtcagac tggcgactca | 540 |
| gagtcagttc cagaccctca acctctcgga gaaccaccag cagccccac aagtttggga | 600 |
| tctaatacaa tggcttcagg cggtggcgca ccaatggcag acaataacga gggtgccgat | 660 |
| ggagtgggta attcctcagg aaattggcat tgcgattccc aatggctggg cgacagagtc | 720 |
| atcaccacca gcacccgcac ctgggccttg cccacctaca ataaccacct ctacaagcaa | 780 |
| atctccagtg cttcaacggg ggccagcaac gacaaccact acttcggcta cagcacccc | 840 |
| tgggggtatt ttgactttaa ccgcttccac tgccacttct cgccaagaga ctggcaaaga | 900 |
| ctcatcaaca acaattgggg attccggccc aagagactca acttcaaact cttcaacatc | 960 |
| caagtcaagg aggtcacgac gaatgatggc gtcacgacca tcgccaataa cctcaccagc | 1020 |
| accatccagg tgtttacgga ctcggagtac cagctgccgt acgttctcgg ctctgcccac | 1080 |
| cagggctgcc tgcctccgtt cccggcggac gtgttcatga ttccccagta tggataccct | 1140 |
| accctgaaca acgaagtca agcggtggga cgctcatcct tttactgcct ggagtacttc | 1200 |
| ccttcgcaga tgctaaggac tggaaataac ttccaattca gctataccct cgaggatgta | 1260 |
| ccttttcaca gcagctacgc tcacagccag agtttggatc gcttgatgaa tcctcttatt | 1320 |
| gatcagtatc tgtactacct gaacagaacg caaggaacaa cctctggaac aaccaaccaa | 1380 |
| tcacggctgc ttttagcca ggctgggcct cagtctatgt ctttgcaggc cagaaattgg | 1440 |
| ctacctgggc cctgctaccg gcaacagaga ctttcaaaga ctgctaacga caacaacaac | 1500 |
| agtaactttc cttggacagc agccagcaaa tatcatctca atggccgcga ctcgctggtg | 1560 |
| aatccaggac cagctatggc cagtcacaag gacgatgaag aaaaattttt ccctatgcac | 1620 |
| ggcaatctaa tatttggcaa agaagggaca acggcaagta acgcagaatt agataatgta | 1680 |
| atgattacgg atgaagaaga gattcgtacc accaatcctg tggcaacaga gcagtatgga | 1740 |
| actgtggcaa ataacttgca gagctcaaat acagctccca cgactagaac tgtcaatgat | 1800 |
| caggggggcct tacctggcat ggtgtggcaa gatcgtgacg tgtaccttca ggggcccatc | 1860 |
| tgggcaaaga ttccacacac ggacggacat tttcacccct ctcccctcat gggtggattc | 1920 |
| ggacttaaac accctcctcc gcagattctc atcaagaaca ccccggtacc tgcgaatcct | 1980 |
| tcgaccacct tcagtgcggc aaagtttgct tccttcatca cacagtactc cacgggacag | 2040 |
| gtcagcgtgg agatcgagtg ggagctgcag aaggaaaaca gcaagcgctg gaacccggag | 2100 |
| atccagtaca cttccaacta ttacaagtct aataatgttg aatttgctgt taatactgaa | 2160 |
| ggtgtatata gtgaaccccg ccccattggc accagatacc tgactcgtaa tctgtaa | 2217 |

<210> SEQ ID NO 27
<211> LENGTH: 2208
<212> TYPE: DNA
<213> ORGANISM: Artificial Sequence
<220> FEATURE:
<223> OTHER INFORMATION: Recombinant sequence

<400> SEQUENCE: 27

| | |
|---|---|
| atggctgccg atggttatct tccagattgg ctcgaggaca accttagtga aggaattcgc | 60 |
| gagtggtggg acttgaaacc tggagccccg aagcccaaag ccaaccagca aaagcaggac | 120 |
| gacggccggg gtctggtgct tcctggctac aagtacctcg gacccttcaa cggactcgac | 180 |

```
aagggggagc cgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggtgctaa gacggctcct    420
ggaaagaaac gtccggtaga gcagtcgcca aagagccag actcctcctc gggcattggc     480
aagacaggcc agcagcccgc taaaaagaga ctcaattttg gtcagactgg cgactcagag    540
tcagtccccg acccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagagtcatc    720
accaccagca cccgaacctg ggccctgccc acctacaaca ccacctcta caaacaaatt     780 tccagccaat caggagcctc gaacgacaat cactactttg gctacagcac cccttggggg    840
tattttgatt tcaacagatt ccactgccac ttttcaccac gtgactggca gcgactcatc    900
aacaacaatt ggggattccg gcccaagaga ctcagcttca agctcttcaa catccaggtc    960
aaggaggtca cgcagaatga aggcaccaag accatcgcca ataaccttac cagcacggtt   1020 caagtgtttta cggactcgga gtatcagctc ccgtacgtgc tcggctcggc catcaagga    1080 tgcctcccgc cgttcccagc agacgtcttc atggtgccac agtatggata cctcaccctg   1140
aacaacggga gtcaggcagt aggacgctct tcattttact gcctggagta cttttccttct  1200 cagatgctgc gtaccggaaa caactttacc ttcagctaca cttttgagga cgttcctttc   1260
cacagcagct acgctcacag ccagagtctg gaccgtctca tgaatcctct gattgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggactatgaa gaaaagtttt tcctcagag cggggttctc    1620 atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca tttttcaccccg tctccgctga tgggcggctt tggcctgaaa    1920
catcctccgc tcagatcct gatcaagaac acgcctgtac ctgcggatcc tccgaccacc    1980
ttcaaccagt caaagctgaa ctctttcatc actcagtatt ctactggcca agtcagcgtg   2040
gagatcgagt gggagctgca gaaggaaaac agcaagcgct ggaaccccga gatccagtac    2100
acctccaact actacaaatc tacaagtgtg gactttgctg ttaatacaga aggcgtgtac    2160
tctgaacccc gccccattgg caccgttac ctcacccgta atctgtaa                  2208
```

<210> SEQ ID NO 28
<211> LENGTH: 2214
<212> TYPE: DNA
<213> ORGANISM: Artificial Sequence
<220> FEATURE:
<223> OTHER INFORMATION: Recombinant sequence

<400> SEQUENCE: 28

| | |
|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg acccttcaa cggactcgac | 180 |
| aaggggagc ccgtcaacgc ggcggatgca gcggccctcg agcacgacaa ggcctacgac | 240 |
| cagcagctca agcgggtga caatccgtac ctgcggtata ccacgccga cgccgagttt | 300 |
| caggagcgtc tgcaagaaga tacgtctttt gggggcaacc tcgggcgagc agtcttccag | 360 |
| gccaagaaga gggttctcga accttttggt ctggttgagg aaggtgctaa gacggctcct | 420 |
| ggaaagaaac gtccggtaga gcagtcgcca aagagccag actcctcctc gggcattggc | 480 |
| aagacaggcc agcagcctgc aagaaaaaga ttgaattttg gtcagactgg agacgcagac | 540 |
| tcagtacctg accccagcc tctcggacag ccaccagcag ccccctctgg tctgggaact | 600 |
| aatacgatgg ctacaggcag tggcgcacca atggcagaca taacgagg cgccgacgga | 660 |
| gtgggtaatt cctcgggaaa ttggcattgc gattcccaat ggctggggga cagagtcatc | 720 |
| accaccagca cccgaacctg ggccctgccc acctacaaca atcacctcta caagcaaatc | 780 |
| tccaacagca catctggagg atcttcaaat gacaacgcct acttcggcta cagcaccccc | 840 |
| tgggggtatt ttgatttcaa cagattccac tgccatttct caccacgtga ctggcagcga | 900 |
| ctcatcaaca caattgggg attccggccc aagagactca acttcaagct cttcaacatc | 960 |
| caggtcaagg aggtcacgca gaatgaaggc accaagacca tcgccaataa cctcaccagc | 1020 |
| accatccagg tgtttacgga ctcggagtac cagctgccgt acgttctcgg ctctgcccac | 1080 |
| cagggctgcc tgcctccgtt cccggcgac gtgttcatga ttccccagta cggctaccta | 1140 |
| acactcaaca acggtagtca ggccgtggga cgctcctcct tctactgcct ggaatacttt | 1200 |
| ccttcgcaga tgctgagaac cggcaacaac ttcagttta cttacacctt cgaggacgtg | 1260 |
| cctttccaca gcagctacgc ccacagccag agcttggacc ggctgatgaa tcctctgatt | 1320 |
| gaccagtacc tgtactactt gtctcggact caaacaacag gaggcacgac aaatacgcag | 1380 |
| actctgggct tcagccaagg tgggcctaat acaatggcca atcaggcaaa gaactggctg | 1440 |
| ccaggaccct gttaccgcca gcagcgagta tcaaagacat ttgcggataa caacaacagt | 1500 |
| gaatactcgt ggactggagc taccaagtac cacctcaatg gcagagactc tctggtgaat | 1560 |
| ccgggcccgg ccatggcaag ccacaaggac gatgaagaaa agttttttcc tcagagcggg | 1620 |
| gttctcatct ttgggaagca aggctcagag aaaacaaatg tggacattga aaaggtcatg | 1680 |
| attacagacg aagaggaaat caggacaacc aatcccgtgg ctacgagca gtatggttct | 1740 |
| gtatctacca acctccagag aggcaacaga caagcagcta ccgcagatgt caacacacaa | 1800 |
| ggcgttcttc caggcatggt ctggcaggac agagatgtgt accttcaggg gcccatctgg | 1860 |
| gcaaagattc cacacacgga cggacatttt cacccctctc ccctcatggg tggattcgga | 1920 |
| cttaaacacc ctccgcctca gatcctgatc aagaacacgc ctgtacccgc ggatcctccg | 1980 |
| accaccttca accagtcaaa gctgaactct ttcatcaccc agtattctac tggccaagtc | 2040 |
| agcgtggaga tcgagtggga gctgcagaag gaaaacagca gcgctggaa ccccgagatc | 2100 |
| cagtacacct ccaactacta caaatctaca agtgtggact tgctgttaa tacagaaggc | 2160 |
| gtgtactctg aaccccgccc cattggcacc cgttacctca cccgtaatct gtaa | 2214 |

<210> SEQ ID NO 29
<211> LENGTH: 737
<212> TYPE: PRT
<213> ORGANISM: Artificial sequence
<220> FEATURE:
<223> OTHER INFORMATION: Recombinant sequence

<400> SEQUENCE: 29

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ala Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400
```

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Ala Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Ser Asn Gly Ile Leu Ile Phe
    530                 535                 540

Gly Lys Gln Asn Ala Ala Arg Asp Asn Ala Asp Tyr Ser Asp Val Met
545                 550                 555                 560

Leu Thr Ser Glu Glu Ile Lys Thr Thr Asn Pro Val Ala Thr Glu
                565                 570                 575

Glu Tyr Gly Ile Val Ala Asp Asn Leu Gln Gln Gln Asn Thr Ala Pro
            580                 585                 590

Gln Ile Gly Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Asn Asn Val Glu Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 30
<211> LENGTH: 736
<212> TYPE: PRT
<213> ORGANISM: Artificial sequence
<220> FEATURE:
<223> OTHER INFORMATION: Recombinant sequence

<400> SEQUENCE: 30

Met Ala Ala Asp Gly Tyr Leu Pro Asp Trp Leu Glu Asp Asn Leu Ser
1               5                   10                  15

-continued

```
Glu Gly Ile Arg Glu Trp Trp Asp Leu Lys Pro Gly Ala Pro Lys Pro
             20                  25                  30
Lys Ala Asn Gln Gln Lys Gln Asp Asp Gly Arg Gly Leu Val Leu Pro
         35                  40                  45
Gly Tyr Lys Tyr Leu Gly Pro Phe Asn Gly Leu Asp Lys Gly Glu Pro
     50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Gln Phe Thr Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Ser Arg
```

```
                435                 440                 445
Thr Gln Thr Thr Gly Gly Thr Ala Asn Thr Gln Thr Leu Gly Phe Ser
        450                 455                 460
Gln Gly Gly Pro Asn Thr Met Ala Asn Gln Ala Lys Asn Trp Leu Pro
465                 470                 475                 480
Gly Pro Cys Tyr Arg Gln Arg Val Ser Thr Thr Gly Gln Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
                515                 520                 525
Asp Asp Glu Asp Lys Phe Phe Pro Met Ser Gly Val Met Ile Phe Gly
        530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
                580                 585                 590
Thr Gly Asp Val His Ala Met Gly Ala Leu Pro Gly Met Val Trp Gln
                595                 600                 605
Asp Arg Asp Val Tyr Leu Gln Gly Pro Ile Trp Ala Lys Ile Pro His
        610                 615                 620
Thr Asp Gly His Phe His Pro Ser Pro Leu Met Gly Gly Phe Gly Leu
625                 630                 635                 640
Lys Asn Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Val Gln Tyr Thr Ser Asn
        690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 31
<211> LENGTH: 736
<212> TYPE: PRT
<213> ORGANISM: Artificial sequence
<220> FEATURE:
<223> OTHER INFORMATION: Recombinant sequence

<400> SEQUENCE: 31

Met Ala Ala Asp Gly Tyr Leu Pro Asp Trp Leu Glu Asp Asn Leu Ser
1               5                   10                  15
Glu Gly Ile Arg Glu Trp Trp Ala Leu Gln Pro Gly Ala Pro Lys Pro
                20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
        50                  55                  60
Val Asn Ala Ala Asp Ala Ala Ala Leu Glu His Asp Lys Ala Tyr Asp
```

```
                65                  70                  75                  80
        Gln Gln Leu Lys Ala Gly Asp Asn Pro Tyr Leu Lys Tyr Asn His Ala
                            85                  90                  95

Asp Ala Glu Phe Gln Glu Arg Leu Lys Glu Asp Thr Ser Phe Gly Gly
                        100                 105                 110

Asn Leu Gly Arg Ala Val Phe Gln Ala Lys Lys Arg Leu Leu Glu Pro
                    115                 120                 125

Leu Gly Leu Val Glu Glu Ala Lys Thr Ala Pro Gly Lys Lys Arg
        130                 135                 140

Pro Val Asp Gln Ser Pro Gln Glu Pro Asp Ser Ser Gly Val Gly
        145                 150                 155                 160

Lys Ser Gly Lys Gln Pro Ala Arg Lys Arg Leu Asn Phe Gly Gln Thr
                        165                 170                 175

Gly Asp Ser Glu Ser Val Pro Asp Pro Gln Pro Leu Gly Glu Pro Pro
                    180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
        210                 215                 220

Ser Gly Asn Trp His Cys Asp Ser Gln Trp Leu Gly Asp Arg Val Ile
        225                 230                 235                 240

Thr Thr Ser Thr Arg Thr Trp Ala Leu Pro Thr Tyr Asn Asn His Leu
                        245                 250                 255

Tyr Lys Gln Ile Ser Ser Gln Ser Gly Ala Ser Asn Asp Asn His Tyr
                    260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
        305                 310                 315                 320

Lys Glu Val Thr Gln Asn Asp Gly Thr Thr Thr Ile Ala Asn Asn Leu
                        325                 330                 335

Thr Ser Thr Val Gln Val Phe Thr Asp Ser Glu Tyr Gln Leu Pro Tyr
                    340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
        385                 390                 395                 400

Gln Met Leu Arg Thr Gly Asn Asn Phe Gln Phe Ser Tyr Thr Phe Glu
                        405                 410                 415

Asp Val Pro Phe His Ser Ser Tyr Ala His Ser Gln Ser Leu Asp Arg
                    420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
        450                 455                 460

Gln Ala Gly Pro Gln Ser Met Ser Leu Gln Ala Arg Asn Trp Leu Pro
        465                 470                 475                 480

Gly Pro Cys Tyr Arg Gln Gln Arg Leu Ser Lys Thr Ala Asn Asp Asn
                        485                 490                 495
```

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735

<210> SEQ ID NO 32
<211> LENGTH: 736
<212> TYPE: PRT
<213> ORGANISM: Artificial sequence
<220> FEATURE:
<223> OTHER INFORMATION: Recombinant sequence

<400> SEQUENCE: 32

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

```
Leu Gly Leu Val Glu Glu Ala Ala Lys Thr Ala Pro Gly Lys Lys Arg
        130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Leu Gly Glu Pro
                180                 185                 190
Pro Ala Thr Pro Ala Ala Val Gly Pro Thr Thr Met Ala Ser Gly Gly
                195                 200                 205
Gly Ala Pro Met Ala Asp Asn Asn Glu Gly Ala Asp Gly Val Gly Asn
        210                 215                 220
Ser Ser Gly Asn Trp His Cys Asp Ser Gln Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Gln Ser Gly Ala Ser Asn Asp Asn His
                260                 265                 270
Tyr Phe Gly Tyr Ser Thr Pro Trp Gly Tyr Phe Asp Phe Asn Arg Phe
                275                 280                 285
His Cys His Phe Ser Pro Arg Asp Trp Gln Arg Leu Ile Asn Asn Asn
        290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
                355                 360                 365
Asp Val Phe Met Ile Pro Gln Tyr Gly Tyr Leu Thr Leu Asn Asn Gly
        370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Ser Arg
                435                 440                 445
Thr Asn Thr Pro Ser Gly Thr Thr Thr Gln Ser Arg Leu Gln Phe Ser
        450                 455                 460
Gln Ala Gly Ala Ser Asp Ile Arg Asp Gln Ser Arg Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
                515                 520                 525
Asp Asp Glu Asp Lys Phe Phe Pro Met Ser Gly Val Met Ile Phe Gly
        530                 535                 540
```

-continued

```
Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Phe Gln Ser Ser Thr Asp Pro Ala
        580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 33
<211> LENGTH: 736
<212> TYPE: PRT
<213> ORGANISM: Artificial sequence
<220> FEATURE:
<223> OTHER INFORMATION: Recombinant sequence

<400> SEQUENCE: 33

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175
```

```
Thr Gly Asp Ser Glu Ser Val Pro Asp Pro Gln Pro Leu Gly Glu Pro
            180                 185                 190

Pro Ala Thr Pro Ala Ala Val Gly Pro Thr Thr Met Ala Ser Gly Gly
        195                 200                 205

Gly Ala Pro Met Ala Asp Asn Asn Glu Gly Ala Asp Gly Val Gly Asn
        210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
        260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
        340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Ser Arg
        435                 440                 445

Thr Asn Thr Pro Ser Gly Thr Thr Thr Gln Ser Arg Leu Gln Phe Ser
450                 455                 460

Gln Ala Gly Ala Ser Asp Ile Arg Asp Gln Ser Arg Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
        580                 585                 590

Thr Gly Asp Val His Val Met Gly Ala Leu Pro Gly Met Val Trp Gln
```

```
                595                 600                 605
Asp Arg Asp Val Tyr Leu Gln Gly Pro Ile Trp Ala Lys Ile Pro His
    610                 615                 620

Thr Asp Gly His Phe His Pro Ser Pro Leu Met Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 34
<211> LENGTH: 736
<212> TYPE: PRT
<213> ORGANISM: Artificial sequence
<220> FEATURE:
<223> OTHER INFORMATION: Recombinant sequence

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Gln Leu Gly Asp Arg Val Ile Thr
```

```
                225                 230                 235                 240

Thr Ser Thr Arg Thr Trp Ala Leu Pro Thr Tyr Asn Asn His Leu Tyr
                           245                 250                 255

Lys Gln Ile Ser Asn Gly Thr Ser Gly Gly Ala Thr Asn Asp Asn Thr
                           260                 265                 270

Tyr Phe Gly Tyr Ser Thr Pro Trp Gly Tyr Phe Asp Phe Asn Arg Phe
                           275                 280                 285

His Cys His Phe Ser Pro Arg Asp Trp Gln Arg Leu Ile Asn Asn Asn
                           290                 295                 300

Trp Gly Phe Arg Pro Lys Arg Leu Ser Phe Lys Leu Phe Asn Ile Gln
           305                 310                 315                 320

Val Lys Glu Val Thr Gln Asn Glu Gly Thr Lys Thr Ile Ala Asn Asn
                           325                 330                 335

Leu Thr Ser Thr Ile Gln Val Phe Thr Asp Ser Glu Tyr Gln Leu Pro
                           340                 345                 350

Tyr Val Leu Gly Ser Ala His Gln Gly Cys Leu Pro Pro Phe Pro Ala
                           355                 360                 365

Asp Val Phe Met Ile Pro Gln Tyr Gly Tyr Leu Thr Leu Asn Asn Gly
                           370                 375                 380

Ser Gln Ala Val Gly Arg Ser Ser Phe Tyr Cys Leu Glu Tyr Phe Pro
           385                 390                 395                 400

Ser Gln Met Leu Arg Thr Gly Asn Asn Phe Thr Phe Ser Tyr Thr Phe
                           405                 410                 415

Glu Glu Val Pro Phe His Ser Ser Tyr Ala His Ser Gln Ser Leu Asp
                           420                 425                 430

Arg Leu Met Asn Pro Leu Ile Asp Gln Tyr Leu Tyr Tyr Leu Ser Arg
                           435                 440                 445

Thr Gln Thr Thr Gly Gly Thr Ala Asn Thr Gln Thr Leu Gly Phe Ser
                           450                 455                 460

Gln Gly Gly Pro Asn Thr Met Ala Asn Gln Ala Lys Asn Trp Leu Pro
           465                 470                 475                 480

Gly Pro Cys Tyr Arg Gln Gln Arg Val Ser Thr Thr Gly Gln Asn
                           485                 490                 495

Asn Asn Ser Asn Phe Ala Trp Thr Ala Gly Thr Lys Tyr His Leu Asn
                           500                 505                 510

Gly Arg Asn Ser Leu Ala Asn Pro Gly Ile Ala Met Ala Thr His Lys
                           515                 520                 525

Asp Asp Glu Glu Arg Phe Phe Pro Ser Asn Gly Ile Leu Ile Phe Gly
                           530                 535                 540

Lys Gln Asn Ala Ala Arg Asp Asn Ala Asp Tyr Ser Asp Val Met Leu
           545                 550                 555                 560

Thr Ser Glu Glu Glu Ile Lys Thr Thr Asn Pro Val Ala Thr Glu Glu
                           565                 570                 575

Tyr Gly Ile Val Ala Asp Asn Leu Gln Gln Gln Asn Thr Ala Pro Gln
                           580                 585                 590

Ile Gly Thr Val Asn Ser Gln Gly Ala Leu Pro Gly Met Val Trp Gln
                           595                 600                 605

Asn Arg Asp Val Tyr Leu Gln Gly Pro Ile Trp Ala Lys Ile Pro His
                           610                 615                 620

Thr Asp Gly Asn Phe His Pro Ser Pro Leu Met Gly Gly Phe Gly Leu
           625                 630                 635                 640

Lys His Pro Pro Pro Gln Ile Leu Ile Lys Asn Thr Pro Val Pro Ala
                           645                 650                 655
```

-continued

Asp Pro Pro Thr Thr Phe Asn Gln Ser Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 35
<211> LENGTH: 737
<212> TYPE: PRT
<213> ORGANISM: Artificial sequence
<220> FEATURE:
<223> OTHER INFORMATION: Recombinant sequence

<400> SEQUENCE: 35

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ala Thr Asn Asp Asn
            260                 265                 270

Thr Tyr Phe Gly Tyr Ser Thr Pro Trp Gly Tyr Phe Asp Phe Asn Arg
        275                 280                 285

-continued

```
Phe His Cys His Phe Ser Pro Arg Asp Trp Gln Arg Leu Ile Asn Asn
    290                 295                 300
Asn Trp Gly Phe Arg Pro Lys Arg Leu Ser Phe Lys Leu Phe Asn Ile
305                 310                 315                 320
Gln Val Lys Glu Val Thr Gln Asn Glu Gly Thr Lys Thr Ile Ala Asn
                325                 330                 335
Asn Leu Thr Ser Thr Ile Gln Val Phe Thr Asp Ser Glu Tyr Gln Leu
                340                 345                 350
Pro Tyr Val Leu Gly Ser Ala His Gln Gly Cys Leu Pro Pro Phe Pro
                355                 360                 365
Ala Asp Val Phe Met Ile Pro Gln Tyr Gly Tyr Leu Thr Leu Asn Asn
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Thr Phe Ser Tyr Thr
                405                 410                 415
Phe Glu Glu Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
    435                 440                 445
Arg Thr Gln Thr Thr Gly Gly Thr Ala Asn Thr Gln Thr Leu Gly Phe
    450                 455                 460
Ser Gln Gly Gly Pro Asn Thr Met Ala Asn Gln Ala Lys Asn Trp Leu
465                 470                 475                 480
Pro Gly Pro Cys Tyr Arg Gln Gln Arg Val Ser Thr Thr Thr Gly Gln
                485                 490                 495
Asn Asn Asn Ser Asn Phe Ala Trp Thr Ala Gly Thr Lys Tyr His Leu
                500                 505                 510
Asn Gly Arg Asn Ser Leu Ala Asn Pro Gly Ile Ala Met Ala Thr His
    515                 520                 525
Lys Asp Asp Glu Glu Arg Phe Phe Pro Ser Asn Gly Ile Leu Ile Phe
    530                 535                 540
Gly Lys Gln Asn Ala Ala Arg Asp Asn Ala Asp Tyr Ser Asp Val Met
545                 550                 555                 560
Leu Thr Ser Glu Glu Glu Ile Lys Thr Thr Asn Pro Val Ala Thr Glu
                565                 570                 575
Glu Tyr Gly Ile Val Ala Asp Asn Leu Gln Gln Gln Asn Thr Ala Pro
                580                 585                 590
Gln Ile Gly Thr Val Asn Ser Gln Gly Ala Leu Pro Gly Met Val Trp
    595                 600                 605
Gln Asn Arg Asp Val Tyr Leu Gln Gly Pro Ile Trp Ala Lys Ile Pro
    610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asp Pro Pro Thr Thr Phe Asn Gln Ser Lys Leu Asn Ser Phe Ile
                660                 665                 670
Thr Gln Tyr Ser Thr Gly Gln Val Ser Val Glu Ile Glu Trp Glu Leu
    675                 680                 685
Gln Lys Glu Asn Ser Lys Arg Trp Asn Pro Glu Ile Gln Tyr Thr Ser
    690                 695                 700
```

```
Asn Tyr Tyr Lys Ser Asn Asn Val Glu Phe Ala Val Asn Thr Glu Gly
705                 710                 715                 720

Val Tyr Ser Glu Pro Arg Pro Ile Gly Thr Arg Tyr Leu Thr Arg Asn
            725                 730                 735

Leu
```

<210> SEQ ID NO 36
<211> LENGTH: 736
<212> TYPE: PRT
<213> ORGANISM: Artificial sequence
<220> FEATURE:
<223> OTHER INFORMATION: Recombinant sequence

<400> SEQUENCE: 36

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Thr Pro Ala Ala Val Gly Pro Thr Thr Met Ala Ser Gly Gly
        195                 200                 205

Gly Ala Pro Met Ala Asp Asn Asn Glu Gly Ala Asp Gly Val Gly Asn
    210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
```

```
                    325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
                355                 360                 365
Asp Val Phe Met Ile Pro Gln Tyr Gly Tyr Leu Thr Leu Asn Asn Gly
                370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Ser Arg
                435                 440                 445
Thr Asn Thr Pro Ser Gly Thr Thr Thr Gln Ser Arg Leu Gln Phe Ser
                450                 455                 460
Gln Ala Gly Ala Ser Asp Ile Arg Asp Gln Ser Arg Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
                515                 520                 525
Asp Asp Glu Asp Lys Phe Phe Pro Met Ser Gly Val Met Ile Phe Gly
                530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
                580                 585                 590
Thr Gly Asp Val His Ala Met Gly Ala Leu Pro Gly Met Val Trp Gln
                595                 600                 605
Asp Arg Asp Val Tyr Leu Gln Gly Pro Ile Trp Ala Lys Ile Pro His
                610                 615                 620
Thr Asp Gly His Phe His Pro Ser Pro Leu Met Gly Gly Phe Gly Leu
625                 630                 635                 640
Lys Asn Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Val Gln Tyr Thr Ser Asn
                690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735
```

<210> SEQ ID NO 37

-continued

<211> LENGTH: 736
<212> TYPE: PRT
<213> ORGANISM: Artificial sequence
<220> FEATURE:
<223> OTHER INFORMATION: Recombinant sequence

<400> SEQUENCE: 37

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Thr Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380
```

```
Ser Gln Ala Val Gly Arg Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 38
<211> LENGTH: 734
<212> TYPE: PRT
<213> ORGANISM: Artificial sequence
<220> FEATURE:
<223> OTHER INFORMATION: Recombinant sequence

<400> SEQUENCE: 38

Met Ala Ala Asp Gly Tyr Leu Pro Asp Trp Leu Glu Asp Asn Leu Ser
1               5                   10                  15
```

```
Glu Gly Ile Arg Glu Trp Trp Ala Leu Lys Pro Gly Val Pro Gln Pro
         20                  25                  30

Lys Ala Asn Gln Gln His Gln Asp Asn Arg Arg Gly Leu Val Leu Pro
         35                  40                  45

Gly Tyr Lys Tyr Leu Gly Pro Gly Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
             100                 105                 110

Asn Leu Gly Arg Ala Val Phe Gln Ala Lys Lys Arg Leu Leu Glu Pro
         115                 120                 125

Leu Gly Leu Val Glu Glu Ala Ala Lys Thr Ala Pro Gly Lys Lys Arg
 130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Ser Phe Lys Leu Phe Asn Ile Gln Val
305                 310                 315                 320

Lys Glu Val Thr Asp Asn Asn Gly Val Lys Thr Ile Ala Asn Asn Leu
                325                 330                 335

Thr Ser Thr Val Gln Val Phe Thr Asp Ser Asp Tyr Gln Leu Pro Tyr
            340                 345                 350

Val Leu Gly Ser Ala His Glu Gly Cys Leu Pro Pro Phe Pro Ala Asp
        355                 360                 365

Val Phe Met Ile Pro Gln Tyr Gly Tyr Leu Thr Leu Asn Asp Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Glu Phe Glu
                405                 410                 415

Asn Val Pro Phe His Ser Ser Tyr Ala His Ser Gln Ser Leu Asp Arg
            420                 425                 430
```

```
Leu Met Asn Pro Leu Ile Asp Gln Tyr Leu Tyr Tyr Leu Ser Lys Thr
        435                 440                 445

Ile Asn Gly Ser Gly Gln Asn Gln Gln Thr Leu Lys Phe Ser Val Ala
450                 455                 460

Gly Pro Ser Asn Met Ala Val Gln Gly Arg Asn Tyr Ile Pro Gly Pro
465                 470                 475                 480

Ser Tyr Arg Gln Gln Arg Val Ser Thr Val Thr Gln Asn Asn Asn
        485                 490                 495

Ser Glu Phe Ala Trp Pro Gly Ala Ser Ser Trp Ala Leu Asn Gly Arg
            500                 505                 510

Asn Ser Leu Met Asn Pro Gly Pro Ala Met Ala Ser His Lys Glu Gly
        515                 520                 525

Glu Asp Arg Phe Phe Pro Leu Ser Gly Ser Leu Ile Phe Gly Lys Gln
        530                 535                 540

Gly Thr Gly Arg Asp Asn Val Asp Ala Asp Lys Val Met Ile Thr Asn
545                 550                 555                 560

Glu Glu Glu Ile Lys Thr Thr Asn Pro Val Ala Thr Glu Ser Tyr Gly
                565                 570                 575

Gln Val Ala Thr Asn His Gln Ser Ala Gln Ala Gln Ala Gln Thr Gly
        580                 585                 590

Trp Val Gln Asn Gln Gly Ile Leu Pro Gly Met Val Trp Gln Asp Arg
595                 600                 605

Asp Val Tyr Leu Gln Gly Pro Ile Trp Ala Lys Ile Pro His Thr Asp
        610                 615                 620

Gly Asn Phe His Pro Ser Pro Leu Met Gly Gly Phe Gly Leu Lys His
625                 630                 635                 640

Pro Pro Pro Gln Ile Leu Ile Lys Asn Thr Pro Val Pro Ala Asp Pro
                645                 650                 655

Pro Thr Thr Phe Asn Gln Ser Lys Leu Asn Ser Phe Ile Thr Gln Tyr
            660                 665                 670

Ser Thr Gly Gln Val Ser Val Glu Ile Glu Trp Glu Leu Gln Lys Glu
        675                 680                 685

Asn Ser Lys Arg Trp Asn Pro Glu Val Gln Tyr Thr Ser Asn Tyr Ala
690                 695                 700

Lys Ser Ala Asn Val Asp Phe Thr Val Asp Asn Asn Gly Leu Tyr Thr
705                 710                 715                 720

Glu Pro Arg Pro Ile Gly Thr Arg Tyr Leu Thr Arg Pro Leu
                725                 730

<210> SEQ ID NO 39
<211> LENGTH: 736
<212> TYPE: PRT
<213> ORGANISM: Artificial sequence
<220> FEATURE:
<223> OTHER INFORMATION: Recombinant sequence

<400> SEQUENCE: 39

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60
```

```
Val Asn Ala Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Trp Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Asn Arg
435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
```

```
            485                 490                 495
Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
                580                 585                 590

Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 40
<211> LENGTH: 737
<212> TYPE: PRT
<213> ORGANISM: Artificial sequence
<220> FEATURE:
<223> OTHER INFORMATION: Recombinant sequence

<400> SEQUENCE: 40

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65              70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
```

```
            115                 120                 125
Leu Gly Leu Val Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
            195                 200                 205

Ala Pro Met Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ala Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Val Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Arg Thr Gln Thr Thr Gly Gly Thr Ala Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
            515                 520                 525

Lys Asp Asp Glu Glu Arg Phe Phe Pro Ser Asn Gly Ile Leu Ile Phe
    530                 535                 540
```

Gly Lys Gln Asn Ala Ala Arg Asp Asn Ala Asp Tyr Ser Asp Val Met
545                 550                 555                 560

Leu Thr Ser Glu Glu Ile Lys Thr Thr Asn Pro Val Ala Thr Glu
            565                 570                 575

Glu Tyr Gly Ile Val Ala Asp Asn Leu Gln Gln Asn Thr Ala Pro
            580                 585                 590

Gln Ile Gly Thr Val Asn Ser Gln Gly Asp Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Tyr Tyr Lys Ser Asn Asn Val Glu Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 41
<211> LENGTH: 734
<212> TYPE: PRT
<213> ORGANISM: Artificial sequence
<220> FEATURE:
<223> OTHER INFORMATION: Recombinant sequence

<400> SEQUENCE: 41

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Cys Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Thr Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

```
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
        290                 295                 300
Gly Phe Arg Pro Lys Arg Leu Ser Phe Lys Leu Phe Asn Ile Gln Val
305                 310                 315                 320
Lys Glu Val Thr Asp Asn Asn Gly Val Lys Thr Ile Ala Asn Asn Leu
                325                 330                 335
Thr Ser Thr Val Gln Val Phe Thr Asp Ser Asp Tyr Gln Leu Pro Tyr
                340                 345                 350
Val Leu Gly Ser Ala His Glu Gly Cys Leu Pro Pro Phe Pro Ala Asp
            355                 360                 365
Val Phe Met Ile Pro Gln Tyr Gly Tyr Leu Thr Leu Asn Asp Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Glu Phe Glu
                405                 410                 415
Asn Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Lys Thr
            435                 440                 445
Ile Asn Gly Ser Gly Gln Asn Gln Gln Thr Leu Lys Phe Ser Val Ala
        450                 455                 460
Gly Pro Ser Asn Met Ala Val Gln Gly Arg Asn Tyr Ile Pro Gly Pro
465                 470                 475                 480
Ser Tyr Arg Gln Gln Arg Val Ser Thr Thr Val Thr Gln Asn Asn Asn
                485                 490                 495
Ser Glu Phe Ala Trp Pro Gly Ala Ser Ser Trp Ala Leu Asn Gly Arg
            500                 505                 510
Asn Ser Leu Met Asn Pro Gly Pro Ala Met Ala Ser His Lys Glu Gly
        515                 520                 525
Glu Asp Arg Phe Phe Pro Leu Ser Gly Ser Leu Ile Phe Gly Lys Gln
    530                 535                 540
Gly Thr Gly Arg Asp Asn Val Asp Ala Asp Lys Val Met Ile Thr Asn
545                 550                 555                 560
Glu Glu Glu Ile Lys Thr Thr Asn Pro Val Ala Thr Glu Ser Tyr Gly
                565                 570                 575
Gln Val Ala Thr Asn His Gln Ser Ala Gln Ala Gln Ala Gln Thr Gly
```

```
                580                 585                 590
Trp Val Gln Asn Gln Gly Ile Leu Pro Gly Met Val Trp Gln Asp Arg
            595                 600                 605

Asp Val Tyr Leu Gln Gly Pro Ile Trp Ala Lys Ile Pro His Thr Asp
        610                 615                 620

Gly Asn Phe His Pro Ser Pro Leu Met Gly Gly Phe Gly Leu Lys His
625                 630                 635                 640

Pro Pro Pro Gln Ile Leu Ile Lys Asn Thr Pro Val Pro Ala Asn Pro
                645                 650                 655

Pro Ala Glu Phe Ser Ala Thr Lys Phe Ala Ser Phe Ile Thr Gln Tyr
            660                 665                 670

Ser Thr Gly Gln Val Ser Val Glu Ile Glu Trp Glu Leu Gln Lys Glu
        675                 680                 685

Asn Ser Lys Arg Trp Asn Pro Glu Val Gln Tyr Thr Ser Asn Tyr Ala
    690                 695                 700

Lys Ser Ala Asn Val Asp Phe Thr Val Asp Asn Asn Gly Leu Tyr Thr
705                 710                 715                 720

Glu Pro Arg Pro Ile Gly Thr Arg Tyr Leu Thr Lys Pro Leu
                725                 730

<210> SEQ ID NO 42
<211> LENGTH: 736
<212> TYPE: PRT
<213> ORGANISM: Artificial sequence
<220> FEATURE:
<223> OTHER INFORMATION: Recombinant sequence

<400> SEQUENCE: 42

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Thr Pro Ala Ala Val Gly Pro Thr Thr Met Ala Ser Gly Gly
        195                 200                 205

Gly Ala Pro Met Ala Asp Asn Asn Glu Gly Ala Asp Gly Val Gly Asn
```

```
             210                 215                 220
Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
                290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
                370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
                435                 440                 445

Thr Asn Thr Pro Ser Gly Thr Thr Thr Gln Ser Arg Leu Gln Phe Ser
                450                 455                 460

Gln Ala Gly Ala Ser Asp Ile Arg Asp Gln Ser Arg Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
                515                 520                 525

Asp Asp Glu Asp Lys Phe Phe Pro Met Ser Gly Val Met Ile Phe Gly
                530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
                580                 585                 590

Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640
```

```
Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 43
<211> LENGTH: 737
<212> TYPE: PRT
<213> ORGANISM: Artificial sequence
<220> FEATURE:
<223> OTHER INFORMATION: Recombinant sequence

<400> SEQUENCE: 43

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ala Thr Asn Asp Asn
            260                 265                 270
```

```
Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
                340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Arg Thr Gln Thr Thr Gly Gly Thr Ala Asn Thr Gln Thr Leu Gly Phe
            450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
                500                 505                 510

Asn Gly Arg Asn Ser Leu Ala Asn Pro Gly Ile Ala Met Ala Thr His
            515                 520                 525

Lys Asp Asp Glu Glu Arg Phe Phe Pro Ser Asn Gly Ile Leu Ile Phe
530                 535                 540

Gly Lys Gln Asn Ala Ala Arg Asp Asn Ala Asp Tyr Ser Asp Val Met
545                 550                 555                 560

Leu Thr Ser Glu Glu Glu Ile Lys Thr Thr Asn Pro Val Ala Thr Glu
                565                 570                 575

Glu Tyr Gly Ile Val Ala Asp Asn Leu Gln Gln Asn Thr Ala Pro
                580                 585                 590

Gln Ile Gly Thr Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
                660                 665                 670

Thr Gln Tyr Ser Thr Gly Gln Val Ser Val Glu Ile Glu Trp Glu Leu
            675                 680                 685
```

```
Gln Lys Glu Asn Ser Lys Arg Trp Asn Pro Glu Ile Gln Tyr Thr Ser
    690                 695                 700

Asn Tyr Tyr Lys Ser Asn Asn Val Glu Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 44
<211> LENGTH: 734
<212> TYPE: PRT
<213> ORGANISM: Artificial sequence
<220> FEATURE:
<223> OTHER INFORMATION: Recombinant sequence

<400> SEQUENCE: 44

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Ser Phe Lys Leu Phe Asn Ile Gln Val
```

```
305                 310                 315                 320
Lys Glu Val Thr Asp Asn Asn Gly Val Lys Thr Ile Ala Asn Asn Leu
                325                 330                 335

Thr Ser Thr Val Gln Val Phe Thr Asp Ser Asp Tyr Gln Leu Pro Tyr
                340                 345                 350

Val Leu Gly Ser Ala His Glu Gly Cys Leu Pro Phe Pro Ala Asp
                355                 360                 365

Val Phe Met Ile Pro Gln Tyr Gly Tyr Leu Thr Leu Asn Asp Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Glu Phe Glu
                405                 410                 415

Asn Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Lys Thr
                435                 440                 445

Ile Asn Gly Ser Gly Gln Asn Gln Gln Thr Leu Lys Phe Ser Val Ala
                450                 455                 460

Gly Pro Ser Asn Met Ala Val Gln Gly Arg Asn Tyr Ile Pro Gly Pro
465                 470                 475                 480

Ser Tyr Arg Gln Gln Arg Val Ser Thr Thr Val Thr Gln Asn Asn Asn
                485                 490                 495

Ser Glu Phe Ala Trp Pro Gly Ala Ser Ser Trp Ala Leu Asn Gly Arg
                500                 505                 510

Asn Ser Leu Met Asn Pro Gly Pro Ala Met Ala Ser His Lys Glu Gly
                515                 520                 525

Glu Asp Arg Phe Phe Pro Leu Ser Gly Ser Leu Ile Phe Gly Lys Gln
                530                 535                 540

Gly Thr Gly Arg Asp Asn Val Asp Ala Asp Lys Val Met Ile Thr Asn
545                 550                 555                 560

Glu Glu Glu Ile Lys Thr Thr Asn Pro Val Ala Thr Glu Ser Tyr Gly
                565                 570                 575

Gln Val Ala Thr Asn His Gln Ser Ala Gln Ala Gln Ala Gln Thr Gly
                580                 585                 590

Trp Val Gln Asn Gln Gly Ile Leu Pro Gly Met Val Trp Gln Asp Arg
                595                 600                 605

Asp Val Tyr Leu Gln Gly Pro Ile Trp Ala Lys Ile Pro His Thr Asp
                610                 615                 620

Gly Asn Phe His Pro Ser Pro Leu Met Gly Gly Phe Gly Met Lys His
625                 630                 635                 640

Pro Pro Pro Gln Ile Leu Ile Lys Asn Thr Pro Val Pro Ala Asp Pro
                645                 650                 655

Pro Thr Ala Phe Asn Lys Asp Lys Leu Asn Ser Phe Ile Thr Gln Tyr
                660                 665                 670

Ser Thr Gly Gln Val Ser Val Glu Ile Glu Trp Glu Leu Gln Lys Glu
                675                 680                 685

Asn Ser Lys Arg Trp Asn Pro Glu Ile Gln Tyr Thr Ser Asn Tyr Tyr
                690                 695                 700

Lys Ser Thr Ser Val Asp Phe Ala Val Asn Thr Glu Gly Val Tyr Ser
705                 710                 715                 720

Glu Pro Arg Pro Ile Gly Thr Arg Tyr Leu Thr Arg Asn Leu
                725                 730
```

<210> SEQ ID NO 45
<211> LENGTH: 738
<212> TYPE: PRT
<213> ORGANISM: Artificial sequence
<220> FEATURE:
<223> OTHER INFORMATION: Recombinant sequence

<400> SEQUENCE: 45

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365
```

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 46
<211> LENGTH: 736
<212> TYPE: PRT
<213> ORGANISM: Artificial sequence
<220> FEATURE:
<223> OTHER INFORMATION: Recombinant sequence

<400> SEQUENCE: 46

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
```

```
            405                 410                 415
Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735

<210> SEQ ID NO 47
<211> LENGTH: 736
<212> TYPE: PRT
<213> ORGANISM: Artificial sequence
<220> FEATURE:
<223> OTHER INFORMATION: Recombinant sequence

<400> SEQUENCE: 47

Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
```

-continued

```
                35                  40                  45
Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
450                 455                 460
```

Gln Ala Gly Pro Gln Ser Met Ser Leu Gln Ala Arg Asn Trp Leu Pro
465                 470                 475                 480

Gly Pro Cys Tyr Arg Gln Arg Leu Ser Lys Thr Ala Asn Asp Asn
            485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735

<210> SEQ ID NO 48
<211> LENGTH: 736
<212> TYPE: PRT
<213> ORGANISM: Artificial sequence
<220> FEATURE:
<223> OTHER INFORMATION: Recombinant sequence

<400> SEQUENCE: 48

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

-continued

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Gly Ala Lys Thr Ala Pro Gly Lys Lys Arg
    130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510
```

```
Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 49
<211> LENGTH: 737
<212> TYPE: PRT
<213> ORGANISM: Artificial sequence
<220> FEATURE:
<223> OTHER INFORMATION: Recombinant sequence

<400> SEQUENCE: 49

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140
```

```
Pro Val Glu Gln Ser Pro Gln Glu Pro Asp Ser Ser Gly Ile Gly
145                 150                 155                 160

Lys Thr Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Thr Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Phe Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Gln Ser Gly Val Leu Ile Phe
    530                 535                 540

Gly Lys Gln Gly Ser Glu Lys Thr Asn Val Asp Ile Glu Lys Val Met
545                 550                 555                 560

Ile Thr Asp Glu Glu Glu Ile Arg Thr Thr Asn Pro Val Ala Thr Glu
```

```
                    565                 570                 575

Gln Tyr Gly Ser Val Ser Thr Asn Leu Gln Arg Gly Asn Arg Gln Ala
                580                 585                 590

Ala Thr Ala Asp Val Asn Thr Gln Gly Val Leu Pro Gly Met Val Trp
            595                 600                 605

Gln Asp Arg Asp Val Tyr Leu Gln Gly Pro Ile Trp Ala Lys Ile Pro
        610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 50
<211> LENGTH: 737
<212> TYPE: PRT
<213> ORGANISM: Artificial sequence
<220> FEATURE:
<223> OTHER INFORMATION: Recombinant sequence

<400> SEQUENCE: 50

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Pro Asp Ser Ser Ser Gly Ile Gly
145                 150                 155                 160

Lys Thr Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190
```

-continued

```
Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Thr Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Phe Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Gln Ser Gly Val Leu Ile Phe
    530                 535                 540

Gly Lys Gln Gly Ser Glu Lys Thr Asn Val Asp Ile Glu Lys Val Met
545                 550                 555                 560

Ile Thr Asp Glu Glu Glu Ile Arg Thr Thr Asn Pro Val Ala Thr Glu
                565                 570                 575

Gln Tyr Gly Ser Val Ser Thr Asn Leu Gln Arg Gly Asn Arg Gln Ala
            580                 585                 590

Ala Thr Ala Asp Val Asn Thr Gln Gly Val Leu Pro Gly Met Val Trp
        595                 600                 605
```

-continued

```
Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
                660                 665                 670

Thr Gln Tyr Ser Thr Gly Gln Ser Val Glu Ile Glu Trp Glu Leu
                675                 680                 685

Gln Lys Glu Asn Ser Lys Arg Trp Asn Pro Gly Ile Gln Tyr Thr Ser
690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 51
<211> LENGTH: 735
<212> TYPE: PRT
<213> ORGANISM: Artificial sequence
<220> FEATURE:
<223> OTHER INFORMATION: Recombinant sequence

<400> SEQUENCE: 51

```
Met Ala Ala Asp Gly Tyr Leu Pro Asp Trp Leu Glu Asp Asn Leu Ser
1                   5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
```

```
            225                 230                 235                 240
        Thr Thr Ser Thr Arg Thr Trp Ala Leu Pro Thr Tyr Asn Asn His Leu
                        245                 250                 255
        Tyr Lys Gln Ile Ser Ser Gln Ser Gly Ala Ser Asn Asp Asn His Tyr
                        260                 265                 270
        Phe Gly Tyr Ser Thr Pro Trp Gly Tyr Phe Asp Phe Asn Arg Phe His
                        275                 280                 285
        Cys His Phe Ser Pro Arg Asp Trp Gln Arg Leu Ile Asn Asn Asn Trp
                        290                 295                 300
        Gly Phe Arg Pro Lys Arg Leu Ser Phe Lys Leu Phe Asn Ile Gln Val
        305                 310                 315                 320
        Lys Glu Val Thr Gln Asn Gly Thr Lys Thr Ile Ala Asn Asn Leu
                        325                 330                 335
        Thr Ser Thr Val Gln Val Phe Thr Asp Ser Glu Tyr Gln Leu Pro Tyr
                        340                 345                 350
        Val Leu Gly Ser Ala His Gln Gly Cys Leu Pro Pro Phe Pro Ala Asp
                        355                 360                 365
        Val Phe Met Val Pro Gln Tyr Gly Tyr Leu Thr Leu Asn Asn Gly Ser
                        370                 375                 380
        Gln Ala Val Gly Arg Ser Ser Phe Tyr Cys Leu Glu Tyr Phe Pro Ser
        385                 390                 395                 400
        Gln Met Leu Arg Thr Gly Asn Asn Phe Thr Phe Ser Tyr Thr Phe Glu
                        405                 410                 415
        Asp Val Pro Phe His Ser Ser Tyr Ala His Ser Gln Ser Leu Asp Arg
                        420                 425                 430
        Leu Met Asn Pro Leu Ile Asp Gln Tyr Leu Tyr Tyr Leu Ser Arg Thr
                        435                 440                 445
        Asn Thr Pro Ser Gly Thr Thr Thr Gln Ser Arg Leu Gln Phe Ser Gln
                        450                 455                 460
        Ala Gly Ala Ser Asp Ile Arg Asp Gln Ser Arg Asn Trp Leu Pro Gly
        465                 470                 475                 480
        Pro Cys Tyr Arg Gln Gln Arg Val Ser Lys Thr Ser Ala Asp Asn Asn
                        485                 490                 495
        Asn Ser Glu Tyr Ser Trp Thr Gly Ala Thr Lys Tyr His Leu Asn Gly
                        500                 505                 510
        Arg Asp Ser Leu Val Asn Pro Gly Pro Ala Met Ala Ser His Lys Asp
                        515                 520                 525
        Tyr Glu Glu Lys Phe Phe Pro Gln Ser Gly Val Leu Ile Phe Gly Lys
                        530                 535                 540
        Gln Gly Ser Glu Lys Thr Asn Val Asp Ile Glu Lys Val Met Ile Thr
        545                 550                 555                 560
        Asp Glu Glu Glu Ile Arg Thr Thr Asn Pro Val Ala Thr Glu Gln Tyr
                        565                 570                 575
        Gly Ser Val Ser Thr Asn Leu Gln Arg Gly Asn Arg Gln Ala Ala Thr
                        580                 585                 590
        Ala Asp Val Asn Thr Gln Gly Val Leu Pro Gly Met Val Trp Gln Asp
                        595                 600                 605
        Arg Asp Val Tyr Leu Gln Gly Pro Ile Trp Ala Lys Ile Pro His Thr
                        610                 615                 620
        Asp Gly His Phe His Pro Ser Pro Leu Met Gly Gly Phe Gly Leu Lys
        625                 630                 635                 640
        His Pro Pro Pro Gln Ile Leu Ile Lys Asn Thr Pro Val Pro Ala Asp
                        645                 650                 655
```

```
Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Tyr Lys Ser Thr Ser Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735

<210> SEQ ID NO 52
<211> LENGTH: 735
<212> TYPE: PRT
<213> ORGANISM: Artificial sequence
<220> FEATURE:
<223> OTHER INFORMATION: Recombinant sequence

<400> SEQUENCE: 52

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Ser Asn His Leu
                245                 250                 255

Tyr Lys Gln Ile Ser Ser Gln Ser Gly Ala Ser Asn Asp Asn Asp Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Glu Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700
```

```
Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 53
<211> LENGTH: 735
<212> TYPE: PRT
<213> ORGANISM: Artificial sequence
<220> FEATURE:
<223> OTHER INFORMATION: Recombinant sequence

<400> SEQUENCE: 53

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Asn Phe Lys Leu Phe Asn Ile Gln Val
305                 310                 315                 320

Lys Glu Val Thr Gln Asn Glu Gly Thr Lys Thr Ile Ala Asn Asn Leu
                325                 330                 335
```

Thr Ser Thr Ile Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
355                 360                 365

Val Phe Met Ile Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Thr Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Gln Thr Thr Gly Gly Thr Thr Asn Thr Gln Thr Leu Gly Phe Ser Gln
    450                 455                 460

Gly Gly Pro Asn Thr Met Ala Asn Gln Ala Lys Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

Asn Pro Pro Pro Gln Ile Leu Ile Lys Asn Thr Pro Val Pro Ala Asn
                645                 650                 655

Pro Pro Ala Glu Phe Ser Ala Thr Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Ala Lys Ser Ala Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 54
<211> LENGTH: 738
<212> TYPE: PRT

-continued

<213> ORGANISM: Artificial sequence
<220> FEATURE:
<223> OTHER INFORMATION: Recombinant sequence

<400> SEQUENCE: 54

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Thr Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Thr Ser Leu Gly Ser Asn Thr Met Ala Ser Gly Gly
        195                 200                 205

Gly Ala Pro Met Ala Asp Asn Asn Glu Gly Ala Asp Gly Val Gly Asn
    210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
```

385                 390                 395                 400

Pro Ser Gln Met Leu Arg Thr Gly Asn Asn Phe Gln Phe Ser Tyr Thr
                    405                 410                 415

Phe Glu Asp Val Pro Phe His Ser Ser Tyr Ala His Ser Gln Ser Leu
                    420                 425                 430

Asp Arg Leu Met Asn Pro Leu Ile Asp Gln Tyr Leu Tyr Leu Asn
                    435                 440                 445

Arg Thr Gln Gly Thr Thr Ser Gly Thr Thr Asn Gln Ser Arg Leu Leu
                    450                 455                 460

Phe Ser Gln Ala Gly Pro Gln Ser Met Ser Leu Gln Ala Arg Asn Trp
465                 470                 475                 480

Leu Pro Gly Pro Cys Tyr Arg Gln Gln Arg Leu Ser Lys Thr Ala Asn
                    485                 490                 495

Asp Asn Asn Asn Ser Asn Phe Pro Trp Thr Ala Ala Ser Lys Tyr His
                    500                 505                 510

Leu Asn Gly Arg Asp Ser Leu Val Asn Pro Gly Pro Ala Met Ala Ser
                    515                 520                 525

His Lys Asp Asp Glu Glu Lys Phe Phe Pro Met His Gly Asn Leu Ile
                    530                 535                 540

Phe Gly Lys Glu Gly Thr Thr Ala Ser Asn Ala Glu Leu Asp Asn Val
545                 550                 555                 560

Met Ile Thr Asp Glu Glu Glu Ile Arg Thr Thr Asn Pro Val Ala Thr
                    565                 570                 575

Glu Gln Tyr Gly Thr Val Ala Asn Asn Leu Gln Ser Ser Asn Thr Ala
                    580                 585                 590

Pro Thr Thr Arg Thr Val Asn Asp Gln Gly Ala Leu Pro Gly Met Val
                    595                 600                 605

Trp Gln Asp Arg Asp Val Tyr Leu Gln Gly Pro Ile Trp Ala Lys Ile
                    610                 615                 620

Pro His Thr Asp Gly His Phe His Pro Ser Pro Leu Met Gly Gly Phe
625                 630                 635                 640

Gly Leu Lys His Pro Pro Pro Gln Ile Leu Ile Lys Asn Thr Pro Val
                    645                 650                 655

Pro Ala Asn Pro Ser Thr Thr Phe Ser Ala Ala Lys Phe Ala Ser Phe
                    660                 665                 670

Ile Thr Gln Tyr Ser Thr Gly Gln Val Ser Val Glu Ile Glu Trp Glu
                    675                 680                 685

Leu Gln Lys Glu Asn Ser Lys Arg Trp Asn Pro Glu Ile Gln Tyr Thr
                    690                 695                 700

Ser Asn Tyr Tyr Lys Ser Asn Asn Val Glu Phe Ala Val Asn Thr Glu
705                 710                 715                 720

Gly Val Tyr Ser Glu Pro Arg Pro Ile Gly Thr Arg Tyr Leu Thr Arg
                    725                 730                 735

Asn Leu

<210> SEQ ID NO 55
<211> LENGTH: 735
<212> TYPE: PRT
<213> ORGANISM: Artificial sequence
<220> FEATURE:
<223> OTHER INFORMATION: Recombinant sequence

<400> SEQUENCE: 55

Met Ala Ala Asp Gly Tyr Leu Pro Asp Trp Leu Glu Asp Thr Leu Ser
1               5                   10                  15

```
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
```

```
Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 56
<211> LENGTH: 738
<212> TYPE: PRT
<213> ORGANISM: Artificial sequence
<220> FEATURE:
<223> OTHER INFORMATION: Recombinant sequence

<400> SEQUENCE: 56

Met Ala Ala Asp Gly Tyr Leu Pro Asp Trp Leu Glu Asp Thr Leu Ser
1               5                   10                  15

Glu Gly Ile Arg Gln Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
             85                      90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Thr Ser Leu Gly Ser Asn Thr Met Ala Ser Gly Gly
            195                 200                 205

Gly Ala Pro Met Ala Asp Asn Asn Glu Gly Ala Asp Gly Val Gly Asn
        210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Gly Thr Thr Ser Gly Thr Thr Asn Gln Ser Arg Leu Leu
        450                 455                 460

Phe Ser Gln Ala Gly Pro Gln Ser Met Ser Leu Gln Ala Arg Asn Trp
465                 470                 475                 480
```

-continued

```
Leu Pro Gly Pro Cys Tyr Arg Gln Gln Arg Leu Ser Lys Thr Ala Asn
            485                 490                 495

Asp Asn Asn Asn Ser Asn Phe Pro Trp Thr Ala Ala Ser Lys Tyr His
        500                 505                 510

Leu Asn Gly Arg Asp Ser Leu Val Asn Pro Gly Pro Ala Met Ala Ser
        515                 520                 525

His Lys Asp Asp Glu Glu Lys Phe Phe Pro Met His Gly Asn Leu Ile
        530                 535                 540

Phe Gly Lys Glu Gly Thr Ala Ser Asn Ala Glu Leu Asp Asn Val
545                 550                 555                 560

Met Ile Thr Asp Glu Glu Glu Ile Arg Thr Thr Asn Pro Val Ala Thr
            565                 570                 575

Glu Gln Tyr Gly Thr Val Ala Asn Asn Leu Gln Ser Ser Asn Thr Ala
            580                 585                 590

Pro Thr Thr Arg Thr Val Asn Asp Gln Gly Ala Leu Pro Gly Met Val
            595                 600                 605

Trp Gln Asp Arg Asp Val Tyr Leu Gln Gly Pro Ile Trp Ala Lys Ile
            610                 615                 620

Pro His Thr Asp Gly His Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asn Pro Ser Thr Thr Phe Ser Ala Ala Lys Phe Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Asn Asn Val Glu Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

AAV CAPSID PROTEINS FOR NUCLEIC ACID TRANSFER

CROSS REFERENCE TO RELATED APPLICATIONS

This application claims benefit under 35 U.S.C. §119(e) to application Ser. Nos. 61/526,688, filed 24 Aug. 2011; and 61/545,488, filed 10 Oct. 2011, the contents of each of which are incorporated herein by reference in their entirety.

STATEMENT REGARDING FEDERALLY SPONSORED RESEARCH

This invention was made with Government support under contract HL092096 awarded by the National Institutes of Health. The Government has certain rights in this invention.

REFERENCE TO SEQUENCE LISTING, TABLE OR COMPUTER PROGRAM

The present disclosure includes a sequence listing which is being submitted electronically in the form of a text file, created 24 August 2012 and named "586008273.WO00FINALseqlist.TXT" (266,240 bytes), the contents of which are incorporated herein by reference in their entirety.

INTRODUCTION

The subject matter described herein relates to in vitro and in vivo selection of sequences from a library of sequences encoding recombinant adeno-associated viral (AAV) viral capsid proteins and to methods of generating the libraries. The subject matter also relates to nucleotide sequences isolated from the libraries and to the AAV capsid proteins encoded by these sequences, and their usefulness as capsid proteins in recombinant AAV vectors for various nucleic acid transfer applications. The subject matter also relates to plasmids and viruses comprising the identified sequences, which preferably provide a high transduction efficiency and a low level of neutralization by the human immune system.

BACKGROUND

Multiple recombinant gene transfer vectors based on different types of viruses have been developed and tested in clinical trials in recent years. Gene transfer vectors based on adeno-associated virus (AAV), i.e., AAV vectors, have become favored vectors because of characteristics such as an ability to transduce different types of dividing and non-dividing cells of different tissues and the ability to establish stable, long-term transgene expression. While vectors based on other viruses, such as adenoviruses and retroviruses may posses certain desirable characteristics, the use of other vectors has been associated with toxicity or some human diseases. These side effects have not been detected with gene transfer vectors based on AAV (Manno et al., *Nature Medicine,* 12(3):342 (2006)). Additionally, the technology to produce and purify AAV vectors without undue effort has been developed.

At least eleven AAV serotypes have been identified, cloned, sequenced, and converted into vectors, and at least 100 new AAV variants have been isolated from non-primates, primates and humans. However, the majority of preclinical data to date involving AAV vectors has been generated with vectors based on the human AAV-2 serotype, considered the AAV prototype.

There are several disadvantages to the currently used AAV-2 vectors. For example, a number of clinically relevant cell types and tissues are not efficiently transduced with these vectors. Also, a large percentage of the human population is immune to AAV-2 due to prior exposure to wildtype AAV-2 virus. It has been estimated that up to 96% of humans are seropositive for AAV-2, and up to 67% of the seropositive individuals carry neutralizing anti-AAV-2 antibodies which could eliminate or greatly reduce transduction by AAV-2 vectors. Moreover, AAV-2 has been reported to cause a cell mediated immune response in patients when given systemically (Manno et al., *Nature Medicine,* 12(3):342 (2006)).

Methods of overcoming the limitations of AAV-2 vectors have been proposed. For example, randomly mutagenizing the nucleotide sequence encoding the AAV-2 capsid by error-prone PCR has been proposed as a method of generating AAV-2 mutants that are able to escape the neutralizing antibodies that affect wildtype AAV-2. However, it is expected that it will be difficult to generate significantly improved AAV-2 variants with single random point mutations, as the naturally occurring serotypes have, at most, only about 85% homology in the capsid nucleotide sequence.

Methods of using a mixture of AAV serotype constructs for AAV vectors have also been developed. The resulting chimeric vectors possess capsid proteins from different serotypes, and ideally, have properties of the different serotypes used. However, the ratio of the different capsid proteins is different from vector to vector and cannot be consistently controlled or reproduced (due to lack of genetic templates), which is unacceptable for clinical use and not satisfactory for experimental use.

A third approach at modifying the AAV-2 capsid are peptide insertion libraries, in which randomized oligonucleotides encoding up to 7 amino acids are incorporated into a defined location within the AAV-2 capsid. The display of these peptides on the AAV-2 capsid surface can then be exploited to re-target the particles to cells or tissues that are otherwise refractory to infection with the wildtype AAV-2 virus. However, because knowledge of the atomic capsid structure is a prerequisite for this type of AAV modification, this method is generally restricted to AAV serotype 2. Moreover, peptide insertion libraries typically cannot address the issues of AAV particle immunogenicity or transduction efficiency.

Thus, a need remains for new AAV vectors and a method of generating new AAV vectors. In particular, there is a need for AAV based vectors that can be used efficiently with a variety of cell types and tissues, and that do not react with a pre-existing anti-AAV human immunity that could neutralize or inactivate the vectors. Also needed are vectors that transduce different cell types in vivo and in vitro and that offer a more restricted biodistribution or a more promiscuous biodistribution, depending on the intended use. In particular, there remains a need for vectors capable of transducing a variety of cells types, such as hematopoietic stem cells or embryonic stem cells, as well as having desirable properties.

A recombinant AAV vector known as "AAV-DJ" has been reported and described in U.S. patent application Ser. No. 12/538,791, published as US 20100047174, which is incorporated by reference herein, in its entirety.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, recombinant capsid proteins and methods for generating recombinant capsid proteins are provided. The capsid proteins include regions or domains that are derived from different serotypes of AAV. The AAV serotypes may be human or non-human. Recombinant AAV comprising the capsid proteins and plasmids encoding the capsid proteins are also provided.

In one aspect, a capsid protein comprises a first amino acid sequence similar or identical to a contiguous sequence of amino acids from a first AAV serotype, and a second amino acid sequence similar or identical to a contiguous sequence of amino acids from at least a second AAV serotype.

In one embodiment, the capsid protein additionally comprises a sequence of amino acid residues similar or identical to a contiguous sequence of amino acids from a third AAV serotype.

In another embodiment, the sequences of amino acids in the first sequence, in the second sequence, and in the third or further sequence, are each a contiguous sequence of amino acids from the first AAV serotype, the second AAV serotype, the third and/or further AAV serotypes. In another embodiment, the contiguous sequence of amino acids forms a conserved set of amino acid residues, the conserved set having at least about 70% sequence identity, at least about 75% sequence identity, at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity with the AAV serotype from a contiguous sequence in its respective AAV serotype.

In some aspects, a capsid protein is encoded by a nucleotide sequence selected from the group of sequences consisting of SEQ ID NOs: 1-28, or a sequence having at least 95% sequence identity thereto.

In one embodiment, the capsid protein comprises an amino acid sequence encoded by the nucleotide sequence identified by SEQ ID NO: 1.

In one embodiment, the capsid protein comprises an amino acid sequence encoded by the nucleotide sequence identified by SEQ ID NO: 2.

In one embodiment, the capsid protein comprises an amino acid sequence encoded by the nucleotide sequence identified by SEQ ID NO: 3.

In one embodiment, the capsid protein comprises an amino acid sequence encoded by the nucleotide sequence identified by SEQ ID NO: 4.

In one embodiment, the capsid protein comprises an amino acid sequence encoded by the nucleotide sequence identified by SEQ ID NO: 5.

In one embodiment, the capsid protein comprises an amino acid sequence encoded by the nucleotide sequence identified by SEQ ID NO: 6.

In one embodiment, the capsid protein comprises an amino acid sequence encoded by the nucleotide sequence identified by SEQ ID NO: 7.

In one embodiment, the capsid protein comprises an amino acid sequence encoded by the nucleotide sequence identified by SEQ ID NO: 8.

In one embodiment, the capsid protein comprises an amino acid sequence encoded by the nucleotide sequence identified by SEQ ID NO: 9.

In one embodiment, the capsid protein comprises an amino acid sequence encoded by the nucleotide sequence identified by SEQ ID NO: 10.

In one embodiment, the capsid protein comprises an amino acid sequence encoded by the nucleotide sequence identified by SEQ ID NO: 11.

In one embodiment, the capsid protein comprises an amino acid sequence encoded by the nucleotide sequence identified by SEQ ID NO: 12.

In one embodiment, the capsid protein comprises an amino acid sequence encoded by the nucleotide sequence identified by SEQ ID NO: 13.

In one embodiment, the capsid protein comprises an amino acid sequence encoded by the nucleotide sequence identified by SEQ ID NO: 14.

In one embodiment, the capsid protein comprises an amino acid sequence encoded by the nucleotide sequence identified by SEQ ID NO: 15.

In one embodiment, the capsid protein comprises an amino acid sequence encoded by the nucleotide sequence identified by SEQ ID NO: 16.

In one embodiment, the capsid protein comprises an amino acid sequence encoded by the nucleotide sequence identified by SEQ ID NO: 17.

In one embodiment, the capsid protein comprises an amino acid sequence encoded by the nucleotide sequence identified by SEQ ID NO: 18.

In one embodiment, the capsid protein comprises an amino acid sequence encoded by the nucleotide sequence identified by SEQ ID NO: 19.

In one embodiment, the capsid protein comprises an amino acid sequence encoded by the nucleotide sequence identified by SEQ ID NO: 20.

In one embodiment, the capsid protein comprises an amino acid sequence encoded by the nucleotide sequence identified by SEQ ID NO: 21.

In one embodiment, the capsid protein comprises an amino acid sequence encoded by the nucleotide sequence identified by SEQ ID NO: 22.

In one embodiment, the capsid protein comprises an amino acid sequence encoded by the nucleotide sequence identified by SEQ ID NO: 23.

In one embodiment, the capsid protein comprises an amino acid sequence encoded by the nucleotide sequence identified by SEQ ID NO: 24.

In one embodiment, the capsid protein comprises an amino acid sequence encoded by the nucleotide sequence identified by SEQ ID NO: 25.

In one embodiment, the capsid protein comprises an amino acid sequence encoded by the nucleotide sequence identified by SEQ ID NO: 26.

In one embodiment, the capsid protein comprises an amino acid sequence encoded by the nucleotide sequence identified by SEQ ID NO: 27.

In one embodiment, the capsid protein comprises an amino acid sequence encoded by the nucleotide sequence identified by SEQ ID NO: 28.

A viral particle comprising a capsid protein sequence as described above, is contemplated in some embodiments. Disclosed herein is a genus of viral particles comprising the capsid proteins encoded by the nucleotide sequences identified by SEQ ID NOs: 1-28 of the sequence listing, or a sequence having at least 95% sequence identity to said sequences.

Also disclosed is a plasmid comprising the nucleotide sequence selected from the group of sequences consisting of SEQ ID NOs: 1-28, or a sequence having at least 95% sequence identity thereto.

Also disclosed is a recombinant AAV vector (rAAV), comprising a capsid protein having an amino acid sequence encoded by a nucleotide sequence selected from the group of sequences consisting of SEQ ID NOs: 1-28, or a sequence having at least 95% sequence identity thereto.

In one aspect, a method of expressing a gene of interest in a mammal is provided. The present disclosure also provides a method of transfer of a nucleic acid of interest into a mammal, comprising introducing a recombinant AAV vector into a mammal, the recombinant AAV vector encoding a gene of interest which is encapsidated into a capsid protein encoded by a nucleotide sequence selected from the group of sequences consisting of SEQ ID NOs: 1-28, or a sequence having at least 95% sequence identity thereto.

In still another aspect, a method of generating a library of recombinant AAV plasmids is disclosed, the method comprising: isolating AAV capsid nucleotide sequences from two or more serotypes of AAV; digesting the AAV capsid nucleotide sequences into fragments; reassembling the fragments using PCR to form PCR products; and cloning the re-assembled PCR products into plasmids to generate a library of recombinant AAV plasmids.

The present disclosure also provides a method of generating a library of recombinant AAV plasmids, comprising (a) isolating AAV capsid nucleotide sequences from two or more serotypes of AAV; (b) digesting the AAV capsid nucleotide sequences into fragments; (c) reassembling the fragments using PCR to form PCR products; and (d) cloning the re-assembled PCR products into a wildtype viral genome to generate a library of recombinant AAV vectors (rAAVs).

In another embodiment, the method comprises transfecting cells with the plasmids to produce a viral library, preferably an AAV viral library. In some aspects, the method further comprises (e) infecting cells in vitro with the rAAVs; (f) passaging the selected rAAVs in cells in vitro in the presence of a stringent condition and identifying an rAAV capsid that survives said passaging; and, optionally, (g) repeating (b) through (f) one or more times. In some aspects, the method further comprises (h) infecting a laboratory mammal in vivo with the selected rAAVs; (i) passaging the selected rAAVs in a laboratory mammal in vivo able to infect and propagate in said laboratory mammal and identifying an rAAV capsid that survives said passaging; and, optionally, (j) repeating (h) and (i) one or more times.

Adenovirus has a broad host range, i.e., it can infect many human and other mammalian cell lines or primary cells, including replicative as well as non-replicative cells. Some lymphoid cell lines may be more resistant to Adenovirus infection, and thus may need high quantities of viruses to achieve sufficient infection levels. Cell types that may be used in the methods disclosed herein include, but are not limited to, CHO cells, monocytes, dendritic cells (DCs), freshly isolated human blood myeloid DCs, plasmacytoid DCs and monocyte-derived DCs, Langerhans cells and dermal DCs, Human T cell leukemia DND-41 cells, p53-deficient cancer cells, tumor cells retaining wild-type p53, tumor cells of unknown p53 status, adenocarcinomic human alveolar basal epithelial cells, also known as "A549 cells," human KB cells, Madin Darby Bovine Kidney (MDBK) cells, Mouse Embryonic Fibroblasts (MEF cells), human pulmonary artery endothelial cells (hPAEC), NIH-3T3 cells, Huh-7.5 cells, Hep G2 cells, HEp-2 cells, HeLa cells, Dempsey cells, human embryonic kidney 293 cells (also known as "HEK 293" or "293 cells"), fetal rhesus monkey kidney (FRhK-4) cells, rat hepatoma H4TG cells, LMH chicken hepatoma epithelial cells, primary human hepatocytes and primary human keratinocytes. In some aspects, the rAAV is used to infect 293 cells. In some aspects, the rAAV is used to infect hPAEC cells. In some aspects, the rAAV is used to infect Huh-7.5 cells. In some embodiments a helper Adenovirus is used.

In some embodiments, humanized FRG mice are transfected with an AAV in vitro selected library. In some embodiments, non-humanized FRG mice are transfected with an AAV in vitro selected library.

In some embodiments, the method additionally includes, after the transfecting, passaging the viral library in a selected cell type in the presence of a stringent condition, and selecting AAV capsids that survive the passaging. Passaging can be for several or multiple passages, for example from between 2-5 or 2-10 passages.

In some embodiments, the method additionally includes, after transfecting an animal model, passaging the AAV library through additional animal models, for subsequent selection of particular AAV isolates.

In one embodiment, a stringent condition comprises the presence of human immune globulin.

In another aspect, a library prepared according to the methods described above is disclosed. In one embodiment the library is comprised of plasmids of shuffled full-length capsid genes and in another embodiment the library is comprised of viral particles obtained by transfecting all or a portion of the plasmid library into a selected cell, optionally in combination with an adenoviral helper plasmid. The new, selected AAV capsid proteins described herein are useful for ex vivo or in vivo gene transfer, gene therapy, and genome editing applications, for example.

A library prepared according to these methods is also provided.

In addition to the exemplary aspects and embodiments described above, further aspects and embodiments will become apparent by reference to the drawings and by study of the following descriptions.

BRIEF DESCRIPTION OF THE FIGURES

FIG. 1 is a schematic showing a process for generating a recombinant AAV library;

FIG. 2 is a flow chart summarizing a method of generating a library of AAV capsids using AAV shuffle library selection;

FIG. 3 shows rounds 1 and 2 of AAV shuffle library selection in vitro;

FIG. 4 shows rounds 2 and 3 of AAV shuffle library selection in vitro;

FIG. 5 shows rounds 3 and 4 of AAV shuffle library selection in vitro;

FIG. 6 compares the proportion of clones in the library to the proportion in each round of selection in vitro;

FIG. 7 compares portions of several AAV serotypes and a recombinant AAV capsid protein in the library (AAV-PAEC);

FIG. 8: compares amino acid substitutions in two rAAVs;

FIG. 9: shows various views of a predicted 3-D structure of AAV-PAEC;

FIG. 10: illustrates an experimental design of a process used to screen an AAV shuffle library in vivo;

FIG. 11: illustrates an actual experiment used to screen an AAV shuffle library in vivo;

FIG. 12: shows PCR amplified isolates from the AAV shuffle library screen in vivo;

FIG. 13: compares the proportions of individual clones in the library to the proportion of individual clones in the selection from rounds 1 and 4 of in vivo;

FIG. 14: shows amino acid substitutions in one selected rAAV (AAV-LK01);

FIG. 15: shows various views of a predicted structure of AAV-LK01;

FIG. 16: compares residues implicated in heparin binding in AAV-2 to residues in new rAAVs;

FIG. 17: compares several AAV serotypes to several rAAV capsid proteins isolated using in vivo selection;

FIG. 18: shows amino acid substitutions in one selected rAAV (AAV-LK02);

FIG. 19: shows various views of a predicted structure of AAV-LK02;

FIG. 20: shows amino acid substitutions in one selected rAAV (AAV-LK03);

FIGS. 21 and 22: compare the relationship of selected rAAVs to wildtype AAVs on the DNA level and amino acid level, respectively;

FIGS. 23A and 23B: show the Dot Blot titers of the rAAVs as compared to wildtype AAVs;

FIGS. 24A and 24B: compare the transduction titers of the rAAVs to wildtype AAVs in Huh7.5 cells;

FIGS. 25A, 25B and 25C: compare transduction efficiency per AAV vector genome (vg) of the rAAVs to wildtype AAVs in Huh7.5 cells;

FIG. 26: compares transduction efficiency of rAAVs to wildtype AAVs in 293 cells;

FIG. 27: compares transduction efficiency of rAAVs to wildtype AAVs in NIH3T3 cells;

FIG. 28: compares transduction efficiency of selected rAAV isolates to wildtype AAVs in MEF cells;

FIG. 46: compares the transduction of various cell lines by several wild type and recombinant AAV serotypes;

FIG. 47: shows relatedness of wildtype AAVs to rAAVs isolates obtained by selection on human PAEC cells on the DNA level and amino acid level; and FIG. 48: shows the titer and transduction efficiency of rAAVs isolates obtained by selection on human PAEC cells as compared to wildtype AAVs.

BRIEF DESCRIPTION OF THE SEQUENCES

Figure 29:
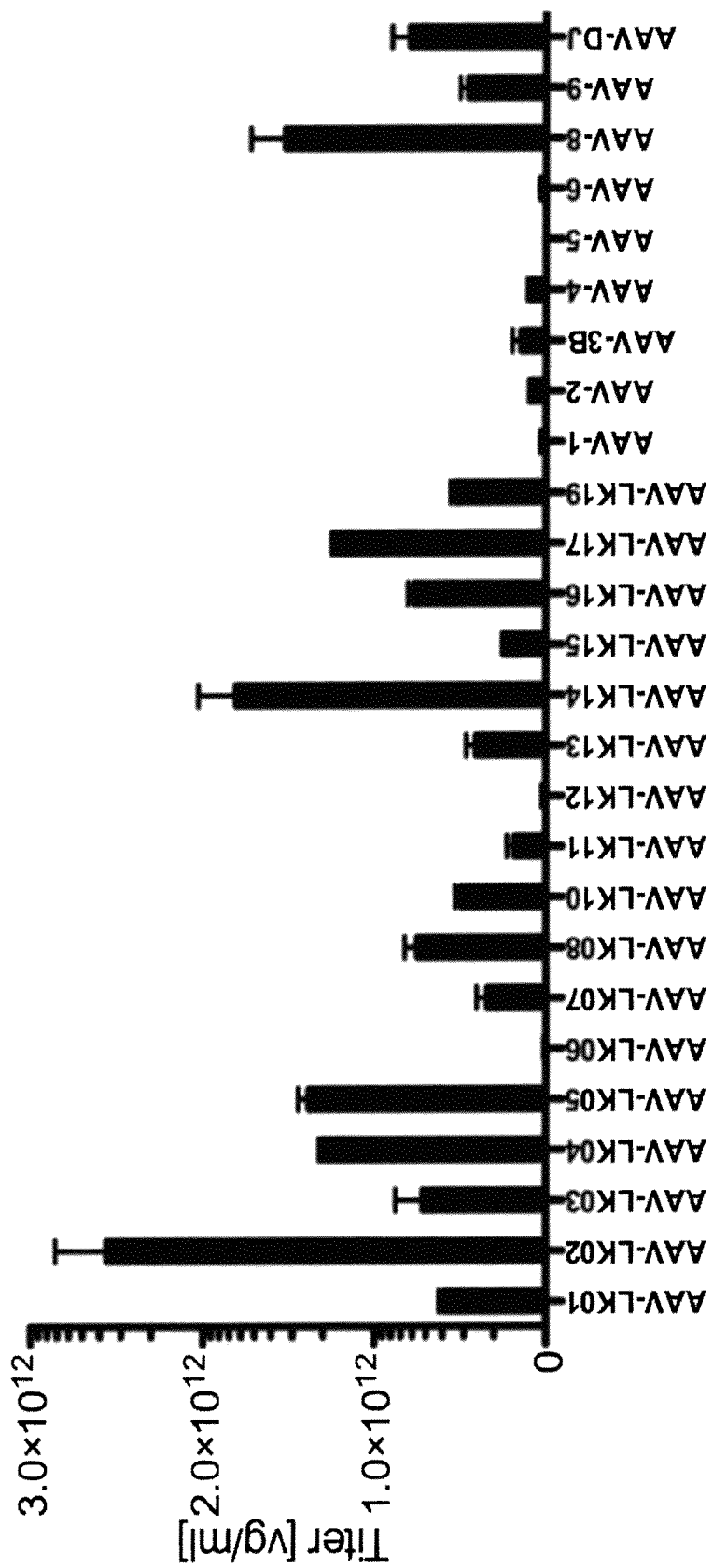
FIG. 29: shows the Dot Blot titers of certain rAAV isolates as compared to wildtype AAVs.

SEQ ID NO:1 is a nucleotide sequence encoding a novel recombinant AAV capsid protein, referred to herein as AAV-PAEC.

SEQ ID NO:2 is a nucleotide sequence encoding a novel recombinant AAV capsid protein, referred to herein as AAV-LK01.

SEQ ID NO:3 is a nucleotide sequence encoding a novel recombinant AAV capsid protein, referred to herein as AAV-LK02.

SEQ ID NO:4 is a nucleotide sequence encoding a novel recombinant AAV capsid protein, referred to herein as AAV-LK03.

SEQ ID NO:5 is a nucleotide sequence encoding a novel recombinant AAV capsid protein, referred to herein as AAV-LK04.

SEQ ID NO:6 is a nucleotide sequence encoding a novel recombinant AAV capsid protein, referred to herein as AAV-LK05.

SEQ ID NO:7 is a nucleotide sequence encoding a novel recombinant AAV capsid protein, referred to herein as AAV-LK06.

SEQ ID NO:8 is a nucleotide sequence encoding a novel recombinant AAV capsid protein, referred to herein as AAV-LK07.

SEQ ID NO:9 is a nucleotide sequence encoding a novel recombinant AAV capsid protein, referred to herein as AAV-LK08.

SEQ ID NO:10 is a nucleotide sequence encoding a novel recombinant AAV capsid protein, referred to herein as AAV-LK09.

SEQ ID NO:11 is a nucleotide sequence encoding a novel recombinant AAV capsid protein, referred to herein as AAV-LK10.

SEQ ID NO:12 is a nucleotide sequence encoding a novel recombinant AAV capsid protein, referred to herein as AAV-LK11.

SEQ ID NO:13 is a nucleotide sequence encoding a novel recombinant AAV capsid protein, referred to herein as AAV-LK12.

SEQ ID NO:14 is a nucleotide sequence encoding a novel recombinant AAV capsid protein, referred to herein as AAV-LK13.

SEQ ID NO:15 is a nucleotide sequence encoding a novel recombinant AAV capsid protein, referred to herein as AAV-LK14.

SEQ ID NO:16 is a nucleotide sequence encoding a novel recombinant AAV capsid protein, referred to herein as AAV-LK15.

SEQ ID NO:17 is a nucleotide sequence encoding a novel recombinant AAV capsid protein, referred to herein as AAV-LK16.

SEQ ID NO:18 is a nucleotide sequence encoding a novel recombinant AAV capsid protein, referred to herein as AAV-LK17.

SEQ ID NO:19 is a nucleotide sequence encoding a novel recombinant AAV capsid protein, referred to herein as AAV-LK18.

SEQ ID NO:20 is a nucleotide sequence encoding a novel recombinant AAV capsid protein, referred to herein as AAV-LK19.

SEQ ID NO:21 is a nucleotide sequence encoding a novel recombinant AAV capsid protein, referred to herein as AAV-PAEC2.

SEQ ID NO:22 is a nucleotide sequence encoding a novel recombinant AAV capsid protein, referred to herein as AAV-PAEC4.

SEQ ID NO:23 is a nucleotide sequence encoding a novel recombinant AAV capsid protein, referred to herein as AAV-PAEC6.

SEQ ID NO:24 is a nucleotide sequence encoding a novel recombinant AAV capsid protein, referred to herein as AAV-PAEC7.

SEQ ID NO:25 is a nucleotide sequence encoding a novel recombinant AAV capsid protein, referred to herein as AAV-PAEC8.

SEQ ID NO:26 is a nucleotide sequence encoding a novel recombinant AAV capsid protein, referred to herein as AAV-PAEC11.

SEQ ID NO:27 is a nucleotide sequence encoding a novel recombinant AAV capsid protein, referred to herein as AAV-PAEC12.

SEQ ID NO:28 is a nucleotide sequence encoding a novel recombinant AAV capsid protein, referred to herein as AAV-PAEC13.

SEQ ID NO:29 is an amino acid sequence encoded by SEQ ID NO: 2 (AAV-LK01).

SEQ ID NO:30 is an amino acid sequence encoded by SEQ ID NO: 3 (AAV-LK02).

SEQ ID NO:31 is an amino acid sequence encoded by SEQ ID NO: 4 (AAV-LK03).

SEQ ID NO:32 is an amino acid sequence encoded by SEQ ID NO: 5 (AAV-LK04).

SEQ ID NO:33 is an amino acid sequence encoded by SEQ ID NO: 6 (AAV-LK05).

SEQ ID NO:34 is an amino acid sequence encoded by SEQ ID NO: 7 (AAV-LK06).

SEQ ID NO:35 is an amino acid sequence encoded by SEQ ID NO: 8 (AAV-LK07).

SEQ ID NO:36 is an amino acid sequence encoded by SEQ ID NO: 9 (AAV-LK08).

SEQ ID NO:37 is an amino acid sequence encoded by SEQ ID NO: 10 (AAV-LK09).

SEQ ID NO:38 is an amino acid sequence encoded by SEQ ID NO: 11 (AAV-LK10).

SEQ ID NO:39 is an amino acid sequence encoded by SEQ ID NO: 12 (AAV-LK11).

SEQ ID NO:40 is an amino acid sequence encoded by SEQ ID NO: 13 (AAV-LK12).

SEQ ID NO:41 is an amino acid sequence encoded by SEQ ID NO: 14 (AAV-LK13).

SEQ ID NO:42 is an amino acid sequence encoded by SEQ ID NO: 15 (AAV-LK14).

SEQ ID NO:43 is an amino acid sequence encoded by SEQ ID NO: 16 (AAV-LK15).

SEQ ID NO:44 is an amino acid sequence encoded by SEQ ID NO: 17 (AAV-LK16).

SEQ ID NO:45 is an amino acid sequence encoded by SEQ ID NO: 18 (AAV-LK17).

SEQ ID NO:46 is an amino acid sequence encoded by SEQ ID NO: 19 (AAV-LK18).

SEQ ID NO:47 is an amino acid sequence encoded by SEQ ID NO: 20 (AAV-LK19).

SEQ ID NO:48 is an amino acid sequence encoded by SEQ ID NO: 1 (PAEC).

SEQ ID NO:49 is an amino acid sequence encoded by SEQ ID NO: 28 (PAEC-13).

SEQ ID NO:50 is an amino acid sequence encoded by SEQ ID NO: 25 (PAEC-8).

SEQ ID NO:51 is an amino acid sequence encoded by SEQ ID NO: 27 (PAEC-12).

SEQ ID NO:52 is an amino acid sequence encoded by SEQ ID NO: 23 (PAEC-6).

SEQ ID NO:53 is an amino acid sequence encoded by SEQ ID NO: 24 (PAEC-7).

SEQ ID NO:54 is an amino acid sequence encoded by SEQ ID NO: 26 (PAEC-11).

SEQ ID NO:55 is an amino acid sequence encoded by SEQ ID NO: 22 (PAEC-4).

SEQ ID NO:56 is an amino acid sequence encoded by SEQ ID NO: 21 (PAEC-2).

It is to be understood that each of the nucleotide sequences disclosed herein can be translated to predict an amino acid sequence representing a rAAV capsid protein.

DETAILED DESCRIPTION

Several embodiments of the present disclosure are described in detail hereinafter. These embodiments may take many different forms and should not be construed as limited to those embodiments explicitly set forth herein. Rather, these embodiments are provided so that this disclosure will be thorough and complete, and will fully convey the scope of the present disclosure to those skilled in the art.

I. Definitions

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

It must be noted that as used herein and in the appended claims, the singular forms "a", "an", and "the" include plural referents unless the context clearly dictates otherwise. Thus, for example, reference to "a protein" includes more than one protein, and reference to "a compound" includes more than one compound. In describing and claiming the present invention, the following terminology will be used in accordance with the definitions set out below.

A polynucleotide is typically composed of a specific sequence of four nucleotide bases: adenine (A); cytosine (C); guanine (G); and thymine (T) (uracil (U) for thymine (T) when the polynucleotide is RNA). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When specified on an individual basis, the one-letter abbreviation is preceded by either a "d" or an "r," where "d" indicates the nucleoside is a 2'-deoxyribonucleoside and "r" indicates the nucleoside is a ribonucleoside. For example, "dA" designates 2'-deoxyriboadenosine and "rA" designates riboadenosine. When specified on an aggregate basis, the particular nucleic acid or polynucleotide is identified as being either an RNA molecule or a DNA molecule. Nucleotides are abbreviated by adding a "p" to represent each phosphate, as well as whether the phosphates are attached to the 3'-position or the 5'-position of the sugar. Thus, 5'-nucleotides are abbreviated as "pN" and 3'-nucleotides are abbreviated as "Np," where "N" represents A, G, C, T or U. When nucleic acid sequences are presented as a string of one-letter abbreviations, the sequences are presented in the 5'→3' direction in accordance with common convention, and the phosphates are not indicated. Thus, the term polynucleotide sequence is the alphabetical representation of a polynucleotide molecule. This alphabetical representation can be input into databases in a computer having a central processing unit and used for bioinformatics applications such as functional genomics and homology searching.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences in association therewith.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity.'" The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul. *Proc. Natl. Acad. Sci. USA* 87:2264-2268 (1990) and as discussed in Altschul, et al., *J. Mol. Biol.* 215:403-410 (1990); Karlin And Altschul, *Proc. Natl. Acad. Sci. USA* 90:5873-5877 (1993); and Altschul et al., *Nucleic Acids Res.* 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Default parameters are provided to optimize searches with short query sequences in, for example, blastp with the program. The program also allows use of an SEG filter to mask-off segments of the query sequences as determined by the SEG program of Wootton and Federhen, *Computers and Chemistry* 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80-85%, preferably 85-90%, more preferably 90-95%, and most preferably 98-100% sequence identity to the reference sequence over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., see Logan & Shenk, 1984, *Proc. Natl. Acad. Sci. USA* 81:3655-3659). Alternatively, the vaccinia 7.5 K promoter may be used, (see, e.g., Mackett et al., 1982, *Proc. Natl. Acad. Sci. USA* 79:7415-7419; Mackett et al., 1984, J. Virol. 49:857-864; Panicali et al., 1982, *Proc. Natl. Acad. Sci. USA* 79:4927-4931).

In the present disclosure, a recombinant AAV vector library is provided. While wild type AAVs (on which the library is based) can replicate in cells, the in vitro- and in vivo-selected isolates of the present disclosure are non-replicating and non-infectious. In other words, the viruses in the library contain only the Rep and Cap genes from wild type viruses, and do not contain any other reporter sequences such as GFP. After selection of the virus of interest according to the methods set forth herein, the recombinant Cap genes from the new isolates are cloned into plasmids for expressing the recombinant Cap proteins and packaging and production of non-replicating, non-infective vectors (a process also known as "vectorizing").

II. Chimeric AAV Capsid

Capsid proteins with regions or domains or individual amino acids that are derived from two or more different serotypes of AAV are described herein. A capsid protein can have a first region that is derived from or having high levels of sequence similarity or identity to a first AAV serotype or known recombinant AAV capsid protein (e.g., AAV-DJ), a second region similarly derived from or having high levels of sequence similarity or identity to a second AAV serotype or known recombinant AAV capsid protein, as well as third, fourth, fifth, six, seventh and eighth regions, etc. derived from or having high levels of sequence similarity or identity to another AAV serotype or known recombinant AAV capsid protein. The AAV serotypes may be human AAV serotypes or non-human AAV serotypes, such as bovine, avian, and caprine AAV serotypes. In particular, non-primate mammalian AAV serotypes, such as AAV sequences from rodents (e.g., mice, rats, rabbits, and hamsters) and carnivores (e.g., dogs, cats, and raccoons), may be used. By including individual amino acids or regions from multiple AAV serotypes in one capsid protein, capsid proteins that have multiple desired properties that are separately derived from the multiple AAV serotypes may be obtained.

In one embodiment, a capsid protein, referred to herein as "AAV-DJ", that has an amino acid sequence comprising a first region that is derived from a first AAV serotype (AAV-2), a second region that is derived from a second AAV serotype (AAV-8), and a third region that is derived from a third AAV serotype (AAV-9), is provided. The AAV-DJ capsid protein was identified from a library of capsid proteins, using a method described below, as well as in U.S. patent application Ser. No. 12/538,791, published as US Patent Publication No. 20100047174, incorporated by reference herein, in its entirety. It will be appreciated that the AAV-DJ protein is merely exemplary of the beneficial capsid proteins that can be obtained from a library generated according to the teachings herein, where the beneficial capsid proteins preferably have multiple desired properties that are derived from multiple AAV serotypes.

AAV-DJ has four mismatches to the two T cell epitopes in AAV-2 which have recently been identified as being involved in an anti-AAV cytotoxic T lymphocyte (CTL) response in humans. Thus, recombinant AAV vectors that include the AAV-DJ capsid protein or a derivative thereof are likely less immunogenic in humans than AAV-2 vectors that include the AAV-2 capsid.

Studies were conducted to confirm that infectious viral particles can be formed with AAV-DJ as the capsid. In a first study, the AAV-DJ nucleotide sequence was inserted into an AAV helper plasmid that also expresses the AAV-2 rep gene. 293 kidney cells were then co-transfected with the AAV helper plasmid and an adenoviral helper plasmid, as well as a gfp-expressing vector plasmid. For comparison, two different versions of an AAV-2 helper were used (designated AAV-2 "old" and AAV-2 "new") which differ in the expression levels of viral proteins. Three days after the co-transfection, Western blotting (with 303.9 (Rep) and B1 (capsid protein)) of the 293 cell extracts revealed the presence of presence of Rep and capsid proteins at levels comparable to those found in cells co-transfected with plasmids expressing the AAV-2, AAV-8, or AAV-9 capsid proteins.

In another study, particle infectivity and ability to avoid neutralization by human immune globulin (IVIG) of AAV-DJ clone was compared to wildtypes AAV-2, AAV-8, and AAV-9. Two different versions of an AAV-2 helper were used (designated AAV-2 old and AAV-2 new) which differ in the expression levels of viral proteins. Recombinant AAVs with either the AAV-DJ, AAV-2, AAV-8, or AAV-9 capsids were produced by triple transfecting cells with a plasmid encoding gfp flanked by AAV inverted terminal repeats (ITRs), a plasmid encoding adenoviral helper genes, and a plasmid encoding the AAV-2 Rep gene and either the AAV-DJ, AAV-2, AAV-8, or AAV-9 capsid protein, and then freeze-thaw lysing the cells. Each virus-containing lysate was then neutralized using a high dose (1:1 volume) of two different batches of human immune globulin (IVIG1 and IVIG2) (293 cells); (Huh-7 cells)), or three decreasingly lower doses (1:2 (high), 1:10 (med), and 1:25 (low) antiserum/virus) of the two different batches of human immune globulin (IVIG1 and IVIG2), or a monoclonal A20 antibody (293 cells), or a polyclonal anti-AAV-8 serum ("A8"). A20 is a monoclonal antibody that was raised against assembled AAV-2 capsids and anti-AAV-8 is a polyclonal rabbit serum raised against assembled AAV-8 capsids. Lysates treated with PBS were used as a control. The virus-containing lysates were neutralized by incubating the lysates with the human immune globulin or antibody for a period of time (one hour at room temperature (20-25° C.)) and then infecting cells in the presence of helper adenovirus. The remaining activity of the viruses after the neutralization period was determined by titrating gfp expression units on the cells.

In the absence of IVIG1, IVIG2, and A20, the AAV-DJ virus was at least as infectious on 293 cells as AAV-2 and several fold more infectious than AAV-2 on Huh-7 cells. It was demonstrated that the AAV-DJ virus and AAV-8 were able to partially escape neutralization by IVIG, while AAV-2 was not. AAV-9 had intermediate IVIG results relative to AAV-DJ/AAV-8 and AAV-2, and was neutralized at high IVIG doses. AAV-2 was neutralized by the A20 antibody, but the A20 antibody did not significantly affect AAV-DJ, AAV-8, or AAV-9. The polyclonal anti-AAV-8 antiserum neutralized all four capsids at high or medium doses, whereas AAV-2 and AAV-DJ partially escaped neutralization at the low dose.

In summary, it was previously found that the AAV-DJ virus was more infectious to Huh-7 cells than the previously known most efficient AAV on Huh-7 cells (AAV-2), even in the presence of high concentrations of human immune globulin. Also, the AAV-DJ virus was found to have improved resistance to neutralization by human immune globulin relative to AAV-2. Such resistance is reasonable, given that the AAV-DJ capsid was selected from a library partially based on its ability to produce virus that resist neutralization by human immune globulin. However, the improved resistance of the AAV-DJ virus to the A20 antibody was surprising and unexpected, because (i) it was not part of the selection scheme described below that was used to isolate AAV-DJ; and (ii) AAV-DJ shares substantial identity to AAV-2, which is neutralized by the A20 antibody.

In yet another study using human melanoma cell, in vitro infectivity of gfp-expressing vectors from the AAV-DJ capsid gene was compared to the in vitro infectivity of eight commonly used wildtype AAVs, AAV-1, AAV-2, AAV-3, AAV-4, AAV-5, AAV-6, AAV-8, or AAV-9. The melanoma cells were infected with $2 \times 10^9$ recombinant AAV particles of each serotype and gfp expression was visualized three days later. The results were quantitated, expressed as gfp expression in IU/mL, from virus titration on the melanoma cells (in 96-well plates) and the AAV-DJ vector was superior to the wildtype vectors, and, notably, substantially better than AAV-2.

A number of cell lines were infected with ten-fold serial dilutions of each serotype, or AAV-DJ or the DJ heparin mutant DJ/8, discussed below, expressing a gfp reporter gene. Vector preparations were normalized to contain $2 \times 10^9$ total (vector DNA-containing) particles per mL prior to infection. Three days later, gfp-expressing cells were counted and infectious titers determined, taking into account the dilution factor. AAV-DJ vectors showed the highest infectivity on many cell lines, and ratios of total to infectious particles were frequently far below 500, highlighting the extreme efficiency of AAV-DJ in vitro, and suggesting its particular usefulness for ex vivo gene transfer applications.

Vectors prepared with the AAV-DJ capsid were also tested in vivo for expression of a gene of interest. In a first study, recombinant human factor IX (FIX)-expressing AAVs with either the AAV-DJ, AAV-2, AAV-8, or AAV-9 capsids were produced by a triple transfection technique. Doses of $5 \times 10^{10}$, $2 \times 10^{11}$, and $1 \times 10^{12}$ (low, medium, and high, respectively)

recombinant viral particles were injected peripherally into immunocompetent mice (C57/BL6) and plasma hFIX was monitored for up to four months after injection. The FIX protein plasma levels were quantified by ELISA.

FIX levels over 1% are considered therapeutic in hemophilics. The AAV-8, -9 or -DJ vectors exceeded the 100% level already at the lowest dose. A dose-dependent expression from the AAV-DJ capsid at levels equivalent to AAV-8 and -9, the two naturally identified AAVs reported in liver, was observed. The three viruses readily outperformed the AAV-2 prototype at any dose and expressed over 100% of normal hFIX levels from intravenous injection of $5 \times 10^{10}$ particles, whereas AAV-2 expression was over 100% of normal hFIX levels only at a dose of $1 \times 10^{12}$.

In another study, recombinant human alpha-1-antitrypsin (hAAT)-expressing AAVs were prepared, from the AAV-DJ, AAV-2, AAV-8, or AAV-9 capsids. The hAAT gene was under an RSV promoter. Mice (C57/BL6) were injected via tail vein infusions of $2 \times 10^{11}$ particles and plasma levels of hAAT were determined via specific ELISA 3, 7, and 14 days after injection. AAV-8, AAV-9, and AAV-DJ expressed efficiently and equally outperformed the vector with an AAV-2 capsid.

In another in vivo study, liver transduction in the presence of human serum was quantified, to assess the ability of AAV-DJ to evade neutralization in vivo. Mice were passively immunized with 4 or 20 mg IVIG prior to infusion of hFIX-expressing AAV-2, -8, -9, or -DJ. Plasma hFIX levels for each AAV serotype were expressed as percent corresponding virus level in control mice treated with phosphate-buffered saline rather than IVIG as a function of time post infusion. AAV-2 expression was completely abolished, however transduction with AAV-DJ, -8 or -9 was inhibited in a dose-dependent manner, with AAV-DJ showing intermediate resistance at the high, and efficient evasion (similar to AAV-8 and AAV-9) at the low IVIG dose. These results were confirmed with a second independent IVIG batch from another vendor (Carimune 12%, Behring AG, data not shown).

In another study, the feasibility to repeatedly administer the different viruses to mice was assessed, to evaluate capsid cross-neutralization. No gene expression upon re-infusion of any of the capsids into animals already treated with the same serotype was observed. However, AAV-8 and -9 also efficiently blocked each other, substantiating previous data (Gao, G. et al., *J. Virol.*, 78:6381-6388 (2004)). This result might argue against the use of vectors based on these wildtypes in re-administration protocols, albeit they could be combined with AAV-2. In contrast, primary infusion of AAV-DJ allowed subsequent expression (up to 18%) from AAV-2, -8 or -9, likely due to the fact that AAV-DJ only shares a limited number of epitopes with each wildtype virus. In the reverse experiment, AAV-DJ vectors were inhibited in animals immunized with AAV-8 or -9, while giving detectable expression in AAV-2-treated mice. This implied a stronger or broader immune response from primary infusion of serotypes 8 or 9. AAV-DJ was more resistant to the corresponding mouse sera in culture. Less cross-reactivity between AAV-8 and -9 was noted. AAV-DJ, as well as other recombinant protein capsids identified in the library discussed below, retained a heparin binding domain (HBD) from the AAV-2 parent. This domain functions in binding to the primary AAV-2 receptor heparin sulfate proteoglycan (Summerford, C. et al., *J. Virol.*, 72:1438-1445 (1998)). To investigate the role of the AAV-DJ HBD, two crucial arginine residues (Kern, A. et al., *J. Virol.*, 77:11072-11081 (2003)) were mutated to the respective residues in AAV-8 or -9, and are referred to herein as AAV-DJ/8 and AAV-DJ/9. gfp expression was reduced by several orders of magnitude, and was as low as that observed with serotypes AAV-8 or AAV-9.

The infectivity drop was shown to correlate with a reduced binding to cells. A titration of infectious particles on 293 kidney cells illustrated the role of the HBD for infection in culture, as seen by the reduction in infectivity in the HBD mutants AAV-DJ/8 and AAV-DJ/9. Additional mutants were prepared and tested, and are identified herein as AAV-2/8 (HBD negative), AAV-8/2 (HBD positive), and AAV-9/2 (HBD positive). Cell binding assays confirmed the role of the HBD for attachment to cultured cells, where the drop in binding with the mutants correlated with the transduction data. The HBD-positive AAV-8 and AAV-9 mutants bound several fold more efficiently than AAV-2 on HeLa cells but transduced less efficiently. Thus, cell attachment alone cannot explain the unusual infectivity of AAV-DJ. Instead, a synergistic effect from sharing beneficial properties from AAV-DJ parents is contemplated, resulting in enhancement of multiple steps in AAV-DJ transduction. The HBD also was shown to influence biodistribution, as shown in Table 1.

TABLE 1

Relative transduction of non-hepatic tissues with AAV vectors

|  |  | Lung | Heart | Kidney | Spleen | Brain | Pancreas | Gut | Muscle |
|---|---|---|---|---|---|---|---|---|---|
| AAV-2 | 1e12 | nd | 0.7 ± 0.1 | 0.8 ± 0.1 | 0.2 ± 0.0 | nd | nd | nd | nd |
|  | 7e12 | nd | 1.5 ± 0.3 | 2.0 ± 0.3 | 1.0 ± 0.2 | nd | nd | nd | nd |
| AAV-8 | 1e12 | 0.5 ± 0.0 | 1.2 ± 0.2 | 0.9 ± 0.2 | 0.3 ± 0.0 | 0.2 ± 0.0 | 0.2 ± 0.0 | 0.3 ± 0.0 | 0.7 ± 0.1 |
|  | 7e12 | 2.5 ± 0.3 | 2.5 ± 0.2 | 2.6 ± 0.3 | 1.5 ± 0.2 | 1.5 ± 0.2 | 1.2 ± 0.2 | 1.2 ± 0.2 | 1.9 ± 0.2 |
| AAV-9 | 1e12 | 0.7 ± 0.1 | 1.3 ± 0.2 | 1.1 ± 0.2 | 0.4 ± 0.0 | 0.2 ± 0.0 | 0.2 ± 0.0 | 0.3 ± 0.0 | 0.8 ± 0.1 |
|  | 7e12 | 2.6 ± 0.3 | 3.6 ± 0.4 | 3.8 ± 0.4 | 1.5 ± 0.2 | 1.8 ± 0.2 | 1.3 ± 0.2 | 1.9 ± 0.2 | 3.0 ± 0.3 |
| AAV-DJ | 1e12 | 0.2 ± 0.0 | 1.3 ± 0.2 | 0.8 ± 0.2 | 0.5 ± 0.1 | nd | 0.1 ± 0.0 | 0.1 ± 0.0 | 0.2 ± 0.0 |
|  | 7e12 | 0.6 ± 0.1 | 2.3 ± 0.2 | 2.1 ± 0.2 | 1.5 ± 0.2 | 0.4 ± 0.0 | 0.5 ± 0.0 | 0.5 ± 0.0 | 0.8 ± 0.1 |
| AAD-DJ/8 | 1e12 | 0.6 ± 0.0 | 1.3 ± 0.2 | 0.8 ± 0.2 | 0.2 ± 0.0 | 0.2 ± 0.0 | 0.1 ± 0.0 | 0.2 ± 0.0 | 0.7 ± 0.1 |
|  | 7e12 | 2.6 ± 0.3 | 2.5 ± 0.3 | 2.3 ± 0.3 | 1.6 ± 0.3 | 1.8 ± 0.2 | 1.2 ± 0.2 | 1.3 ± 0.2 | 2.0 ± 0.2 |

Vector copy numbers (per diploid genomic equivalent) were determined via Phosphoimager scan analyses of Southern Blots. At least three independent mice were analysed per dose. Copy numbers are shown in percent (rounded to one decimal, plus standard deviations) relative to those in liver within each group, allowing comparison between vectors and doses.
For AAV-2, most signals were below the detection limit of the Southern Blot analyses (~0.03 copies of double-stranded AAV DNA per cell), preventing calculation of relative transduction in these cases (nd = not determined).
Grey shadows highlight doses/tissues where relative AAV-DJ transduction differed by at least 2-fold from serotypes 8 and 9, as well as the AAV-DJ HBD mutant.

AAV-8 and -9 (HBD-negative) demonstrated an unrestricted tropism, readily transducing all tested tissues at $1\times10^{12}$ particles per mouse. In striking contrast, AAV-2 and likewise AAV-DJ (both HBD-positive) were restricted to liver and, to a lesser extent, heart, kidney and spleen, and near or below detection limit in other tissues. Quantification of double-stranded vector DNA (using liver as an internal standard in each group) showed that AAV-DJ transduced lung, brain, pancreas and gut about 2- to 4-fold less efficiently than wildtypes 8 or 9. The effect of the HBD on viral tropism was best exemplified by comparing AAV-DJ to the DJ/8 mutant: HBD deletion alleviated the liver restriction and expanded transduction to nonhepatic tissues, identical to AAV-8 and -9, and including the brain. These findings corroborate and explain a series of reports on wide tissue dissemination of vectors based on HBD-negative natural serotypes (AAV-1 and -4 to -9) in mice, dogs and monkeys, in contrast to the HBD-positive AAV-2. Notably, AAV-DJ also transduced nonhepatic tissues at the maximum dose of $7\times10^{12}$ particles, but still to a lesser extent than the HBD-negative viruses, in particular AAV-9. Even at this dose, brain and also lung transduction remained marginal.

While the embodiments described above are primarily with respect to an rAAV capsid protein, it is recognized that capsids having amino acid and/or nucleotide sequences that are similar in sequence and having the same function may be used and are contemplated. In one embodiment, a recombinant capsid protein having at least about 60% sequence identity, further at least about 70% sequence identity, at least about 75% sequence identity, at least about 80% sequence identity, at least about 85% sequence identity, at least about 90% sequence identity, at least about 95% identity, at least about 96% sequence identity, at least about 97% sequence identity, at least about 98% sequence identity, or at least about 99% sequence identity to the amino acid sequences identified in the sequence listing is contemplated.

It will be appreciated that conservative amino acid substitutions may be in the polypeptide sequence, to achieve proteins having, for example, 60%, 70%, 75% 80%, 85%, 90%, 95%, 96%, 97%, 98% or 99% sequence identity to a polypeptide encoded by a nucleotide sequence disclosed herein, and preferably with retention of activity of the native sequence. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, amino acids having acidic side chains, such as aspartic acid and glutamic acid, are considered interchangeable herein with amino acids having amide side chains, such as asparagine and glutamine.

A mouse model system that is severely immunodeficient has been developed. These fumarylacetoacetate hydrolase (Fah)-deficient mice can be pretreated with a urokinase-expressing adenovirus, and then highly engrafted (up to 90%) with human hepatocytes from multiple sources, including liver biopsies. Furthermore, human cells can be serially transplanted from primary donors and repopulate the liver for at least four sequential rounds. The expanded cells displayed typical human drug metabolism. This system provides a robust platform to produce high-quality human hepatocytes for tissue culture. It may also be useful for testing the toxicity of drug metabolites and for evaluating pathogens dependent on human liver cells for replication. (Azuma, et al., (2007) *Nature Biotech.* 25:903-910).

A humanized mouse model, known as FRG mice (Yecuris Corporation, Portland, Oreg.), has been designed to allow researchers to grow and expand populations of human hepatocytes in vivo for research and drug testing. The FRG model has the genes Fah, Rag, and Ilrg knocked out. Knocking out Fah yields mouse liver damage, the lack of Rag removes the part of the innate immune system that rejects other mouse cells, and knocking out Ilrg inactivates the part of the immune system that would prevent engraftment of cells from other species including humans. Thus, the FRG mouse can either be repopulated with human donor cells of choice or repopulated from a pool of prequalified donors. Animals can be provided with human hepatocytes that range from 5-95% of the total liver mass. Nonrepopulated FRG mice are also available for use as study controls.

In one embodiment, the recombinant AAV capsid protein is comprised of a first sequence of amino acid residues from a first AAV serotype, and at least a second sequence of amino acid residues from a second AAV serotype. The first sequence is, in the embodiment, a conserved set of amino acids from a contiguous sequence of amino acids from the first AAV serotype. The second sequence is a conserved set of amino acids from a contiguous sequence of amino acids from the second AAV serotype. A "conserved set" of amino acids refers to a contiguous sequence of amino acids that is identical or closely homologous to a sequence of amino acids in the AAV serotype. In one embodiment, close homology intends at least about 80% sequence identity. In one embodiment, close homology intends at least about 90% sequence identity. A contiguous sequence of amino acids in such a conserved set may be anywhere from 2 to 500, 2 to 400, 2 to 300, 2 to 200, 2 to 100, or 2 to 50 amino acid residues in length.

It will also be appreciated that the recombinant vectors described herein are contemplated for use in methods of expressing a gene of interest in a variety of cells and in a mammal. Transduction into cells lines in addition to the cell lines described herein are exemplary, and other cells lines, particularly stem cells, are contemplated. In terms of in vivo use, the method preferably comprises introducing a recombinant AAV (rAAV) into a mammal, the recombinant AAV vector encoding the gene of interest and comprising a capsid protein having an amino acid sequence selected from the group of sequences identified in the sequence listing accompanying the present disclosure. The vector expressing a gene of interest is introduced to the mammal, typically by injection, intravenously, subcutaneously, parenterally, or the like. The gene of interest can be any gene, and many suitable genes for expression for therapeutic or non-therapeutic purposes are readily identified by a skilled artisan. The nucleotide sequence of the gene of interest is typically "operably linked" to one or more other nucleotide sequences, including but not limited to the gene for a selected capsid protein, a promoter, and enhancer, and the like.

A gene is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous. Additionally, as defined herein, a nucleotide sequence is intended to refer to a natural or synthetic linear and sequential array of nucleotides and/or nucleosides, and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a polypeptide.

III. Generation of a Library of Novel AAV Capsids

In another aspect, a method of generating a library of novel AAV capsids is provided. Embodiments of this aspect include a method of isolating a recombinant AAV plasmid that includes a novel AAV capsid.

A method of generating a library of novel rAAV capsids is provided by the present disclosure, including the figures and sequence listing. Isolated nucleic acids encoding capsid genes are obtained using primers designed to include a serotype-specific part fused with common signature regions that flank the capsid nucleic acid sequence. Then, the isolated nucleic acids are digested or fragmented, such as with DNAseI, into fragments of, for example, between about 0.2 and about 1.0 kb. The fragments are then re-assembled into larger pieces by performing PCR, such as with Taq polymerase, in the absence of additional primers. Because of the related nature of the fragmented genes, the gene fragments have overlapping regions of homology that allow the fragments to self prime in the absence of additional primer. After multiple rounds of PCR, products having a length approximately equal to that of the originally capsid genes are obtained. The PCR products include hybrid products that contain novel rAAV capsid regions.

The full length PCR products are then PCR amplified, with Platinum Pfx polymerase or other polymerase, using primers that bind to the signature regions that are contained in the full length PCR products because they were present in the original primers used to isolate the capsid nucleic acid sequences. The PCR products from this amplification step are then cloned into a conventional plasmid, to provide a library of novel AAV capsid genes. In one embodiment, the capsid genes are cloned into an ITR-rep-containing AAV plasmid, to subsequently create the actual viral library.

A method of isolating a recombinant AAV that includes a novel recombinant AAV capsid, i.e., a "rAAV capsid" is isolated as described above. Hybrid capsid sequences are cloned into a plasmid that is capable of producing an infectious AAV genome, such as a plasmid comprising the AAV-2 rep gene, as well as the two AAV-2 ITRs. The plasmid library is transfected into cells, in some embodiments with an adenoviral helper plasmid to produce virus. The virus is then amplified in cells in the presence of a helpervirus, such as wildtype Adenovirus-5 helpervirus. The virus may be amplified in the presence of one or more forms of selective pressure, such as in the presence of human immune globulin. The viruses that survive multiple passages under the selective pressure are chosen for further study or use.

This approach was used to generate a library for selection in vitro on hPAEC cells. In brief, the capsid gene from ten different AAV serotypes (AAV-1, AAV-2, AAV-3B, AAV-4, AAV-5, AAV-6, AAV-8, AAV-9, avian AAV, and bovine AAV) was fragmented, and the PCR products were blunt cloned into the pCR4-TOPO plasmid, available from Invitrogen. Twenty-four (24) subclones were sequenced to confirm that capsid sequences that are a hybrid of different serotypes were created. Sequences from all ten of the serotypes were represented in the subclones. Typically, the hybrid capsid sequences included sequences from at least two, and often, more than six, of the serotypes. The capsid sequences in the pCR4-TOPO plasmid were then subcloned into a plasmid comprising the AAV-2 rep gene, as well as the two AAV-2 ITRs, that was then used to transform bacteria. It is estimated that approximately a library of $3 \times 10^4$ hybrid AAV capsid gene variants were obtained from a single reaction and from 10 plates of bacteria. Up-scaling (including plating on 100 plates of bacteria) resulted in a plasmid library of approximately $6.9 \times 10^5$ clones. This plasmid library was then co-transfected into 293 human embryonic kidney cells together with an adenoviral helper plasmid, to produce a viral library of hybrid AAV particles.

Various amounts of purified shuffled AAV were incubated with PAEC cells at a range of MOIs (Multiplicity Of Infection), and subsequently infected with helper virus needed for AAV replication (in this case wild type human Adenovirus). Ideally, the Adenovirus would lyse the cells within three days, giving the AAV sufficient time to replicate and newly synthesized Ad virus was released into the media. Media was collected 3 days after infection and used directly for western blot analysis using antibody specific for AAV CAP proteins VP1, VP2, and VP3. In order to avoid cross-packaging (a phenomenon specific to closely related AAVs), the sample with the lowest, but detectable, level of VP proteins based on the Western blot was selected for the next round of selection. This helped to optimize the stringency of the library in each amplification round, by ensuring that a single viral genome was delivered to each cell, and subsequently packaged into the capsid expressed from its own genome. Before the next round of selection, the supernatant was heated to 65 C for 30 min., to inactivate more temperature-sensitive Ad virus without affecting the AAVs present in the sample.

The selected library of AAV capsid variants was then co-infected with wildtype Adenovirus-5 helpervirus and successfully amplified in on of several possible cell lines known in the art. Successful amplification of the viral library was confirmed by Western blots of whole cell extracts using the B1 antibody which recognizes an eight amino acid epitope that is largely conserved over most known AAV serotypes, and thus should be present in the majority of the hybrid AAVs described herein. Replicating AAV particles were detected in all of the tested cell lines for up to five consecutive passages. Whole freeze-thaw cell extracts were used for infecting fresh cells each time. To date, the viral library has also been successfully passaged six times in primary human hepatocytes, which are notoriously difficult to infect with vectors based on wildtype AAVs.

The viral library was also amplified in human Huh-7 cells in the presence of human immune globulin (IVIG). It was found that the specific IVIG used (IVIG Gamimune®N 10% from Bayer) contained abundant neutralizing antibodies against AAV-2 and AAV-3, as well as some antibodies against AAV-1, AAV-4, AAV-5, and AAV-6. Thus, amplification in human Huh-7 cells in the presence of IVIG provided a selective pressure for AAV hybrids comprising domains from different serotypes since selecting for a high efficiency infection of Huh-7 cells favors AAV-2 domains, while selecting for escape from IVIG neutralization favors AAV-8 and AAV-9 domains. The selection was successful, as it was found that with increasing passages of the library, an increasing tolerance to IVIG was achieved. After the fourth passage, surviving virus could be amplified in the presence of 500 µL IVIG, while after the first passage, surviving virus could only be amplified in the presence of approximately 10 µL IVIG.

After the 5$^{th}$ passage, the hybrid capsid sequences were PCR amplified and blunt cloned in pCR4-TOPO. The capsid sequences from 96 colonies were sequenced and found to be identical. The hybrid capsid sequence is the AAV-DJ sequence described above.

Thus, a plasmid library was created using DNA Family Shuffling (Crameri, et al., *Nature*, 391: 288-291 (1998)) of parental AAV capsid genes. Subsequently, a viral library was generated, by transfecting the plasmid library into cells together with an adenoviral helper plasmid. This second viral library was then subjected to selection pressure, to isolate specific candidates. From those, selected shuffled capsid genes were isolated and subcloned into an AAV helper plasmid, to make recombinant AAV vectors comprising the hybrid capsid. More particularly, DNA Family shuffling was used to create a complex library of hybrid particles from ten different wildtypes. Serial amplification on human cells enriched hybrids from a multitude of AAV serotypes. The AAV-2-8-9 chimera referred to as AAV-DJ was found to be superior to natural AAVs in cultured cells and outperformed the AAV-2 prototype in tissue in vivo. Vectors with an AAV-DJ capsid were superior in vitro and gave a robust and specific in vivo performance, and provided an ability to evade humoral neutralization by human serum. Furthermore, several isolates from the in vitro- and in vivo-selected AAV libraries generated according to the methods described herein were found to outperform the AAV-DJ capsid previously described.

After several rounds of selection, a single clone was observed. This new AAV isolate was dubbed "AAV-PAEC." Later, additional AAV-PAECs were isolated, and AAV-PAEC2, AAV-PAEC4, AAV-PAEC6, AAV-PAEC7, AAV-PAEC8, AAV-PAEC11, AAV-PAEC12 and AAV-PAEC13 isolates are identified herein.

The AAV library was also screened in vivo in humanized FRG mice. Animals were injected with different amounts of AAV library, followed by injection of a fixed amount of wtAd5 virus. After three days, animals were sacrificed, and their livers extracted, homogenized and frozen in aliquots. One aliquot from each animal was used for analysis by western blot using anti-VP1-2-3 CAP antibody for detection. Once the animal with the lowest, but detectable signal, was identified, another frozen aliquot of liver from that animal was processed, and cleared liver lysate was injected in different amounts into another group of animals. As in the in vitro experiment described in Example 1, in order to inactivate hAd5 present in the lysate, the liver lysate was incubated at 65 C for 30 min. prior to injection into another cohort of animals.

With each round of selection, 100-150 clones were sequenced. AAV DNA was isolated from liver lysate and used to sequence the CAP genes present in the pool. The library was found to be highly variable in the early stages of in vivo selection, whereas in the later rounds of selection, a positive selection for certain AAV clones in the AAV library clearly occurred.

Several novel rAAVs with high efficiency were identified and sequenced. Also valuable are specific novel rAAV serotypes selected in vitro in human pulmonary arterial endothelial cells.

IV. Examples

The following examples are illustrative in nature and are in no way intended to be limiting. For technical procedures, reference can be made to U.S. patent application Ser. No. 12/538,791, published as US 20100047174, which is incorporated by reference herein, in its entirety, as well as to Grimm, D. et al., (*Blood*, 102:2412-2419 (2003)).

Example 1

AAV Capsid Library Generation

A. Plasmids for AAV Capsid Library Generation

Plasmids containing full-length capsid (cap) genes of ten different wild type (wt) AAV serotypes were obtained, namely, AAV-1, -2, -3B, -4, -5, -6, -8, -9, avian and bovine AAV and goat AAV, which was partly synthesized (GeneArt, Regensburg, Germany) as a 888 nt fragment (nt 1023 to 1910). This subclone spans the entire right half of the goat AAV capsid protein, which comprises all 42 reported differences between goat AAV and AAV-5. These cap genes were initially amplified via PCR and subcloned into pBlueScript II SK (Stratagene). (See FIG. 1). The purpose was to flank all cap genes with sites for the unique restriction enzymes Pac I (5') or Asc I (3'), to facilitate later cloning of "shuffled" cap genes into a wildtype AAV plasmid. All primers also contained either a Hind III (5') or a Spe 1 (3') site, to allow directed cloning into pBlueScript (none of the four restriction enzymes cuts in any parental cap gene). A 20 nt signature region was inserted between the two restriction sites in each primer, to provide conserved primer binding sites for later PCR amplification of shuffled genes.

In parallel, a wildtype cap recipient plasmid was engineered to contain the AAV-2 packaging elements (ITRs) flanking the AAV-2 rep gene (encoding AAV replication proteins), together with Pac I and Asc I sites for cap cloning, and the AAV-2 polyadenylation site. Therefore, AAV-2 rep (nt 191 to 2189) was PCR amplified using primers containing Bgl II sites and then subcloned into pTRUF3 (carrying AAV-2 ITRs with adjacent Bgl II sites).

B. DNA Family Shuffling of AAV Capsid Genes

For DNA shuffling of AAV capsid genes, a 2-step protocol was used where the parental genes were first fragmented using DNase I enzyme and then reassembled into new full-length genes via primer-less PCR. This was followed by a second PCR including primers binding outside of the cap genes, allowing their subcloning into the wildtype recipient ITR/rep plasmid for packaging into an AAV library. Initially, all cap genes were isolated from the subclones via Hind III/Spe I digestion (Eco RI for goat AAV) and then reaction conditions were optimized as follows. Various DNAse I concentrations and incubation times were tested, aiming to obtain a pool of fragments between 0.2 and 1.0 kb in size. Optimal conditions found were: 1 µg per cap gene, 1 µL 1:200 pre-diluted DNase I (10 U/µL, Roche), 50 mM Tris Cl pH 7.4, 1 mM MgCl$_2$, total volume of 50 µL. The reaction was incubated for 2 min at room temperature and then stopped by heat inactivating at 80° C. for 10 min. Fragments of the desired sizes were isolated by running the entire reaction on a 1% agarose gel (total final volume ~60 µl). The re-assembly PCR reaction was then optimized by testing various DNA polymerases (Pfx Platinum, Stratagene; DeepVent, NEB; Taq, Amersham) and respective conditions. Best results were obtained using PuReTaq Ready-To-Go PCR Beads (Amersham) and the following conditions: 25 µL purified cap fragments, program: 4 min 95° C., 40 cycles (1 min 95° C., 1 min 50° C., 3 min 72° C.), 10 min 72° C., 10 min 4° C. Agarose gel (1%) analysis of 1 µL from this reaction typically showed a smear up to 5 kb and no distinct bands. The same three polymerases as above were then evaluated for the primer-containing second PCR, and the following conditions were found optimal: 1 µL Pfx Platinum, 2 µL product from first PCR, 1 mM MgSO4, 1 µg of each primer (see below), 0.3 mM each dNTP, total volume 50 µL, program: 5 min 94° C., 40 cycles (30 sec 94° C., 1 min 55° C., 3 minutes 68° C.), 10 min 68° C., 10 min 4° C. The primers used bound to the 20 nt signature regions described in the previous chapter. This reaction gave a distinct ~2.2 kb full-length cap band (1% agarose gel), which was purified (60 µL total) and cloned (4 µL) using the Zero Blunt TOPO PCR cloning kit (with electro-competent TOP10 cells) (Invitrogen, Carlsbad, Calif., USA). This intermediate cloning step significantly enhanced the yield of shuffled cap genes, as compared to efforts to directly clone the PCR product via conventional means (data not shown). The shuffled cap genes were then released from the TOPO plasmid via Pac I and Asc I double digestion and cloned into the appropriately digested ITR/rep recipient plasmid. Performing these reactions under minimal conditions (volumes and amounts), a library of approximately $3 \times 10^4$ bacterial colonies was obtained. Up-scaling of each step (including final plating on 100×15 cm plates) resulted in a final library of ~$6.9 \times 10^5$ plasmid clones. Its integrity, genetic diversity and functionality was confirmed by DNA sequencing and small scale expression studies. From the latter, it was determined by extrapolation that the viral library (below) retained >90% viability.

C. Selective in vitro Amplification of the Capsid Library
Experimental Design:

Various amounts of purified shuffled AAV were incubated with different cell lines (in 6 cm dishes), together with varying amounts of helper Adenovirus type 5. Ideally, the Adenovirus would lyse the cells within three days, giving the AAV sufficient time to replicate. The AAV amounts were adjusted to obtain minimal signals in Western blot analyses of cell extracts. This helped to optimize the stringency of the library in each amplification round, by ensuring that a single viral genome was delivered to each cell, and subsequently packaged into the capsid expressed from its own genome.

In the present study, cells of interest (PAEC cells) were infected with AAV library at range of MOIs (Multiplicity Of Infection) and subsequently infected with helper virus needed for AAV replication (in this case wild type human Adenovirus). AAV replication depends on Ad virus replication. Ad virus leads to cell lysis and release of newly synthesized Ad virus into the media. This process releases also newly synthesized AAV viruses. Media was collected 3 days after infection and used directly for western blot analysis using antibody specific for AAV CAP proteins VP1, VP2, and VP3. In order to avoid cross-packaging (a phenomenon specific to closely related AAVs), the sample with the lowest, but detectable, level of VP proteins based on the Western blot was selected for the next round of selection. Before the next round of selection, the supernatant was heated to 65 C for 30 min., to inactivate more temperature-sensitive Ad virus without affecting the AAVs present in the sample.

D. AAV Protein Analyses

Western blot and immunofluorescence analyses were carried out as reported (Grimm, D. et al., *Blood*, 102:2412-2419 (2003)) using the monoclonal B1 antibody for detection of immobilized AAV capsid proteins, useful because its eight amino acid epitope is largely conserved across known AAV serotypes.

Western blots from Round-1 and Round-2 of AAV library selection on human PAEC cells are shown in FIG. 3. Two AAV libraries, called "Library 1" or "Lib1" and "Library 2/3" or "Lib2/3" were used in the screen. Library 1 had significantly lower titer than Library 2/3. In FIG. 3, the numbers above each lane indicate the amount in microliters [µl] of each library used per 500 µl total infection, and "+Ad" and "−Ad" indicate (−)Library control groups treated (+) or not treated (−) with Ad, respectively. Samples selected for next rounds of AAV library selection are indicated by boxes, as well as bold and underlined type.

Similarly, FIG. 4 shows Western blots from Round-2 and Round-3 of AAV library selection. The specific signal in samples from Library 2/3 can be seen to be weak, while specific signal in the samples from Library 1 are strong. FIG. 5 shows data from Round-3 and final Round-4 of the AAV library selection in hPAEC cells.

At each round of selection, the supernatant harvested was used to isolate AAV DNA for sequencing analysis of the CAP genes present in the pool. Twenty-five to thirty random clones were sequenced at each round, including the starting Library1. Results are shown in FIG. 6, which indicates the percentage of the pool each different clone represents, at each round of selection. As can be seen in FIG. 6, all twenty-five clones sequenced from Library1 were different, while with each round of selection specific accumulation of a single clone can be observed. After Round-4, all thirty clones sequenced were of identical sequence. This new AAV isolate was dubbed "AAV-PAEC."

FIGS. 7 and 8 show the relatedness of the AAV-PAEC to wild-type AAV serotypes. FIG. 7 illustrates that AAV-PAEC is most closely related to AAV1 and AAV6, with the most 5' region of the CAP gene (or N region of the protein) being derived from AAV-3B. AAV1 and AAV6 are very similar to each other on amino acid level, and thus (as illustrated in FIG. 8), it is possible to look at AAV-PAEC as if it was derived from AAV-3B and AAV1, or from AAV-3B and AAV6; in each case, three amino acids differ in AAV-PAEC as compared to AAV1 or AAV6.

FIG. 9 shows a predicted 3D structure of AAV-PAEC (based on solved structure of part of AAV2 VP3 protein), assuming that AAV-PAEC is composed of sequences from AAV3B and AAV6 (see FIG. 8). The 3 mutations at positions 418, 531 and 584 are shaded gray.

Example 2

In vivo Studies

The AAV library generated according to the example above and screened to select new AAV isolates in vitro in human pulmonary artery endothelial cells (hPAEC) was then screened in vivo in humanized FRG mice, according to methods described below.

Experimental Design of in vivo AAV Library Selection

Similar to the in vitro AAV selection scheme described in Example 1, the AAV shuffle library was screened in FRG mice. As shown in FIG. 10, animals were injected with different amounts of AAV library, followed by injection of a fixed amount of wtAd5 virus. After three days, animals were sacrificed, and their livers extracted, homogenized and frozen in aliquots. One aliquot from each animal was used for analysis by western blot using anti-VP1-2-3 CAP antibody for detection. Once the animal with the lowest, but detectable, signal, was identified, another frozen aliquot of liver from that animal was processed, and cleared liver lysate was injected in different amounts into another group of animals. As in the in vitro experiment described in Example 1, in order to inactivate hAd5 present in the lysate, the liver lysate was incubated at 65 C for 30 min. prior to injection into another cohort of animals.

The experimental design shown in FIG. 10 was modified so that at each round of selection one or two humanized FRG animals were used (FIG. 11). Liver lysates from each animal in the in vivo AAV selection were analyzed by CAP-specific PCR. As can be seen in FIG. 12, the CAP specific band (~2.2 kb) was present in all humanized FRG animals used in the study, and the intensity of the signal is strong in all samples. In control non-humanized FRG animals, the CAP specific signal is lost after 3 rounds of selection, indicating that no AAV specific amplification was observed in those animals (this was expected, as human Ad5 virus required for AAV replication does not infect/replicate in mouse cells, but only in human cells, thus supporting AAV replication only in human hepatocytes present in humanized FRG animals). This control further shows that in humanized FRG animals the AAV selection took place in human hepatocytes but not in mouse cells.

With each round of selection, AAV DNA was isolated from liver lysate and used to sequence the CAP genes present in the pool. FIG. 13 compares data for (1) the AAV library injected into the first animal, (2) the lysate obtained from the first animal, and (3) the lysate from the fourth animal. At each round 100-150 clones were sequenced. Most of the clones sequenced from the library and from Mouse-1 were different from each other, showing high variability of the library at the early stages of in vivo selection (such a large number of different clones were identified in the library and in Mouse-1 that they are represented as a solid black bar in the graphic representation shown here). In Mouse-4, however, over 24% of sequenced clones were of identical sequence, showing a positive selection for certain AAV clones present in the AAV library.

Upon in vivo selection of rAAV serotypes on human hepatocytes in a mouse with a humanized liver, several novel rAAVs with high efficiency were identified and sequenced. Also valuable are specific novel rAAV serotypes selected in vitro in human pulmonary arterial endothelial cells (such as, for example, but not limited to AAV-PAEC2, AAV-PAEC4, AAV-PAEC6, AAV-PAEC7, AAV-PAEC8, AAV-PAEC11, AAV-PAEC12 and AAV-PAEC13 isolates).

FIG. 14 illustrates a reconstruction of the genealogical relationship between one of the in vivo isolates, AAV-LK01 and wildtype AAVs used to generate the library (as shown in FIG. 1). AAV-LK01 is most closely related to AAV8. The bottom of FIG. 14 graphically represents the predicted origin of various regions of the new isolate based on the identity of certain amino acid residues in these regions that correspond to residues within wildtype AAVs.

FIG. 15 shows a predicted 3-D structure of AAV-LK01 (based on solved structure of part of AAV2 VP3 protein). Point mutations indicated in FIG. 14 are shaded gray in the 3D model.

In order to better predict the characteristics of new in vivo-selected AAV isolates and to gain some insight into the receptor used by such isolates to bind/enter cells, we compared their sequences to wildtype AAV-2, specifically looking at the amino acids responsible for heparin binding. The residues implicated in heparin binding in AAV2 were compared to residues in new isolates AAV-PAEC and AAV-LK01. The AAV sources of the amino acids in new AAVs at indicated positions are given in parenthesis in FIG. 16. The whole region of the AAV-LK1 where those residues are located was derived from AAV8, and thus one can predict that AAV-LK01 will closely resemble AAV8 when it comes to the choice of a receptor. AAV-PAEC, on the other hand, differed significantly from AAV2, and each of the residues could have been derived from number of other AAVs, with AAV1 and AAV6 contributing to each of the 6 residues implicated in heparin binding. Thus, AAV-PAEC might be predicted to use the same or similar receptor as AAV1 and/or AAV6.

FIG. 17 shows a reconstruction of the genealogical relationship between the top three in vivo-selected isolates, AAV-LK01, AAV-LK02 and AAV-LK03 and wildtype AAVs used to generate the library. AAV-LK01 was found to be most closely related to AAV8, AAV-LK02 to AAV1 and AAV6, and AAV-LK03 to AAV3B.

FIG. 18 graphically represents the sequence of AAV-LK02 and the identity of corresponding amino acid residues in the new isolate as compared to various wildtype AAVs. AAV-LK02 appears to be mostly derived from AAV1 (or AAV6— due to very high % homology between AAV and AAV6), with the exception of a hyper-variable 50 amino acid (aa) region between amino acid nos. 450-500. The table shows each of the mutations in the 50 aa region in the left column, and indicates the possible parental wildtype AAV from which this residue was derived in the right column. Several mutations cannot be traced back to any of the parental AAVs, and were most probably caused by random mutations during the PCR used to generate the library, or were introduced during the viral replication, and are thus results of a natural viral evolution process.

FIG. 19 shows a predicted 3-D structure of AAV-LK02 (based on solved structure of part of AAV2 VP3 protein). Point mutations identified in FIG. 18 are shaded gray in this 3-D model.

FIG. 20 graphically represents of the sequence of AAV-LK03 and the identity of corresponding amino acid residues in the new isolate as compared to various wildtype AAVs. AAV-LK03 appears to be mostly derived from AAV3B with the exception of a hyper-variable region in the 5" of the gene and a single point mutation at the 3' end of the gene. The table shows each of the mutations in the left column, and indicates the possible parental wildtype AAV from which this residue was derived. Several mutations cannot be traced back to any of the parental AAVs, and were most probably caused by random mutations during the PCR used to generate the library, or were introduced during the viral replication, and are thus results of the natural viral evolution process.

FIG. 21 presents a reconstruction of the genealogical relationship (on the DNA level) between the AAVs identified during in vivo library selection, and wildtype AAVs used to generate the library.

FIG. 22 presents a reconstruction of the genealogical relationship (on the amino acid level) between the AAVs identified during in vivo library selection, and wildtype AAVs used to generate the library.

FIGS. 23A and 23B show a comparison of the new isolates (from selection in PAEC cells as well as from in vivo selection), which were vectorized (i.e., packaged into non-infectious, non-replicating recombinant vectors) and further studied in a side-by-side comparison. Each AAV isolate and the ten wildtype AAVs used to generate libraries were produced in three independent small-scale productions (n=3) and the titer of each vector was determined by extracting DNA from the vector and quantifying it by dot blot using a known amount of DNA as a standard. Dot blot titers were determined for the isolates as well as the wildtype AAVs. FIG. 23B presents this data in graphical form.

As shown in FIG. 24A, the vectorized AAV isolates and wildtype AAVs made in the three independent small-scale productions were used to transduce Huh7.5 cells, and the transduction titers determined. The vectors expressed eGFP under an hEF1 promoter. Transduction titer was calculated using the following formula: (% GFP/100)*dilution factor*cell number. FIG. 24B presents a graphic representation of the transduction titers on Huh7.5 cells. From the data, it can be seen that AAV-DJ is significantly better at transducing Huh7.5 cells than any of the wildtype AAVs. Of the new isolates, AAV-LK03 was found to transduce Huh7.5 cells at least 10 times better than AAV-DJ, and almost two logs better than any of the wildtype AAVs. AAV-PAEC is also significantly better at transducing Huh7.5 cells than any of the wildtype AAVs.

Dot blot titer is a physical titer that does not depend on the cell type, but rather represents the number of intact AAV particles containing AAV genome in the vector preparation. Using dot blot titer and the number of μl of each preparation used to transduce the cells, the transduction efficiency per number of viral genomes used for transduction (Transduction titer/vg) can be calculated. In order to better compare the transduction efficiency of the new AAV isolates on Huh7.5 cells, the transduction efficiency was normalized to the vector titers obtained from a dot blot. Results are presented in FIG. 25A. The results can also be represented by normalizing one of the vectors to a value of 1 (assigning value of 1 to the vector with the lowest transduction/vg). Results represented in this way are shown in FIG. 25B. FIG. 25B is a graphical representation of the transduction/vg on Huh7.5 cells normalized to the vector with the lowest transduction/vg (in this case AAV-LK04). Presented thusly, the graph in FIG. 25B shows fold increase in transduction/vg compared to AAV-LK04 which was assigned the value of 1. FIG. 25C is a graphical representation of the transduction/vg for AAV isolates and wildtype AAVs, without normalizing to the weakest isolate. From these data, it can be seen that AAV-LK03 is 30-times better at transducing Huh7.5 cells than AAV-DJ.

FIG. 26 is a graphical representation of the transduction/vg for various AAV isolates and wildtype AAVs on 293 cells (data shown without normalizing to the weakest isolate). These data show that AAV-LK06 is 30-times better at transducing Huh7.5 cells than is AAV-DJ.

FIG. 27 is a graphical representation of the transduction/vg for AAV isolates and wildtype AAVs on NIH3T3 cells (data shown without normalizing to the weakest isolate). These data clearly show that AAV-DJ and AAV-PAEC are the most efficient vectors at transducing NIH3T3 cells.

FIG. 28 is a graphical representation of the transduction/vg for selected AAV isolates and wildtype AAVs on Mouse Embryonic Fibroblasts (MEF) cells (data shown without normalizing to the weakest isolate). These data clearly shows that AAV-DJ is the most efficient vector at transducing MEF cells.

The results of another dot blot titer of several rAAV isolates in comparison to wildtype AAVs are presented in FIG. 29.

Figure 30:
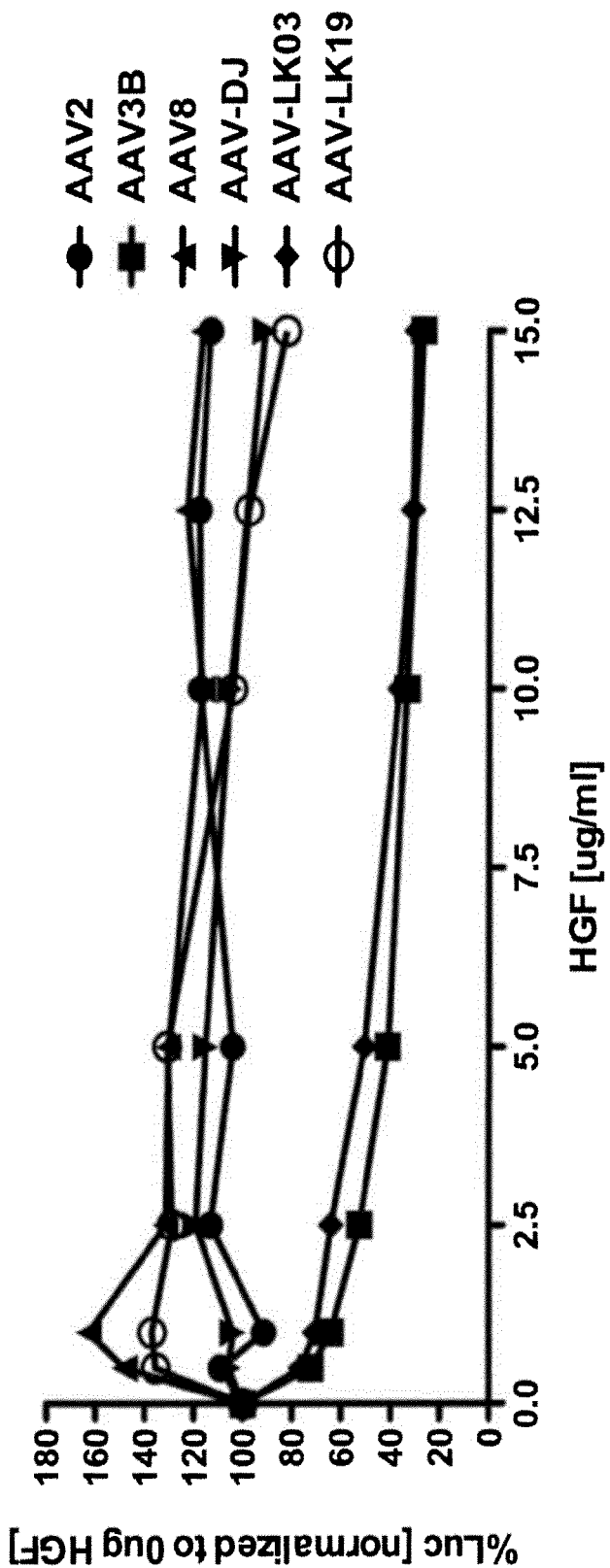
FIG. 30: illustrates the neutralizing effects of hepatocyte growth factor on some AAVs and rAAV isolates.

The neutralizing effects of hepatocyte growth factor on some AAVs and rAAV isolates is illustrated in FIG. 30.

Figure 31:
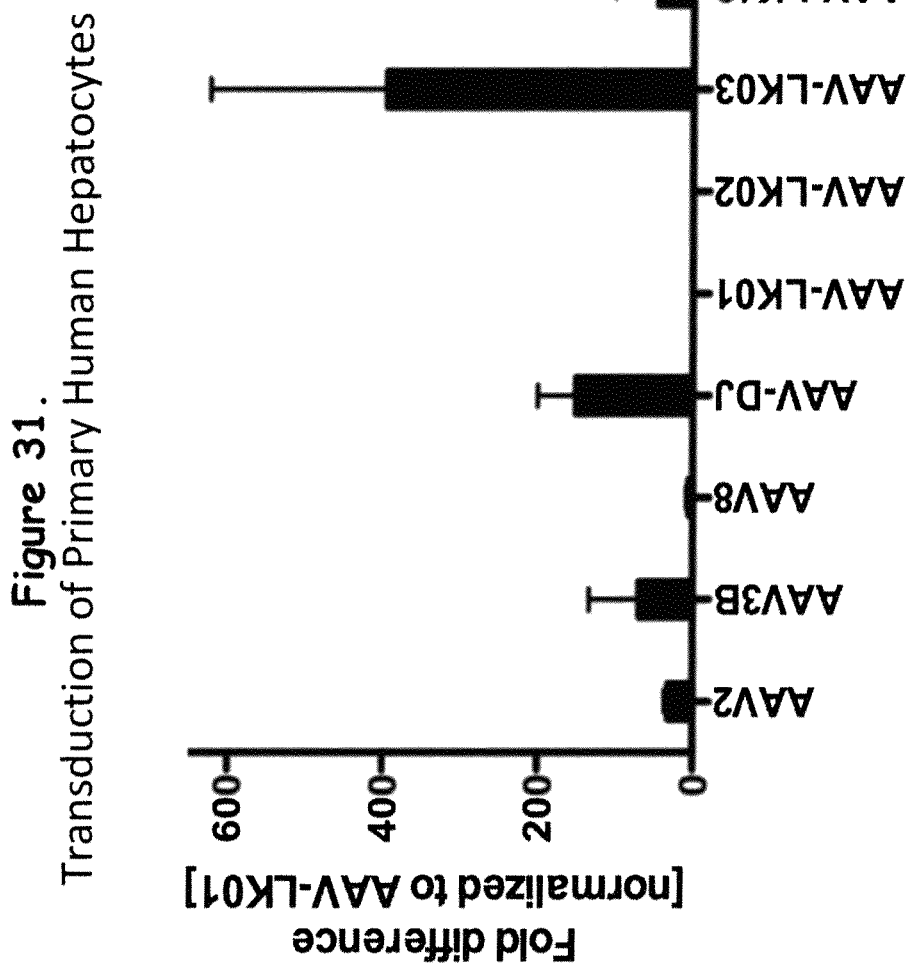
FIG. 31: shows the transduction efficiency of primary human hepatocytes by selected wildtype AAVs and rAAV isolates.

FIG. 31 shows the transduction efficiency of primary human hepatocytes by selected wildtype AAVs and rAAV isolates.

Figure 32:
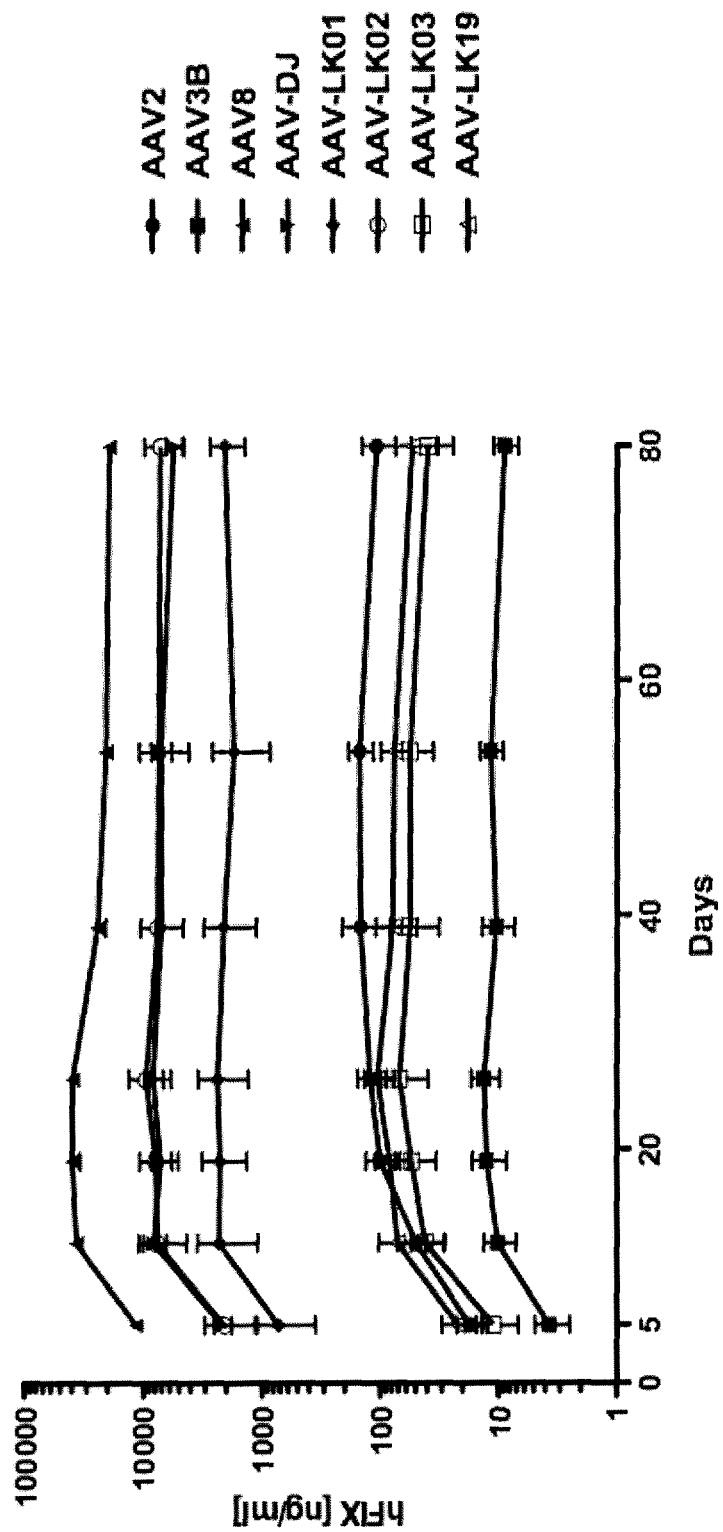
FIG. 32: compares the expression levels of recombinant human factor IX (FIX) in immunocompetent C57/BL6 mice injected with various FIX-expressing AAVs.

FIG. 32 compares the expression levels of recombinant human factor IX (FIX) in immunocompetent C57/BL6 mice injected with various FIX-expressing AAVs.

Figure 33:
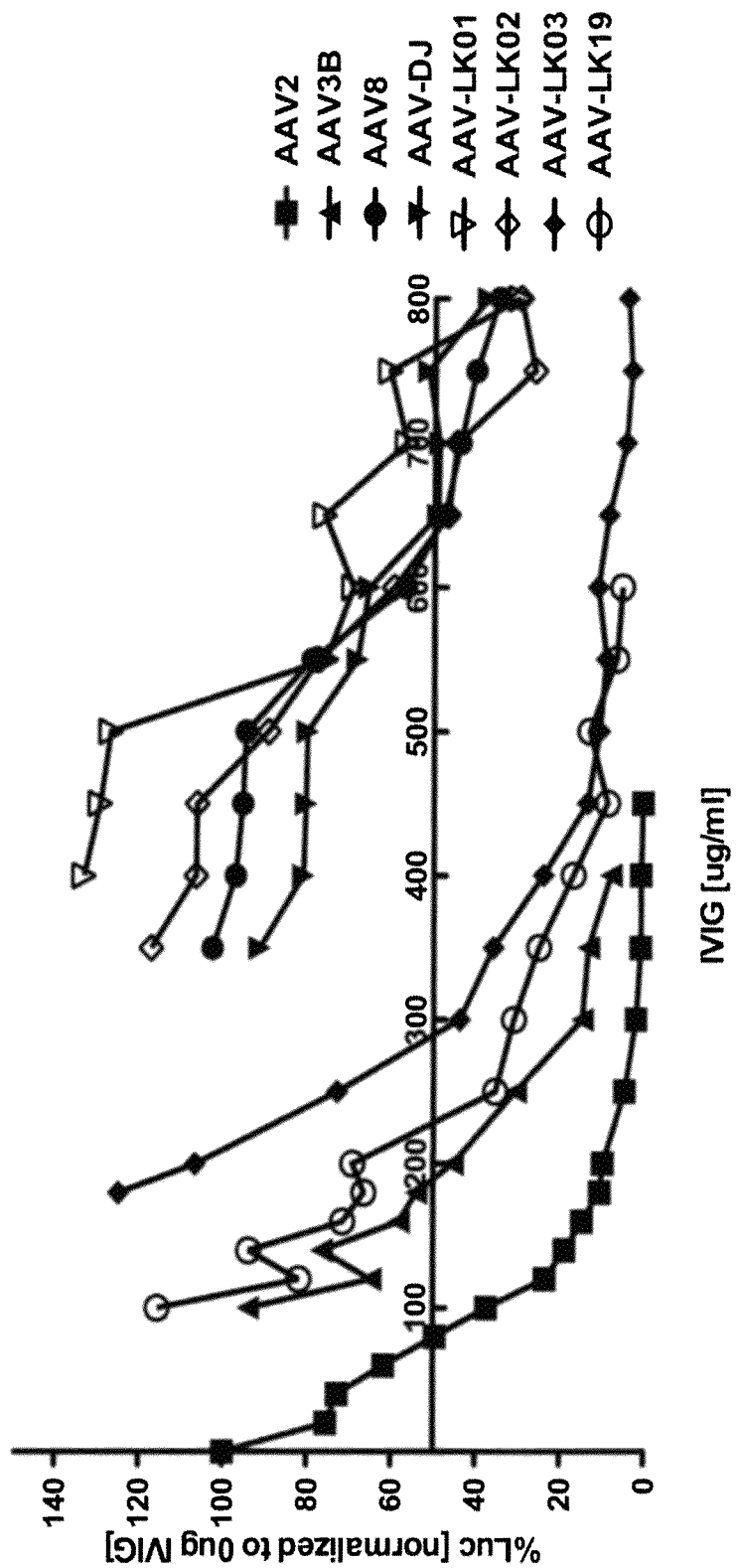
FIG. 33: compares the ability of selected rAAV isolates and wildtype AAVs to avoid neutralization by human immune globulin (IVIG)

FIG. 33 compares the ability of selected rAAV isolates and wildtype AAVs to avoid neutralization by human immune globulin (IVIG).

Figure 34:
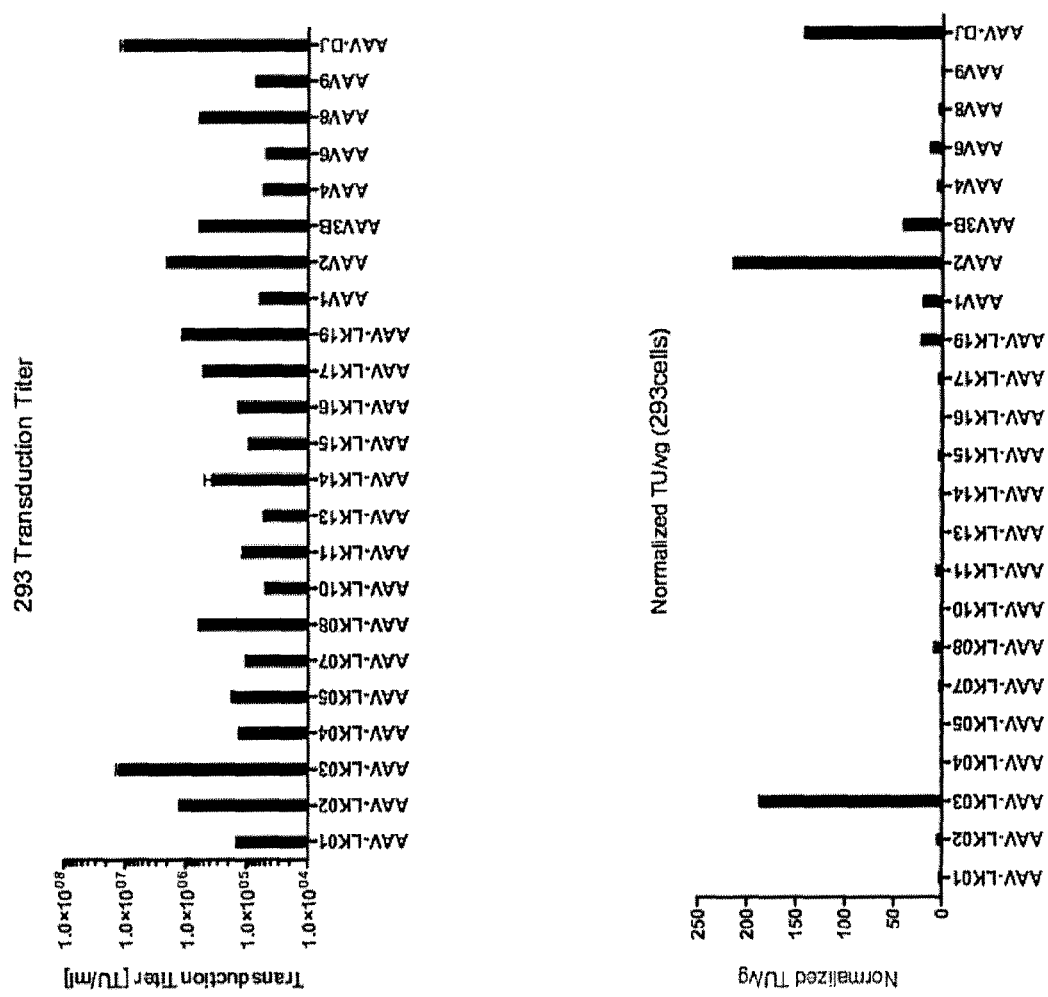
FIG. 34: compares transduction efficiency of certain rAAV isolates to wildtype AAVs in 293 cells.

FIG. 34 compares transduction efficiency of certain rAAV isolates to wildtype AAVs in 293 cells.

Figure 35:
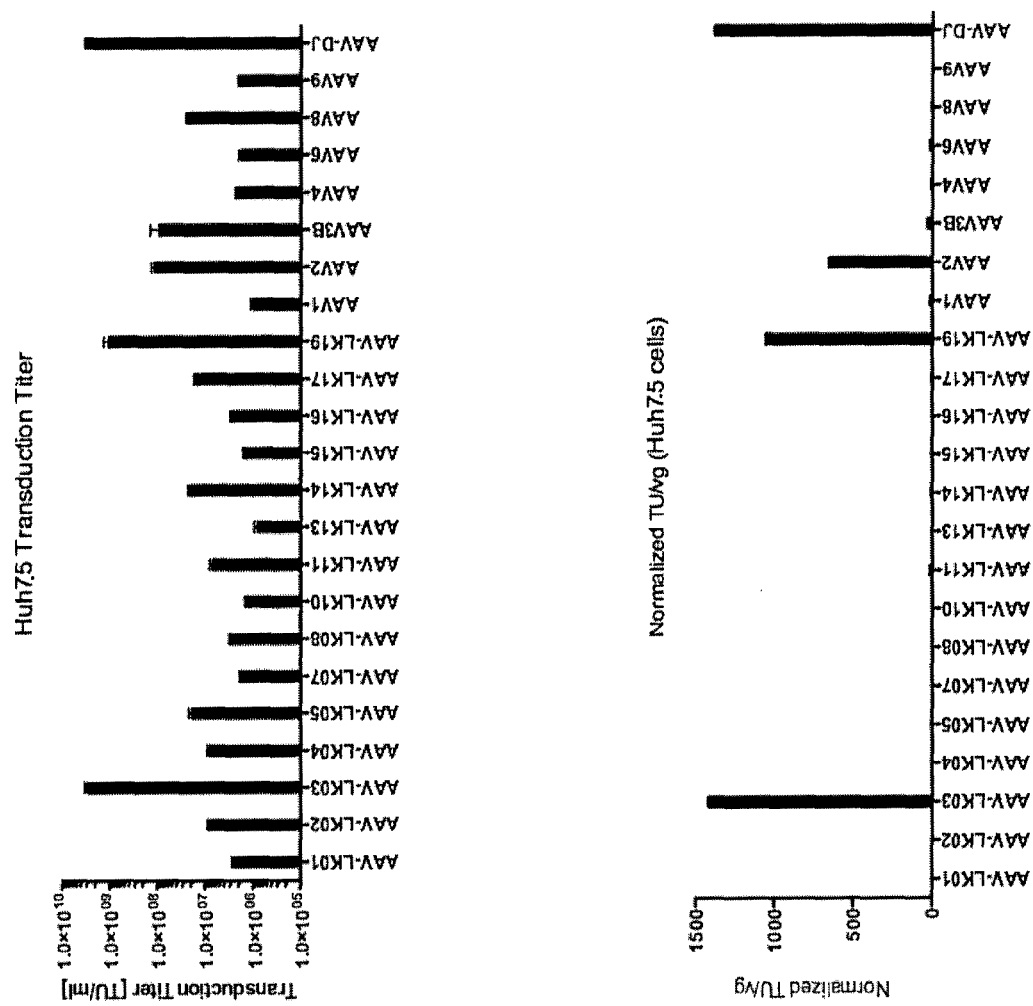
FIG. 35: compares transduction efficiency of certain rAAV isolates to wildtype AAVs in Huh 7.5 cells.

FIG. 35 compares transduction efficiency of certain rAAV isolates to wildtype AAVs in Huh 7.5 cells.

Figure 36:
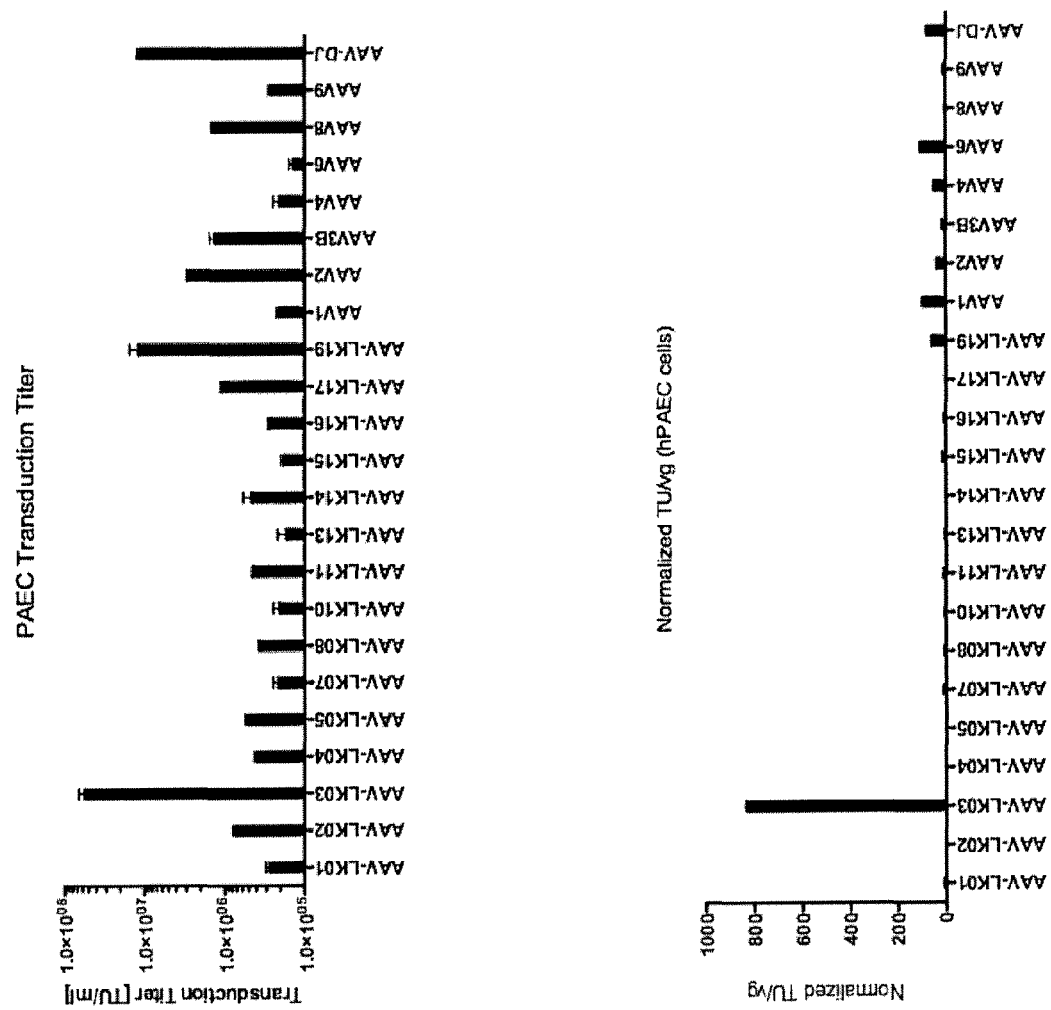
FIG. 36: compares transduction efficiency of certain rAAV isolates to wildtype AAVs in PAEC cells.
Figure 37:
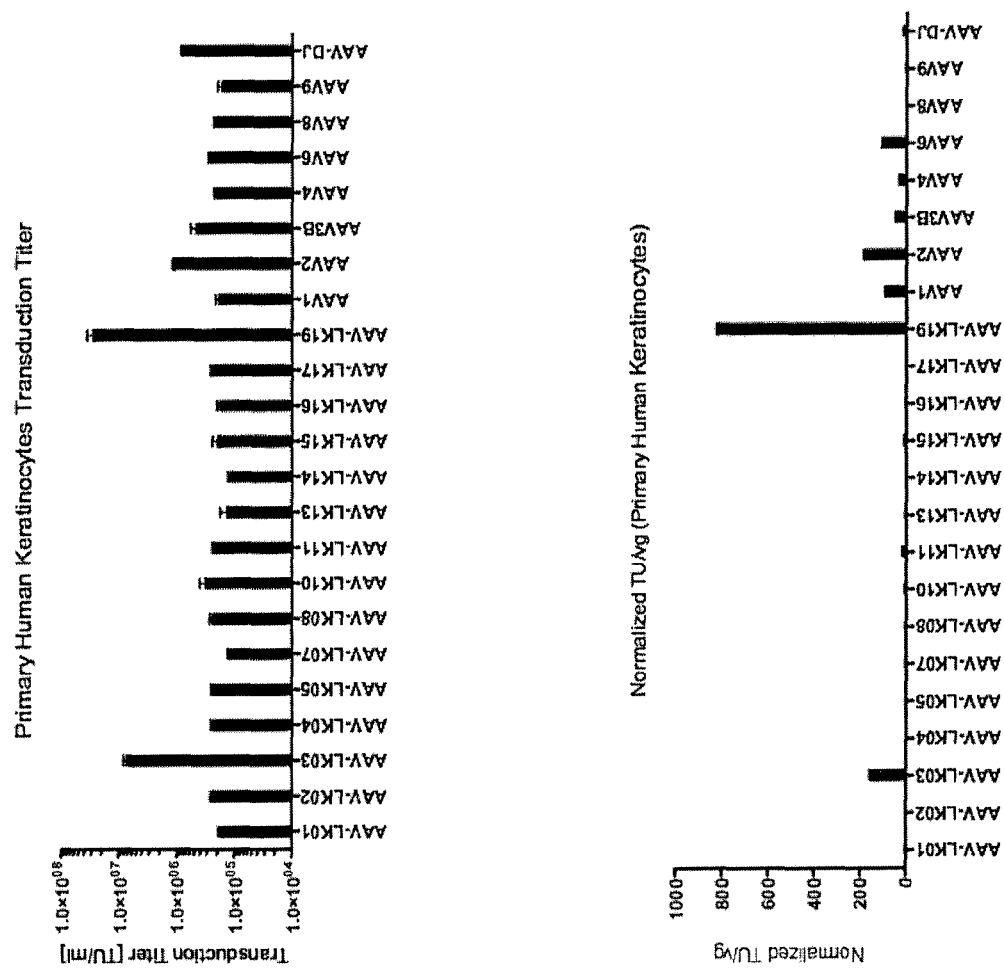
FIG. 37: compares transduction efficiency of certain rAAV isolates to wildtype AAVs in primary human keratinocytes.

FIG. 36 compares transduction efficiency of certain rAAV isolates to wildtype AAVs in PAEC cells FIG. 37 compares transduction efficiency of certain rAAV isolates to wildtype AAVs in primary human keratinocytes.

Figure 38:
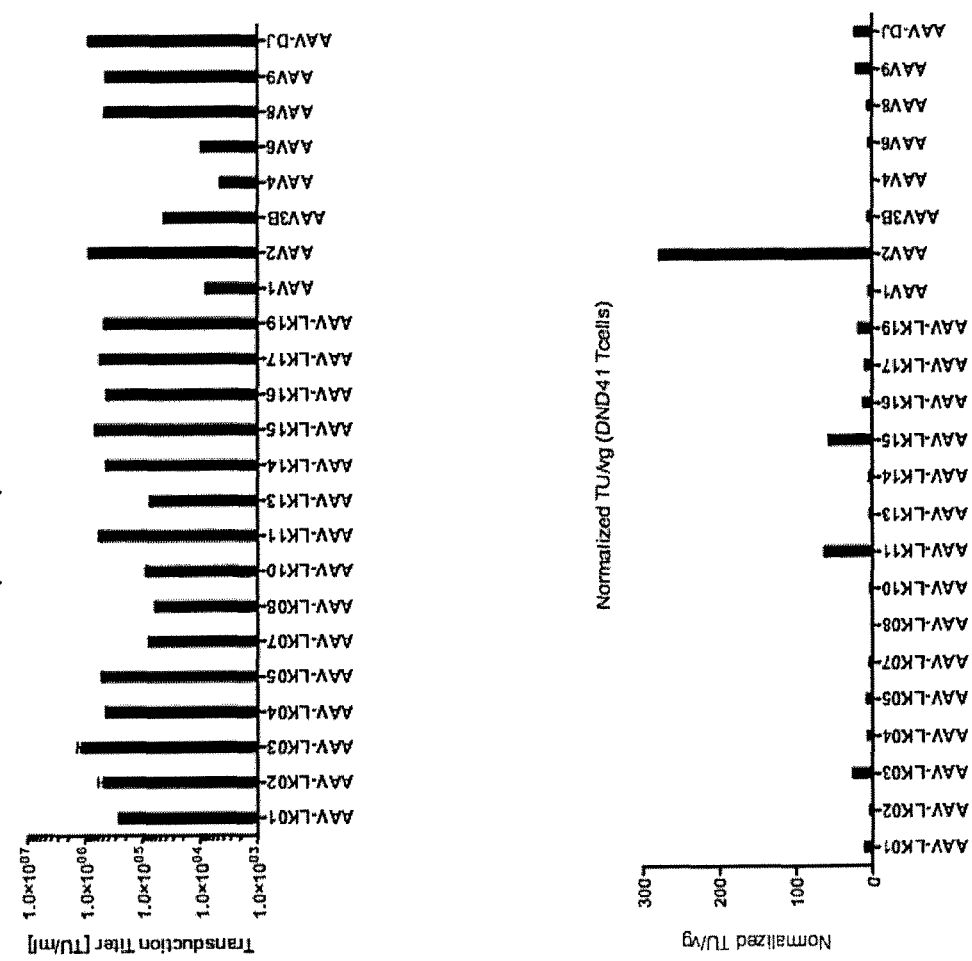
FIG. 38: compares transduction efficiency of certain rAAV isolates to wildtype AAVs in DND-41 cells.

FIG. 38 compares transduction efficiency of certain rAAV isolates to wildtype AAVs in DND-41 cells.

Figure 39:
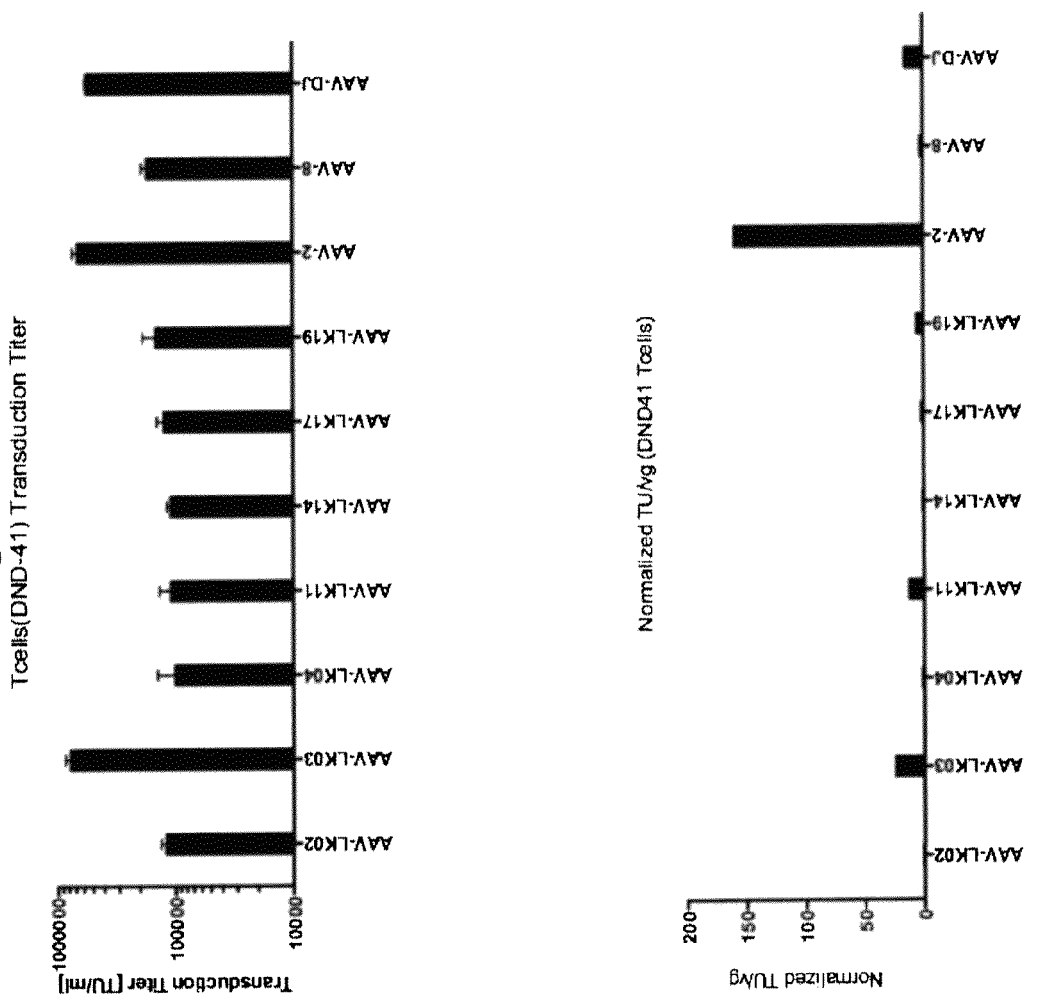
FIG. 39: compares transduction efficiency of particular rAAV isolates to wildtype AAVs in DND-41 cells.

FIG. 39 compares transduction efficiency of particular rAAV isolates to wildtype AAVs in DND-41 cells.

Figure 40:
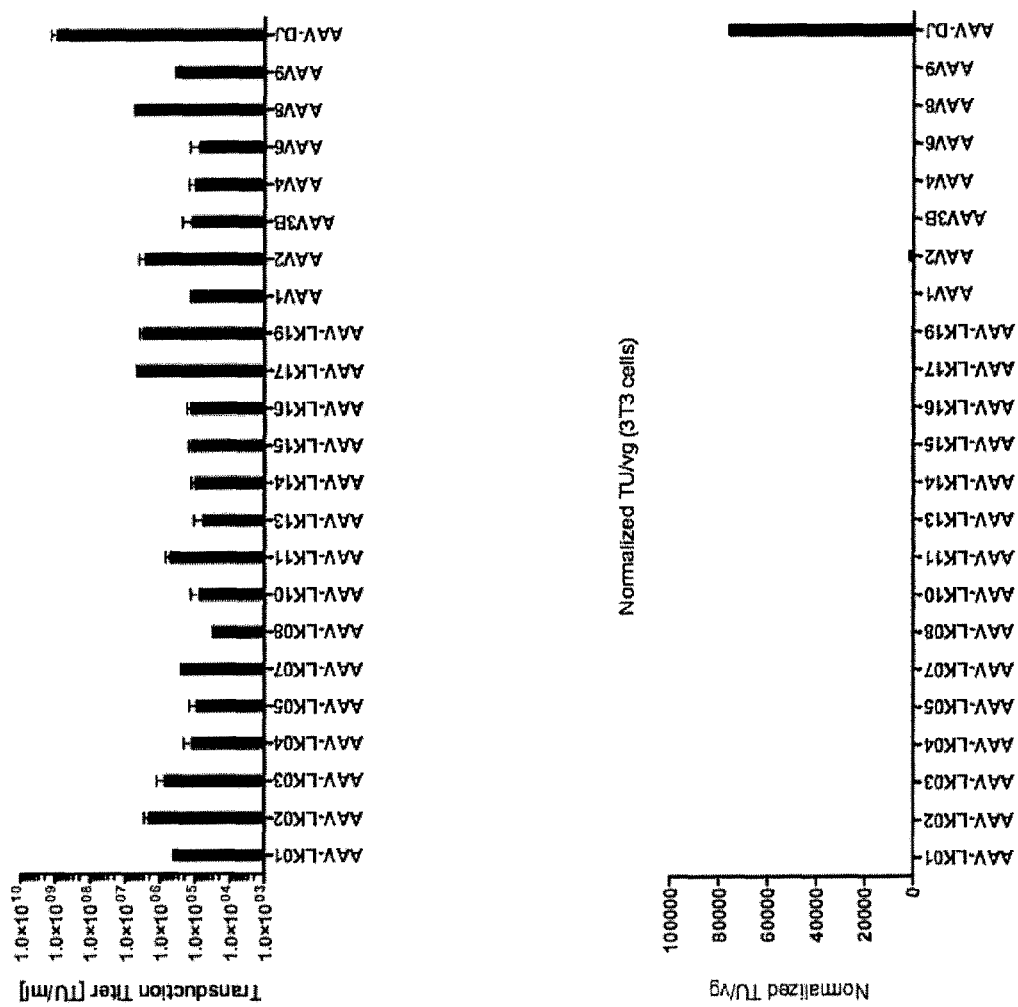
FIG. 40: compares transduction efficiency of certain rAAV isolates to wildtype AAVs in 3T3 cells.

FIG. 40 compares transduction efficiency of certain rAAV isolates to wildtype AAVs in 3T3 cells.

Figure 41:
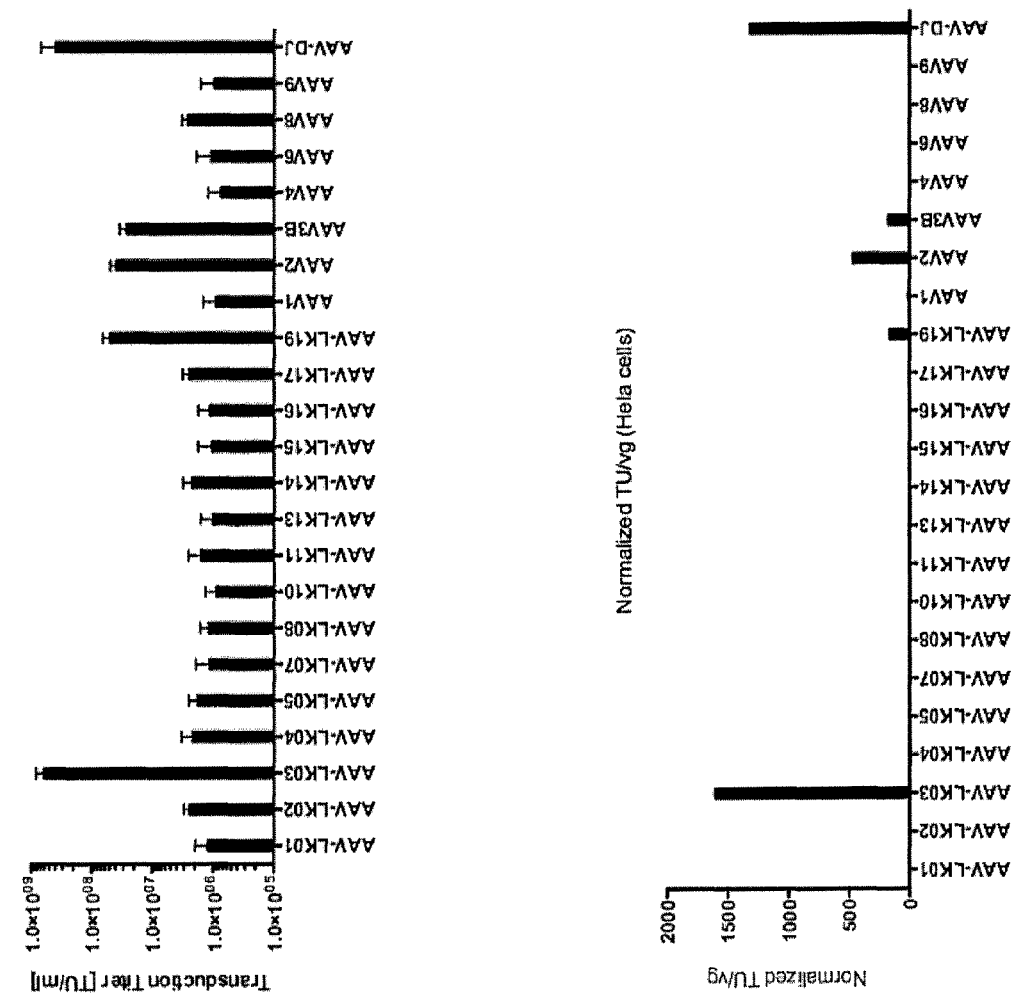
FIG. 41: compares transduction efficiency of certain rAAV isolates to wildtype AAVs in HeLa cells.

FIG. 41 compares transduction efficiency of certain rAAV isolates to wildtype AAVs in HeLa cells.

Figure 42:
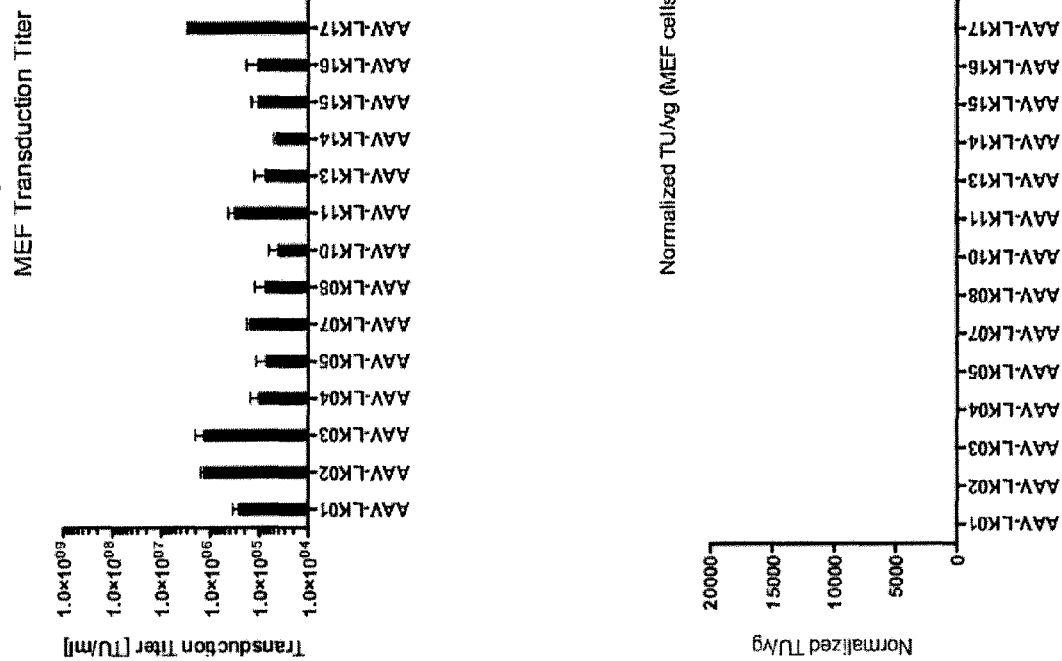
FIG. 42: compares transduction efficiency of certain rAAV isolates to wildtype AAVs in MEF cells.

FIG. 42 compares transduction efficiency of certain rAAV isolates to wildtype AAVs in MEF cells.

Figure 43:
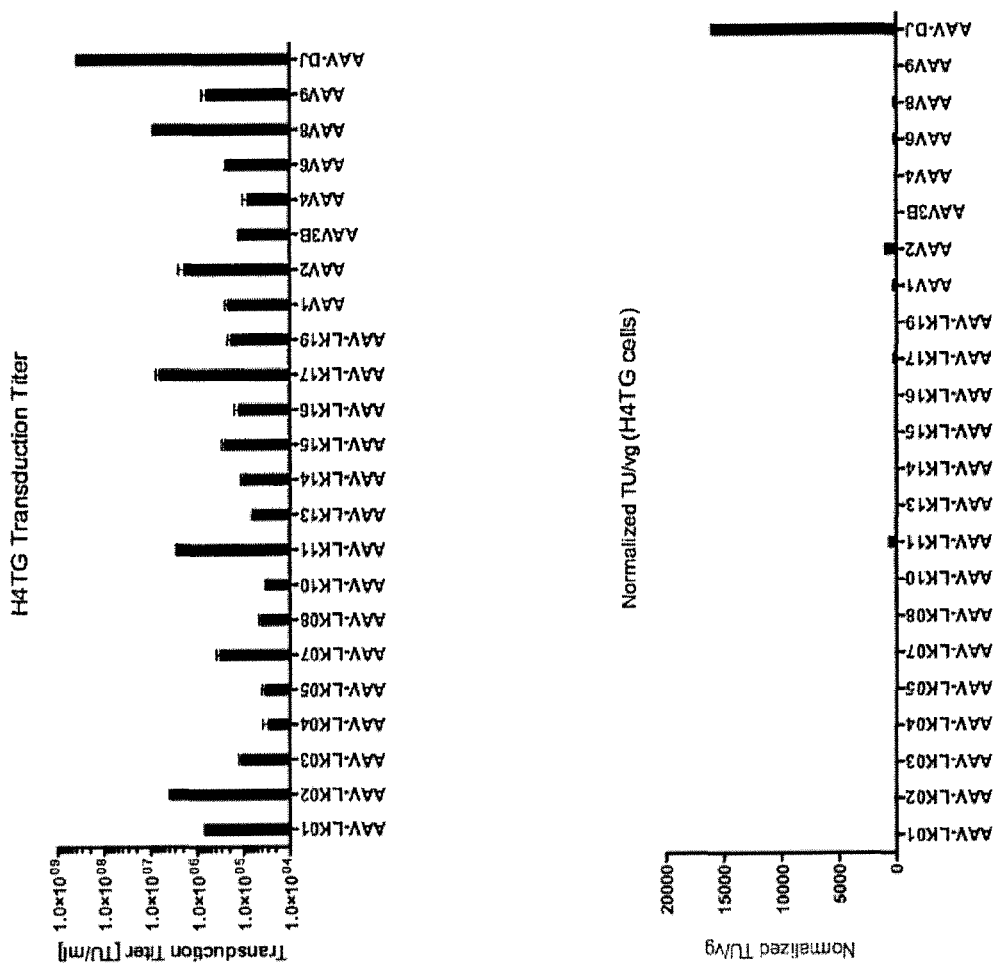
FIG. 43: compares transduction efficiency of certain rAAV isolates to wildtype AAVs in H4TG cells.

FIG. 43 compares transduction efficiency of certain rAAV isolates to wildtype AAVs in H4TG cells.

Figure 44:
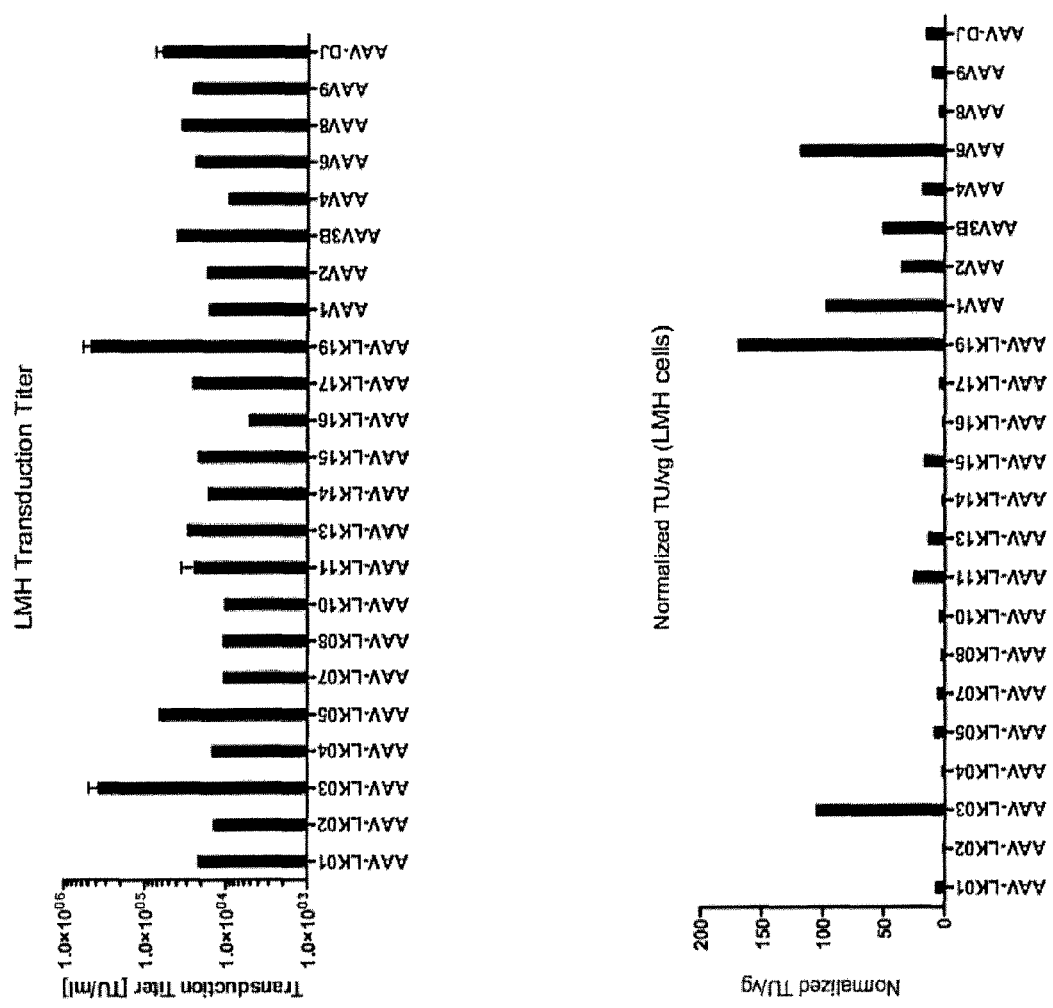
FIG. 44: compares transduction efficiency of certain rAAV isolates to wildtype AAVs in LMH cells.

FIG. 44 compares transduction efficiency of certain rAAV isolates to wildtype AAVs in LMH cells.

Figure 45:
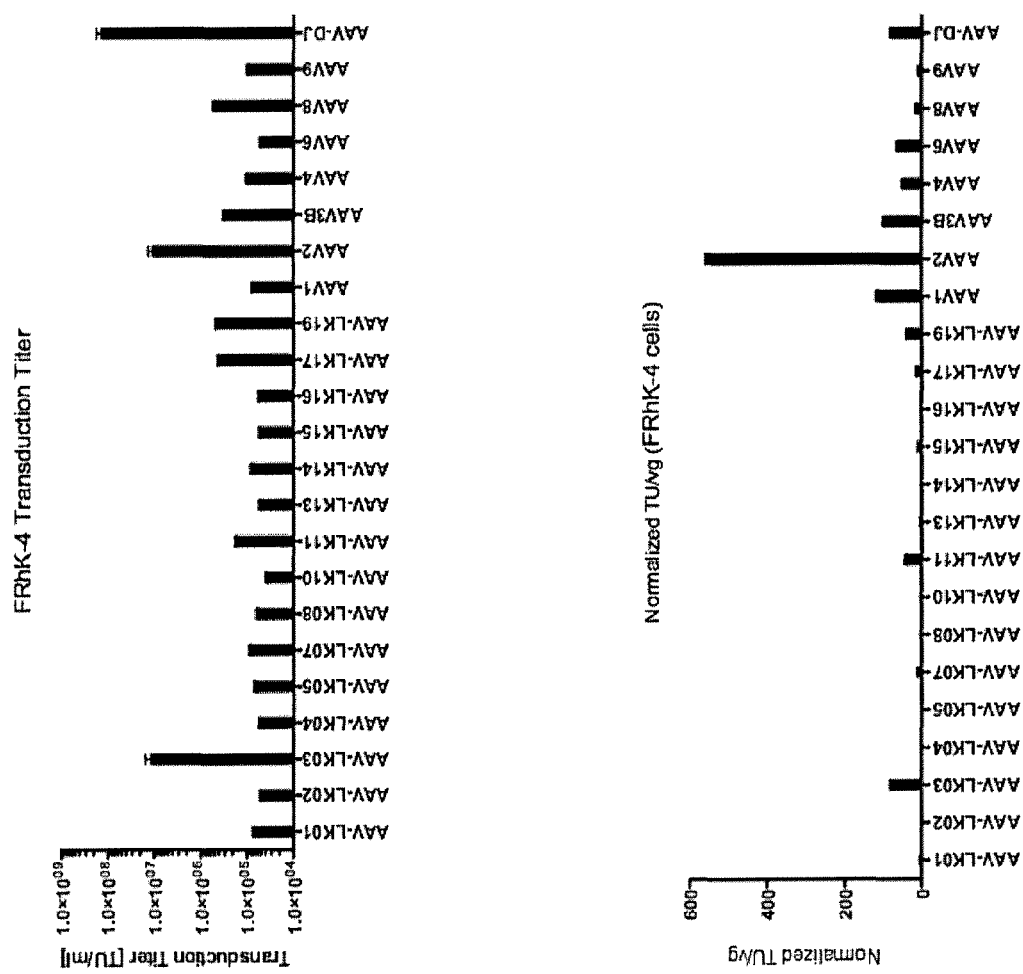
FIG. 45: compares transduction efficiency of certain rAAV isolates to wildtype AAVs in FRhK-4 cells.

FIG. 45 compares transduction efficiency of certain rAAV isolates to wildtype AAVs in FRhK-4 cells.

FIG. 46 compares the transduction of various cell lines by several wild type and recombinant AAV vectors carrying an eGFP expression cassette. Transduction titer [TU/ml] was normalized to the dot blot titer [vg/ml]. For each cell line, the vector with the lowest normalized transduction [TU/vg] was assigned the value 1 and used as a basis for normalization of all other vectors. The vector with the highest normalized transduction level for each cell line are shown in bold. Nineteen human hepatocyte-selected clones were tested.

Several rAAVs were identified by selection on human PAEC cells; these were designated as AAV-PAEC2, AAV-PAEC4, AAV-PAEC6, AAV-PAEC7, AAV-PAEC8, AAV-PAEC11, AAV-PAEC12 and AAV-PAEC13. FIG. 47 presents a schematic of the genealogical relationship on the DNA level and amino acid level between certain of these AAV-PAEC recombinants and the wildtype AAVs used to generate the library.

FIG. 48 shows the titer and transduction efficiency of several rAAV isolates obtained by selection on human PAEC cells as compared to wildtype AAVs.

In summary, several of the rAAVs were found to have increased transduction efficiency of many cell types, including primary human hepatocytes and primary human keratinocytes, compared to the previously known and efficient AAV-DJ. In some embodiments, the rAAVs were found to have at least 10 to 50 times greater transduction efficiency than AAV-DJ. Also, rAAV vectors were found to have improved resistance to neutralization by pooled human immune globulin relative to AAV-2 (currently used in clinical settings) and AAV-DJ. Such resistance is reasonable, given that the rAAV capsid was selected from a library partially based on its ability to produce virus that resists neutralization by human immune globulin. The AAV capsid selection methods and novel rAAVs identified herein and using these methods solve the problem of lack of efficacy exhibited by many gene transfer and gene therapy approaches.

While a number of exemplary aspects and embodiments have been illustrated and described, those of skill in the art will recognize certain modifications, permutations, additions and sub-combinations thereof that can be made without departing from the spirit and scope of the invention(s). It is therefore intended that the following appended claims and claims hereafter introduced are interpreted to include all such modifications, permutations, additions and sub-combinations as are within their true spirit and scope, and it is to be understood that the disclosure is not to be limited to the specific embodiments disclosed herein, as such are presented by way of example. Although specific terms are employed herein, they are used in a generic and descriptive sense only and not for purposes of limitation.

All literature and similar materials cited in this application, including, but not limited to, patents, patent applications, articles, books, treatises, internet web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

What is claimed is:

1. A nucleotide sequence encoding a capsid protein, wherein the capsid protein has at least 99% sequence identity to SEQ ID NO: 31.

2. The nucleotide sequence of claim 1, wherein said capsid protein sequence is encoded by the nucleotide sequence of SEQ ID NO: 4 or SEQ ID NO: 19.

3. A viral particle comprising the nucleotide sequence of claim 1.

4. A plasmid comprising the nucleotide sequence of claim 1.

5. A recombinant AAV particle, comprising a capsid protein with at least 99% sequence identity to SEQ ID NO: 31.

6. The nucleotide sequence of claim 1, wherein the capsid protein is identical to SEQ ID NO: 31.

7. A viral particle comprising the nucleotide sequence of claim 6.

8. A plasmid comprising the nucleotide sequence of claim 6.

9. The recombinant AAV particle of claim 5, wherein the capsid protein is identical to SEQ ID NO: 31.

10. A capsid protein with at least 99% sequence identity to SEQ ID NO: 31.

11. A capsid protein identical to SEQ ID NO: 31.

* * * * *

UNITED STATES PATENT AND TRADEMARK OFFICE
CERTIFICATE OF CORRECTION

PATENT NO. : 9,169,299 B2
APPLICATION NO. : 13/594773
DATED : October 27, 2015
INVENTOR(S) : Leszek Lisowski et al.

It is certified that error appears in the above-identified patent and that said Letters Patent is hereby corrected as shown below:

Title page under item (73) Assignee: change "THE BOARD OF TRUSTEES OF THE LELEAND STANFORD JUNIOR UNIVERSITY, Palo Alto, CA" to --THE BOARD OF TRUSTEES OF THE LELAND STANFORD JUNIOR UNIVERSITY, Palo Alto, CA--

Signed and Sealed this
Twenty-fourth Day of May, 2016

Michelle K. Lee
*Director of the United States Patent and Trademark Office*